(12) United States Patent
Hecker et al.

(10) Patent No.: US 9,149,543 B2
(45) Date of Patent: Oct. 6, 2015

(54) METHODS AND MODELS FOR RAPID, WIDESPREAD DELIVERY OF GENETIC MATERIAL TO THE CNS USING NON-VIRAL, CATIONIC LIPID-MEDIATED VECTORS

(75) Inventors: James G. Hecker, Media, PA (US); Micheal Nantz, Louisville, KY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1914 days.

(21) Appl. No.: 12/086,605

(22) PCT Filed: Dec. 14, 2006

(86) PCT No.: PCT/US2006/048093
§ 371 (c)(1),
(2), (4) Date: Jun. 16, 2010

(87) PCT Pub. No.: WO2007/070705
PCT Pub. Date: Jun. 21, 2007

(65) Prior Publication Data
US 2010/0249208 A1 Sep. 30, 2010

Related U.S. Application Data

(60) Provisional application No. 60/751,470, filed on Dec. 15, 2005.

(51) Int. Cl.
*C12N 15/11* (2006.01)
*A61K 48/00* (2006.01)
*A61K 9/127* (2006.01)

(52) U.S. Cl.
CPC ........... *A61K 48/0075* (2013.01); *A61K 9/1272* (2013.01); *A61K 48/0008* (2013.01); *A61K 48/0025* (2013.01)

(58) Field of Classification Search
CPC ........................ A61K 48/0075; A61K 48/0008
See application file for complete search history.

(56) References Cited

U.S. PATENT DOCUMENTS

| | | |
|---|---|---|
| 4,078,052 A | 3/1978 | Papahadjopoulos |
| 4,089,801 A | 5/1978 | Schneider |
| 4,145,410 A | 3/1979 | Sears |
| 4,224,179 A | 9/1980 | Schneider |
| 4,235,871 A | 11/1980 | Papahadjopoulos |
| 4,310,506 A | 1/1982 | Baldeschwieler |
| 4,394,372 A | 7/1983 | Taylor |
| 4,522,803 A | 6/1985 | Lenk |
| 4,588,578 A | 5/1986 | Fountain |
| 4,599,227 A | 7/1986 | Dees |
| 4,610,868 A | 9/1986 | Fountain |
| 4,752,425 A | 6/1988 | Martin |
| 4,769,250 A | 9/1988 | Forssen |
| 4,771,612 A | 9/1988 | Kurikka |
| 4,781,871 A | 11/1988 | West |
| 4,812,449 A | 3/1989 | Rideout |
| 4,975,282 A | 12/1990 | Cullis |
| 5,000,959 A | 3/1991 | Iga |
| 5,013,556 A | 5/1991 | Woodle |
| 5,021,200 A | 6/1991 | Vanlerberghe |
| 5,077,056 A | 12/1991 | Bally et al. |
| 5,168,050 A | 12/1992 | Hammonds |
| 5,171,678 A | 12/1992 | Behr |
| 5,186,923 A | 2/1993 | Piwnica-Worms |
| 5,204,112 A | 4/1993 | Hope |
| 5,208,036 A | 5/1993 | Eppstein |
| 5,211,955 A | 5/1993 | Legros |
| 5,264,618 A | 11/1993 | Felgner |
| 5,277,897 A | 1/1994 | Piwnica-Worms |
| 5,279,833 A | 1/1994 | Rose |
| 5,334,381 A | 8/1994 | Unger |
| 5,334,391 A | 8/1994 | Clark |
| 5,334,761 A | 8/1994 | Gebeyehu |
| 5,527,928 A | 6/1996 | Nantz |
| 5,744,625 A | 4/1998 | Nantz |
| 5,824,812 A | 10/1998 | Nantz |
| 5,869,715 A | 2/1999 | Nantz |
| 5,892,071 A | 4/1999 | Nantz |
| 5,925,623 A | 7/1999 | Nantz |
| 6,043,390 A | 3/2000 | Nantz |
| 6,096,716 A | 8/2000 | Hayes |
| 6,110,490 A | 8/2000 | Thierry |
| 6,200,599 B1 | 3/2001 | Nantz |
| 6,372,722 B1 | 4/2002 | Bennett |

OTHER PUBLICATIONS

Bence et al. "Impairment of the Ubiquitin-Proteasome System by Protein Aggregation," Science 292:1552-1555 (2001).
Hecker et al. "Self-Limited Gene Expression In-Vitro in Neuronal Cell Cultures and In-Vivo in Rat Brain Using mRNA/ . . . ," Anesth. Analg. 84:S1-S599 (1997), Abstract only.
Hecker et al. "Catastrophic Cardiovascular Collapse During Carotid Endarterectomy," J. Cadriothoracic and Vasc. Anesth. 20(2):259-268 (2006).
Hecker, Society for Neuroscience, abstract, 2005.
"Gene Transfer and Therapy Clinical Trials—Update: Part 1: Countries, Diseases, Clinical trial phases, Routes of administration," J. Gene Med. 1:71-73 (1999).

(Continued)

*Primary Examiner* — J. E. Angell
(74) *Attorney, Agent, or Firm* — Riverside Law LLP

(57) ABSTRACT

Provided are safe, non-invasive, non-viral delivery methods for providing a nucleic acid into the neuronal and non-neuronal cells of the central nervous system (CNS) of a subject to protect neuronal and non-neuronal cells from ischemic or traumatic injury, wherein the nucleic acid encodes a therapeutic proteins, specifically providing rapid transient expression and widespread distribution for in vitro or in vivo applications. Further provided are methods for the intrathecal delivery to the cerebrospinal fluid (CSF) of a neuroprotective gene sequence, e.g., a heat shock protein (HSP), complexed with cationic lipid compositions to achieve such delivery, and the complexes used therein.

18 Claims, 13 Drawing Sheets

(56) References Cited

OTHER PUBLICATIONS

"Gene Transfer and Therapy Clinical Trials—Update: Part 2: Delivery Systems Used and Genes Transferred," J. Gene Med. 1:151-153 (1999).
Wells et al. "HSP101 functions as a specific translational regulatory protein whose activity is regulated by nutrient status," Genes & Dev. 12:3236-3251 (1998).
Yenari et al. "Gene Therapy with HSP72 IS Neuroprotective in Rat Models of Stroke and Epilepsy," Annals of Neurology 44(4):584-591 (1998).
Betz et al. "Attenuation of Stroke Size in Rats Using and Adenoviral Vector to Induce Overexpression of Interleukin-1 . . . ," J. Cerebral Blood Flow and Metab. 15:547-551 (1995).
Biewenga et al. "Plasmid-mediated gene transfer in neurons using the biolistics technique," J. Neurosci. Methods 71:67-75 (1997).
Hauck et al. "Whole Animal In Vivo Imaging Ater Transient, Nonviral GEne delivery to the Rat Central Nervous System," Mol. Therapy 16(11):1857-1864 (2008).
Starr et al. "Long-term persistence of defective HSV-1 vectors in the rat brain is demonstrated by reactivation of vector gene expression," Gene Therapy 3:615-623 (1996).
Wilke et al. "Efficacy of a peptide-based gene delivery system depends on mitotic activity," Gene Therapy 3:1133-1142 (1996).
Wolff et al. "Direct Gene Transfer into Mouse Muscle in Vivo," Science Reports 247:1465-1468 (1990).
Anderson et al. "Stability of mRNA/Cationic Lipid Lipoplexes in Human and Rat Cerebrospinal Fluid: Methods . . . ," Human Gene Therapy 14:191-202 (2003).
Auluck et al., "Chaperone Suppression of alpha-Synuclein Toxicity in a Drosophila Model for Parkinson's Disease," Science 295:865-868 (2002).
Bally et al., "Biological barriers to cellular delivery of lipid-based DNA carriers," Adv. Drug Deliv. Rev. 38:291-315 (1999).
Benevenisty et al., "Direct introduction of genes into rats and expression of the genes," Proc. Natl. Sci. USA 83:9551-9555 (1986).
Boado et al., "Ten Nucleotide cis element in the 3'-untranslated region of the GLUT1 glucose transporter . . . ," Mol. Brain Res. 59:109-113 (1998).
Bradford, "A Rapid and Sensitive Method for the Quantitation of Microgram Quantities . . . ," Analytical Biochem. 72:248-254 (1976).
Brisson et al., "Subcellular Trafficking of the Cytoplasmic Expression System," Human Gene Therapy 10:2601-2613 (1999).
Byk et al., "Genetic Chemistry: Tools for Gene Therapy Coming From Unexpected Directions," Drug Develop. Res. 50:566-572 (2000).
Byrnes et al., "Large-Plaque Mutants of Sindbis Virus Show Reduced Binding to Heparan Sulfate . . . ," Journal of Virology 74:644-651 (2000).
Byrnes et al., "Adenovirus Gene Transfer Causes Inflammation in the Brain," Neuroscience 66:1015-1024 (1995).
Chan et al., "Tissue-specific consequences of the anti-adenoviral immune response: implications . . . ," Nature Medicine 5:1143-1149 (1999).
Chapman et al., "Effect of intron A from human cytomegalovirus (Towne) immediate-early gene . . . ," Nucleic Acids Res. 19:3979-3986 (1991).
Chesnoy et al., "Enhanced Cutaneous Gene Delivery Following Intradermal Injection of Naked DNA in a High . . . ," Mol. Ther. 5:57-62 (2002).
Chirmule et al., "Immune reponses to adenovirus and adeno-associated virus in humans," Gene Therapy 6:1574-1583 (1999).
Cichon et al., "Intravenous Administration of Recombinant Adenoviruses Causes Thrombocytopenia . . . ," J. Gene Medicine 1:360-371 (1999).
Constantini et al., "Gene Therapy in the CNS," Gene Therapy 7:93-109 (2000).
Constantini et la., Gene Transfer to the Nigrostriatal System by Hybrid Herpes Simplex . . . , Human Gene Therapy 10:2481-2494 (1999).

Cornetta et al., "Safety Issues Related to Retoviral-Mediated Gene Transfer in Humans," Human Gene Therapy 2:5-14 (1991).
Cummings et al., "Over-expression of inducible HSP70 chaperone supresses neuropathy and improves . . . ," Human Mol. Genetics 10:1511-1518 (2001).
Dewey et al., "Chronic brain inflammation and persistent herpes simplex virus 1 thymidine kinase . . . ," Nature Medicine 5:1256-1263 (1999).
Dong et al., "Hsp70 Gene Transfer by Adeno-associated Virus Inhibits MPTP-Induced Nigrostriatal . . . ," Molecular Therapy 11:80-88 (2005).
Driesse et al., "Intra-CSF administered recombinant adenovirus causes an immune response-mediated . . . ," Gene Therapy 7:1401-1409 (2000).
Driesse et al., "Distribution of Recombinant Adenovirus in the Cerebrospinal Fluid . . . ," Human Gene Therapy 10:2347-2354 (1999).
Engelhardt et al., "Adenovirus-Mediated Transfer of the CFTR Gene to Lung of Nonhuman Primates . . . ," Human Gene Therapy 4:759-769 (1993).
Felgner et al., "Enhanced Gene Delivery and Mechanism Studies with a Novel Series of Cationic Lipid Formulations," J. Biol. Chem. 269:2550-2561 (1994).
Fink et al., "Defective Herpes Simplex Virus Vectors Expressing the Rat Brain Stress-Inducible Heat Shock Protein . . . ," J. Neurochemistry 68:961-969 (1997).
Gallie et al., "RNA pseudoknot domain of tobacco mosiac virus can functionally substitute for a poly(A) . . . ," Genes Develop. 4:1149-1157 (1990).
Gallie et al., "Identification of the motifs within the tobacco mosaic virus 5'-leader responsible . . . ," Nucl. Acids Res. 20:4631-4638 (1992).
Geller et al., "Infection of cultured central nervous system neurons with a defective herpes simplex . . . ," Proc. Natl. Acad. Sci. USA 87:1149-1153 (1990).
Giffard et al., "Many Mechanisms for Hsp70 Protection From Cerebral Ischemia," J. Neurosurg. Anesthiol. 16:53-61 (2004).
Giffard et al., "Chaperones, protein aggregation, and protection from hypoxic/ischemic brain injury," J. Exp. Biol. 207:3213-3220 (2004).
Girao Da Cruz et al., "Kinetic analysis of the initial steps involved in lipoplex-cell interactions: effect of various . . . ," Biochim. Biophys. Acta. 1510:136-151 (2001).
Hoehn et al., "Overexpression of HSP72 After Induction of Experimental Stroke Protects Neurons From Ischemic Damage," J. Cerebral Blood Flow Metab. 21:1303-1309 (2001).
Holt et al., "Lipofection of cDNAs in the Embryonic Vertebrate Central Nervous System," Neuron 4:203-214 (1990).
Imaoka et al., "Significant Behavioral Recovery in Parkinson's Disease Model by Direct Intracerebral Gene Transfer Using Continuous . . . ," Human Gene Therapy 9:1093-1102 (1998).
Jacobson et al., "Interrelationships of the Pathways of mRNA Decay and Translation in Eukaryotic Cells," Ann. Rev. Biochem. 65:693-739 (1996).
Jiao et al., "Particle Bombardment-Mediated Gene Transfer and Expression in Rat Brain Tissues," Biotechnology 11:497-502 (1993).
Karpati et al., "The principles of gene therapy for the nervous system," Trends in Neurosciences 19:49-54 (1996).
Keogh et al., "High efficiency reporter gene transfection of vascular tissue in vitro and in vivo using a cationic lipid-DNA complex," Gene Therapy 4:162-171 (1997).
Krieg et al., "Functional Messenger RNAs are produced by SP6 in vitro transcription of cloned cDNAs," Nucl. Acids Res. 14:7057-7070 (1984).
Krisky et al., "Deletion of multiple immediate-early genes from herpes siplex virus reduces cytoxicity and permits long-term gene . . . ," Gene Therapy 5:1593-1603 (1998).
Li et al., "Heat Shock Protien 70 Inhibits Apoptosis Downstream of Cytochrome c Release and Upstream of Caspase-3 Activation," J. Biol. Chem. 275:25665-25671 (2000).
Lowenstein et al., "The Stress Protein Response in Cultured Neurons: Characterization and Evidence for a Protective Role in Excitotoxicity," Neuron 7:1053-1060 (1991).

(56) References Cited

OTHER PUBLICATIONS

Lu et al., "Geldanamycin induces heat shock proteins in brain and protects against focal cerebral ischemia," J. Neurochem. 81:355-364 (2002).
Luo et al., "Synthetic DNA delivery systems," Nature Biotechnology 18:33-37 (2000).
Malone et al., "Cationic liposome-mediated RNA transfection," Proc. Nat'l. Acad. Sci. USA 86:6077-6081 (1989).
Mattaj et al., "Nucleocytoplasmic Transport: The Soluble Phase," Annu. Rev. Biochem. 67:265-306 (1998).
Melchior et al., "Two-way trafficking with Ran," Trends Cell. Biol. 8:175-179 (1998).
Melton et al., "Efficient in vitro synthesis of biologically active RNA and RNA hybridization probes from plasmids containing . . . ," Nucl. Acids Res. 12:7035-7056 (1984).
Mestril et al., "Adenovirus-mediated Gene Transfer of a Heat Shock Protein 70 (hsp70i) Protects Against Simulated Ischemia," J. Mol. Cell. Cardiol. 28:2351-2358 (1996).
Meuli-Simmen et al., "Gene Expression along the Cerebral-Spinal Axis after Regional Gene . . . ," Human Gene Therapy 10:2689-2700 (1999).
Mohr et al., "Axonal transport of neuropeptide encoding mRNAs within the hypothalamo-hypophyseal tract if rats," EMBO J. 10:2419-2424 (1991).
Monahan et al., "AAV vectors: is clinical success on the horizon?," Gene Therapy 7:24-30 (2000).
Morris et al., "Therapy of Head and Neck Squamous Cell Carcinoma with an Oncolytic Advenovirus Expressing HSV-tk," Molecular Therapy 1:56-62 (2000).
Mountain, "Gene therapy: the first decade," Trends in Biotechnology 18:119-128 (2000).
Mortimer et al., "Cationic lipid-mediated transfection of cells in culture requires mitiotic activity," Gene Therapy 403-411 (1999).
Muchowski et al., "Modulation of Neurodegeneration by Molecular Chaperones," Nat. Rev. Neurosci. 6:11-22 (2005).
Narasimhan et al., "Astrocyte Survival and HSP70 Heat Shock Protein Induction Following Heat Shock and Acidosis," Glia 17:147-159 (1996).
Nicolau et al., "Liposome-Mediated DNA Transfer in Eukaryotic Cells—Dependence of the Transfer . . . ," Biochim. Biophys. Acta. 721:185-190 (1982).
O'Brien et al., "Lysine 71 of the Chaperone Protein Hsc70 Is Essential for ATP Hydrolysis," J. Biol. Chem. 271:15874-15878 (1996).
Ohno et al., "Role of the C-terminal region of mouse inducible Hsp72 in the recognition of peptide substrate for chaperone activity," FEBS Lett. 576:381-386 (2004).
Paillard et al., "Gene Transfer to Neurons with Herpes Simplex Virus/Adeno-Associated Virus Hybrid Vectors," Human Gene Therapy 10:2441-2443 (1999).
Park et al., "Efficient lentiviral transduction of liver requires cell cycling in vivo," Nature Genetics 24:49-52 (2000).
Peltekian et al., "Adenovirus-mediated gene transfer to the brain: methodological assessment," J. Neurosci. Meth. 71:77-84 (1997).
Planas et al., "The Heat Shock Stress Response After Brain Lesions: Induction of 72 KDA Heat Shock Protein . . . ," Prog. Neurobiol. 51:607-636 (1997).
Ponder et al., "Evaluation of Relative Promotor Strength in Primary Hepatocytes Using Optimized Lipofection," Human Gene Therapy 2:41-52 (1991).
Rajdev et al., "Mice Overexpressing Rat Heat Shock Protein 70 Are Protected against Cerebral Infarction," Ann. Neurol. 47:782-791 (2000).
Ray et al., "Proliferation, differentiation, and long-term culture of primary hippocampal neurons," Proc. Natl. Acad. Sci. USA 90: 3602-3606 (1993).
Rennels et al., "Evidence for a 'Paravascular' Fluid Circulation in the Mammalian Central Nervous System . . . ," Brain Research 326:47-63 (1985).
Schleef et al., "Animal-free production of ccc-supercoiled plasmids for research and clinical applications," J. Gene Med. 6:S45-S53 (2004).
Simon et al., "Adenovirus-Mediated Transfer of the CFTR Gene to Lung of Nonhuman Primates: Toxicity Study," Human Gene Therapy 4:771-780 (1993).
Smith et al., "Intracranial Administration of Adenovirus Expressing HSV-TK in Combination with Ganciclovir Produces a Dose Dependent . . . ," Human Gene Therapy 8:943-954 (1997).
Steel et al., "HSP72 Inhibits Apoptosis Upstream of the Mitochondria and Not through Interactions with Apaf-1," J. Biol. Chem. 279:51490-51499 (2004).
Strong et al., "Incorporation of beta-globin untranslated regions into a Sindbis virus vector for augmentation . . . ," Gene Therapy 4:624-627 (1997).
Tanguay et al., "Isolation and Characterization of the 102-Kilodalton RNA-binding Protein That Binds . . . ," J. Biol. Chem. 271:14316-14322 (1996).
Tidwell et al., "Administration of Hsp70 in vivo inhibits motor and sensory neuron degeneration," Cell Stress Chaperones 9:88-98 (2004).
Trono, "Lentiviral vectors: turning a deadly foe into a therapeutic agent," Gene Therapy 7:20-23 (2000).
Wang et al., "Identification of the Peptide binding Domain of hsc70," J. Biol. Chem. 268: 26049-26051 (1993).
Wilson et al., "Nuclear Import of Plasmid DNA in Digitonin-permeabilized Cells Requires Both Cytoplasmic Factors and Specific DNA . . . ," J. Biol. Chem. 274:22025-22032 (1999).
Zabner et al., "Cellular and Molecular Barriers to Gene Transfer by a Cationic Lipid," J. Biol. Chem. 270:18997-19007 (1995).
Hecker et al., "Nonviral Gene Delivery to the Lateral Ventricles in Rat Brain: Initial Evidence for Widespread . . . ," Molecular Therapy 3:375-384 (2001).
Niedzinski et al., "A Versatile Linker for Nontoxic Polyamine-Mediated DNA Transfection," Molecular Therapy 6:279-286 (2002).
Abdallah et al., "A Powerful Nonviral Vector for In Vivo Gene Transfer into the Adult Mammalian Brain: Polyethylenimine", Human Gene Therapy 7:1947-1954 (1996).
Alexander et al.,"Liposome-mediated gene transfer and expression via the skin," Human Molecular Genetics 4:2279-2285 (1995).
Anderson, "Human gene therapy," Nature 392:25-30 (1998).
Armstead et al., "Heat shock protein modulation of KATP and KCa channel cerebrovasodilation after brain injury," Am. J. Physiol. Heart Circ. Physiol. 289:H1184-H1190 (2005).
Aronsohn et al., "Nuclear Localization Signal Peptides Enhance Cationic Liposome-Mediated Gene Therapy," Journal of Drug Targeting 5:163-169 (1997).
Balasubramaniam et al., "Structural and functional analysis of cationic transfection lipids: the hydrophobic domain," Gene Therapy 3:163-172 (1996).
Barr et al., "Efficient catheter-mediated gene transfer into the heart using replication-defective adenovirus," Gene Therapy 1:51-58 (1994).
Bence et al.,"Impairment of the Ubiquitin-Proteasome System by Protein Aggregation," Science 292:1552-1555 (2001).
Bennett et al., "Cholesterol Enhances Cationic Liposome-Mediated DNA Transfection of Human Respiratory Epithelial Cells," Bioscience reports 15:47-53 (1995).
Bennet et al., "Considerations for the Design of Improved Cationic Amphiphile-Based Transfection Reagents," Journal of Liposome Research 6:545-565 (1996).
Bennett et al., "A Flexible Approach to Synthetic Lipid Ammonium Salts for Polynucleotide Transfection," Tetrahedron Letters 36:2207-2210 (1995).
Brooks et al., "TfxTM-20 Reagent and Gene Delivery into Mouse CNS," Neural Notes 4:20-23 (1998).
Duzgunes et al., "Intracellular Delivery of Nucleic Acids and Transcription Factors by Cationic Liposomes," Methods in Enzymology 221:303-306 (1993).
Dwarki et al., "Cationic Liposome-Mediated RNA Transfer," Methods in Enzymology 217:644-654 (1993).

(56) References Cited

OTHER PUBLICATIONS

Felgner et al., "Improved Cationic Lipid Formulations for In Vivo Gene Therapy," Annals New York Academy of Sciences 772:126-139 (1995).

Felgner et al., "Lipofection: A highly efficient, lipid-mediated DNA-transfection procedure," Proc. Natl. Acad. Sci. 84:7413-7417 (1987).

Felgner et al., "Cationic liposome-mediated transfection," Nature 337:387-388 (1989).

Fisher et al., "In vivo and ex vivo gene transfer to the brain," Current Opinion in Neurobiology 4:735-741 (1994).

Gallie et al., "Post-transcriptional regulation in higher eukaryotes: The role of the reporter gene in controlling expression," Mol. Gen. Genet. 228:258-264 (1991).

Hauck et al., "In-Vivo Time Course of Reporter Gene Expression after Nucleic Acid Delivery to the Lateral . . . ," Molecular Therapy vol. 11, Supplement 1, p. S224 (2005).

Hecker et al., "Distribution, expression, and inflammatory response after nonviral gene delivery . . . ," Neuroscience Abstract Archive (2005).

Hecker et al., "Distribution, Time Course, In-Vivo Imaging, Expression and Inflammatory Response after Non . . . ," Molecular Therapy vol. 11, Supplement 1, p. S223 (2005).

Hecker et al., "Non-Viral DNA and mRNA Gene Delivery to the CNS Pre-Operatively for Neuroprotection . . . ," Molecular Therapy vol. 9, Supplement 1, p. S258 (2004).

Hermens et al., "Transient gene transfer to neurons and glia: Analysis of adenoviral vector performances in the CNS and PNS," J. Neurosci. Methods 71:85-98 (1997).

Jacobs et al., "Spinal cord blood supply in patints with thoracoabdominal aortic abneurysms," J. Vasc. Surg. 35:30-37 (2002).

Jirikowski et al., "Reversal of Diabetes Insipidus in Brattleboro Rats: Intrahypothalamic injection of Vasopressin mRNA," Science 255:996-998 (1992).

Kajiwara et al., "Immune Responses to Adenoviral Vectors During Gene Transfer in the Brain," Human Gene Therapy 8:253-265 (1997).

Kaneda et al., "Increased Expression of DNA Cointroduced with Nuclear Protein in Adult Rat Liver," 243:375-378 (1989).

Kariko et al., "In vivo protein expression from mRNA delivered into adult rat brain," J. Neurosci. Methods 105:77-86 (2001).

Kiang et al., "Heat Shock Protein 70 kDa: Molecular Biology, Biochemistry, and Physiology," Pharmacol. Ther. 80:183-201 (1998).

Kofke et al., "S-100 and NSE Changes After Cardiac Surgery: Evaluation of Multiple Single Nucleotide Polymorphisms," Anesth. Analg. 102:1295-96 (2006).

Lawrence et al., "Inflammatory reponses and their impact on beta-galactosidase transgene expression following adenovirus vector delivery . . . ," Gene Therapy 6:1368-1379 (1999).

Malone et al., "Cationic liposome-mediated RNA transfection," Proc. Natl. Acad. Sci. USA 86:6077-6081 (1989).

Mannino et al., "Liposome Mediated Gene Transfer," Biotechniques 6:682-690 (1988).

McKinney et al., "Stretch-Induced Injury of Cultured Neuronal, Glial, and Endothelial Cells," Stroke 27:934-940 (1996).

Naldini et al., "In Vivo Gene Delivery and Stable Transduction of Nondividing Cells by a Lentiviral Vector," Science 272:263-267 (1996).

Pan et al., "Rat brain DNA transcript profile of halothane and isoflurane exposure," Pharmacogenetics and Genomics 16(3):171-182 (2006).

Papadopoulos et al., "Over-expression of HSP-70 protects astrocytes from combined oxygen-glucose deprivation," NeuroReport 7:429-432 (1996).

Rajapandi et al., "Characterization of D10S and K71E Mutants of Human Cytosolic Hsp70," Biochemistry 37:7244-7250 (1998).

Ravagnan et al., "Heat-shock protein 70 antagonizes apoptosis-inducing factor," Nature Cell Biology 3:839-843 (2001).

Ross, "Review—Messengar RNA Turnover in Eukaryotic Cells," Mol. Biol. Med. 5:1-14 (1988).

Schenborn et al., "TfxTM-50 Reagent: A New Transfection Reagent for Eukaryotic Cells," Promega Notes Magazine 52:2 (1995).

Schwartz et al., "Gene transfer by naked DNA into adult mouse brain," Gene Therapy 3:405-411 (1996).

Sharp et al., "Heat-shock protein protection," Trends in Neurosciences 22:97-99 (1999).

Shimohama et al., "Grafting genetically modified cells into the rat brain: characteristic of E. coli beta-galactosidase as a reporter gene," Mol. Brain Res. 5:271-278 (1989).

Snyder, "Adeno-Associated Virus-Mediated Gene Delivery," The Journal of Gene Medicine 1:166-175 (1999).

Sun et al., "The carboxyl-terminal domain of inducible Hsp70 protects from ischemic injury in vivo and in vitro," J. Cerebral Blood Flow & Metabolism 26:937-950 (2006).

Volloch et al., "ATPase activity of the heat shock protein Hsp72 is dispensable for its effects on dephosphorylation of stress kinase JNK . . . ," FEBS Letters 461:73-76 (1999).

Wangerek et al., "Atomic force microscopy imaging of DNA-cationic liposome complexes optimised for gene transfection into neuronal cells," J. Gene Medicine 3:72-81 (2001).

Xu et al., "Mechanism of DNA Release from Cationic Liposome/DNA Complexes Used in Cell Transfection," Biochemistry 35:5616-5623 (1996).

Xu et al., "HSP70 protects murine astrocytes from glucose deprivation injury," Neuroscience Letters 224:9-12 (1997).

Yang et al., "Overexpression of interleukin-1 receptor antagonist in the mouse brain reduces ischemic brain injury," Brain Research 751:181-188 (1997).

Yang et al., "Electrophysiological properties of identified postnatal rat hippocampal pyramidal neurons in primary culture," Dev. Brain Res. 71:19-26 (1993).

Yu et al., "Topical Gene Delivery to Murine Skin," J. Invest. Dermatol. 112 (3):370-375 (1999).

Zhu et al., "A continuous intracerebral gene delivery system for in vivo liposome-mediated gene therapy," Gene Therapy 3:472-476 (1996).

Zou et al., "Gene Delivery to Primary Neuronal Cells," Molecular Therapy vol. 11, Supplement 1, pp. S225-S226 (2005).

Zou et al., "Liposome-mediated NGF gene transfection following neuronal injury: potential therapeutic applicaitons," Gene Therapy 6:994-1005 (1999).

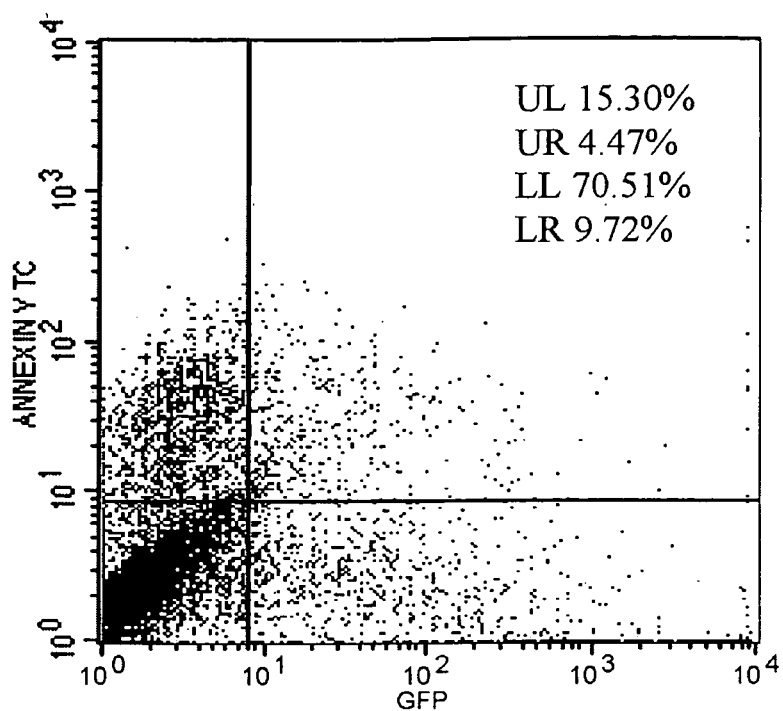
FIG. 1A DNA
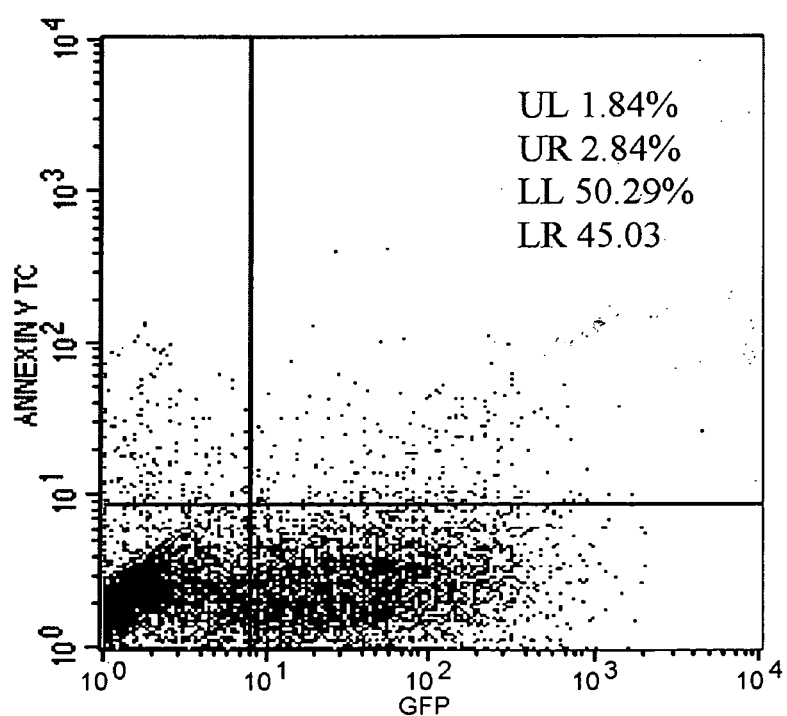
FIG. 1B RNA

METHODS AND MODELS FOR RAPID, WIDESPREAD DELIVERY OF GENETIC MATERIAL TO THE CNS USING NON-VIRAL, CATIONIC LIPID-MEDIATED VECTORS

FIELD OF THE INVENTION

The present invention relates to methods for safely treating disorders or diseases of the central nervous system ("CNS") by gene therapy, specifically rapid gene expression following delivery by non-viral, lipid mediated vectors, in vitro or in vivo, including clinical applications.

BACKGROUND OF THE INVENTION

Therapeutic treatments to the CNS necessarily require delivery of the requisite biological therapeutic to the target cells and organs to achieve physiologically significant expression levels without toxicity. Gene therapy has the potential, though largely still unrealized, to significantly advance clinical medicine. Long term expression after gene therapy is useful for diseases which require chronic levels of protein expression, such as inherited enzyme deficiencies. However, the risks and duration of gene delivery must also be closely matched to the proposed clinical application.

Gene therapy affecting the CNS has been the target of concentrated research efforts for many years. However, gene delivery and expression to the CNS has focused primarily on long term delivery methods using viral vectors. Nevertheless, while viral vector systems have been used to transfect cells in vitro and in vivo, they have not yet proven safe in a patient. For clinical applications in which only short-term gene expression is required or warranted, the delivery of nucleic acids by means of a non-viral cationic lipid may provide a more favorable risk/benefit analysis. Moreover, cationic lipid-mediated transfection advantageously offers low immunogenicity, ease of preparation, and the ability to transfect vectors of nearly unlimited size (Mountain, *Trends in Biotechnol.* 18:119-128 (2000)), as compared with the use of viral vectors. However, clinical trials using cationic lipids for delivery have primarily examined applications requiring brief expression of transgenes, such as therapies aimed at direct or immunological killing of tumor cells.

In proliferating cells, the majority of the DNA enters the nucleus through passive movement. This occurs during the nuclear membrane degradation stage of mitosis (Wilson et al., supra, 1995; Melchior et al., supra, 1998). However, the amount of DNA that is able to cross the nuclear envelope in non-proliferating cells by passive movement through the NPC has been assumed to be negligible (Aronsohn et al., supra, 1998), creating an additional barrier in the development of an efficient DNA delivery system (Bally et al., *Adv. Drug Deliv. Rev.* 38:291-315 (1999)); Girao da Cruz et al., *Biochim. Biophys. Acta* 1510:136-151 (2001)); Zabner et al., *J. Biol. Chem.* 270:18997-19007 (1995)). However, trials have not examined cationic lipid delivery methods of gene sequences in vivo for the rapid, transient expression of neuroprotective proteins in the central nervous system, or for attenuating cell death following CNS trauma.

The cerebral spinal fluid (CSF) is an effective way to express gene vectors in the brain. Rennels et al., *Brain Res.* 326:47-63 (1985)) proposed a rapid perivascular flux from CSF to the extracellular fluid to account for rapid fluid circulation throughout the CNS. Intra-ventricular injection in rats of an adenoviral vector for β-gal and IL-2 receptor antagonist (Betz et al., *J. Cerebral Blood Flow and Metabolism* 15:547-551 (1995); Yang et al., *Brain Res.* 751:181-188, (1997)) showed staining for f3-gal confined primarily to cells lining the ventricles. Despite this apparently limited expression, a reduction of stroke size in permanent focal ischemia was seen and the authors concluded that the ependyma does not form a barrier to movement of substances between CSF and brain.

Many investigators have demonstrated the use of viral vectors for transferring genes into various tissues, including into the CNS (Barr et al., *Gene Ther.* 1:51-58 (1994); Engelhardt et al., *Human Gene Ther.* 4:759-769 (1993); Hermens et al., *J. Neurosci. Meth.* 71:85-98 (1997); Shimohama et al., *Mol. Brain Res.* 5:271-278 (1989)). Leading viral vector systems include recombinant retrovirus (for replicating cells), adeno- (AV) and adeno-associated (AAV) virus, retroviral (RV), lentiviral, and herpes simplex virus vectors (HSV). For example, fetal myocytes (cardiac cells) that had been transfected with HSP70 using a viral vector were protected when subjected to simulated ischemia (Mestril et al., *J. Mol. Cell Cardiol.* 28:2351-2358 (1996)). Giffard et al. transfected astrocytes using a retroviral vector for HSP70 and reported protection of astrocytes and neurons from oxygen-glucose deprivation (Papadopoulos et al., *Neuroreport* 7:429-432 (1996)) in the same cell culture, even though only the astrocytes were transfected (Xu et al., *Soc Neurosci Abstracts* 23:845.1323:845.13 (Society for Neuroscience Annual Meeting, New Orleans, 1997)).

Viral vectors have also been used to protect the CNS by direct injection (Hermens et al., supra, 1997). Fink et al. used a herpes simplex vector to show improved neuron survival in a rat middle cerebral artery occlusion model (Yenari et al., *Soc. Neurosci. Abstracts* 23:547.12 (Society for Neuroscience Annual Meeting, New Orleans, 1997)), while the use of HSV to transfect non-dividing cells in the CNS has been reported by Naldini et al., *Science* 272:263-267 (1996)). Retroviral and HSV vectors (Geller et al., *Proc. Natl. Acad. Sci. USA* 87:1149-1153 (1990)) have been used in experimental trials for the treatment of human CNS tumors (Karpati et al., *Trends in Neurosciences* 19:49-54 (1996)), but none of these viral-based gene delivery methods teach how to safely deliver gene sequences for CNS neuroprotection without the risks of viral vectors.

Inherent risks associated with the use of a viral vector in a patient are known, and experimental use of such vectors has resulted in at least one well-publicized patient death secondary to liver failure after adenoviral gene therapy in 1999. Inflammation is a known complication resulting from the use of the common adenoviruses for viral gene therapy (Byrnes et al., *Neuroscience* 66:1015-1024 (1995); Kajiwara et al., *Human Gene Ther.* 8:253-265 (1997). An ineffective T-cell response in the brain may account for a prolonged response to adenoviral vectors in brain tissue (Byrnes et al., *Gene Ther.* 3:644-651 (1996)). An adenovirus expressing the herpes simplex thymidine kinase gene was tested in rats and primates in intracranial injections, but a dose dependent localized necrosis, mild gliosis, focal astrocytosis trace meningitis, and perivascular cuffing was described (Smith et al., *Human Gene Ther.* 8:943-954 (1997)). Undesirable persistence of defective HSV-1 vectors in rat brain has also been reported (Starr et al., *Gene Ther.* 3:615-623 (1996). Many other drawbacks, including production difficulties, have been reported. For example, in one issue alone of *Molecular Therapy*, the journal of the American Society for Gene Therapy, several articles reported that significant problems still remained with the use of viral vectors, including: oncogenesis following lentiviral fetal and neonatal murine delivery; inadvertent gene transfer to male germ-line cells following retroviral gene delivery; and encapsulation and in vivo persistence of prokaryotic sequences during the production of AAV vectors.

Moreover, although viral vectors can achieve transduction, producing extremely high levels of protein expression, such high levels of expression and infectivity may be more than is needed to be of physiologic significance in vivo, even if they could be routinely achieved. Viral vectors may, in fact, overwhelm the cellular protein producing apparatus of the cell in vivo (Peltekian et al., *J. Neurosci. Meth.* 71:77-84 (1997). Despite the recognized deficiencies associated with the use of viral vectors to deliver the gene sequences, the literature also fails to teach how to avoid significant inflammatory and/or immune responses. Indeed, there are no reports of non-viral, rapid, widespread CNS transfection without the requirement of craniotomy or burr holes in the skull, followed by injection into brain or lateral ventricle.

In an attempt to overcome the problems associated with viral delivery, researchers have proposed a number of non-viral methods for delivering polynucleotides into neuronal cells and tissues. Calcium precipitation and electroporation are of extremely limited usefulness in vivo in the CNS. Jiao et al., *Biotechnology* 11:497-502 (1993) bombarded fetal brain tissue with DNA that had been precipitated onto gold pellets (the Accell device) and demonstrated transfection of isolated neuron and glial cells. Biewenga et al., *J. Neurosci. Meth.* 71:67-75 (1997) reviewed the specific parameters of the use of biolistics ("gene gun") to transfect neurons in culture. Naked DNA can be transfected into skin (Yu et al., *J. Invest. Dermatol.* 112:370-375 (1999)) and high ionic strength carriers, such as liposomes, can be used to augment the low baseline efficiency and durability of gene expression in this tissue setting (Chesnoy et al., *Mol. Ther.* 5:57-62 (2002); Alexander et al., *Human Mol. Genet.* 1995; 4: 2279-2285 (1995)). However, there are few reports in the literature of widespread expression in CNS using non-viral methods, particularly methods with the potential for clinical usefulness and none are non-invasive. See, e.g., Zhu et al., *Gene Ther.* 3:472-476 (1996), who reported use of cationic lipid mediated gene transfer of the herpes simplex virus thymidine kinase (tk) gene into glioma tumor cells in vivo in rats, using a continuous infusion pump. However, such non-viral methods involve direct injection into the brain, requiring a surgical procedure (brain surgery) prior to injection Cationic lipid-mediated gene transfer is particularly suited for transient gene expression, both in basic research and in selected clinical applications. Cationic lipids are used to protect plasmid DNA from DNAse I digestion, from endogenous DNAses in the extracellular environment and CSF (Luo et al., *Nature Biotechnology* 18:33-37 (2000)). Hundreds of clinical gene therapy trials have been completed or remain currently in progress (updated at J. Gene Medicine Web site at http://www.wiley.co.uk/genetherapy), mainly for the treatment of melanoma, head and neck, and ovarian cancer. At least 22% of the reported human clinical protocols are either non-viral lipid-mediated, or utilize non-viral DNA delivery. Thus, the safety of non-viral mediated gene transfer is no longer an issue, and cationic lipid-mediated gene delivery avoids many of the potential objections to the use of viral DNA vectors. Moreover, the results normally reflect a dramatic improvement over therapies using naked DNA delivery.

Cationic lipids commonly have a polar head group and non-polar symmetric or dissymmetric carbon based (fatty acid) tail, which gives membrane fluidity to the lipoplex. Negatively charged nucleic acids condense and self-assemble into heterogeneous complexes of lipids and nucleic acids when mixed with cationic lipids (Feigner et al., *Annals NY Acad. Sci.* 772:1126-1139 (1995)). The structure and size of these complexes affect transfection efficacy and vary with temperature, concentration, charge ratio, buffer, time, and lipid composition. Numerous laboratories (e.g., Feigner et al., *Proc. Nat'l. Acad. Sci. USA* 84:7413-7437 (1987); Byk et al., *Drug Develop. Res.* 50:566-572 (2000); Niedzinski et al., *Mol. Ther.* 6: 279-286, 2002)) have investigated the limiting parameters of cationic lipid-mediated transfection with the goal of improving transfection efficiency.

While cationic lipid-mediated delivery is useful for delivery of nucleic acids, either mRNA or DNA, see Feigner et al., supra, 1987), transfection of primary cell lines (including for neuronal and glial cells of the CNS) remains a problem (Wangerek et al., *J. Gene Med.* 3:72-81 (2001)). There are four general barriers to lipid-mediated DNA transfection: 1) transport of the nucleic acid/lipid complex in the extracellular environment; 2) association and uptake of the nucleic acid/lipid complex by the target cell (Bally et al., supra, 1999); Feigner et al., supra, 1995); 3) intracellular DNA release from the nucleic acid/lipid complex (Girao da Cruz et al., supra, 2001); and 4) translocation of DNA to the nucleus (Mortimer et al., *Gene Therapy* 6:403-411 (1999)). The primary barrier to DNA transfections in post mitotic cells is assumed to be DNA translocation to the nucleus (Zabner et al., supra, 1995).

Neuronal cells are regarded as particularly difficult to transfect with non-viral techniques, although adenovirus or HSV have met with some success in the CNS (Krisky et al., *Gene Therapy* 5:1593-1603 (1998)). This difficulty is generally attributed to markedly reduced or absent mitotic activity (Wangerek et al., supra, 2001). In proliferating cells, nuclear translocation is mainly passive, occurring during mitosis as the nuclear membrane breaks-down (Bally et al, supra, 1999; Wilke et al., *Gene Therapy* 3:1133-1342 (1996); Nicolau et al., *Biochim. Biophys. Acta* 721:185-190 (1982)). Some nuclear translocation also occurs in non-proliferating cells, probably as a result of passive movement through the nuclear pore complex (NPC) (Mattaj et al., *Ann. Rev. Biochem.* 67:265-306 (1998); Wilson et al., *J. Biol. Chem.* 270:22025-22032 (1995)). To improve efficiency of lipid-mediated DNA transfer some investigators have used nuclear localization sequences (NLS) (Aronsohn et al., *J. Drug Targeting* 5:163-169 (1998); Melchior et al., *Trends Cell. Biol.* 8:175-179 (1998)) to target the non-proliferating cells, and thus to facilitate DNA entry into the nucleus.

Methods for otherwise avoiding the necessity of nuclear translocation of DNA have also been reported, such as delivery of T7 promoter DNA plasmid systems to T7 polymerase expressing cells (Brisson et al., *Human Gene Therapy* 10:2601-2613 (1999)). However, the T7 system is not useful in most basic research or clinical applications. Lipid-mediated RNA delivery to proliferating cells (Malone et al., *Proc. Nat'l. Acad. Sci. USA* 86:6077-6081 (1989)), as well as intramuscular injection of naked RNA has been previously described (Wolff et al., *Science* 247:1465-1468 (1990)). Jirikowski et al., *Science* 255:996-998 (1992)) reported the uptake of mRNA in vivo by neurons, following direct injection in the rat hypothalamus to correct diabetes insipidus. Kariko et al., *J. Neurosci. Meth.* 105:77-86 (2001)) demonstrated local expression by in situ and immunocytochemical techniques after injection of RNA complexed with lipofectin (Gibco/BRL) into brain parenchyma. There is also evidence that, at least, some mRNAs may be actively taken up by neural tissue and transported throughout the CNS (Mohr et al., *EMBO J.* 10:2419-2424 (1991)). However, none of these reports describe methods for rapid and widespread, rapid gene expression in the CNS after delivery of mRNA vectors into the CNS.

The leading non-viral gene therapy method involves the use of mRNA or DNA as a lipid/nucleic acid complex ("lipoplex"), with or without membrane proteins to provide targeting specificity. See, U.S. Pat. Nos. 5,869,715; 5,925,623; 5,824,812, (each by Nantz et al.), and related publications. Hecker et al., *Molecular Therapy* 3:375-384 (2001) described DNA expression using lipoplexes, and the methods described in the 2001 were used by Anderson et al., *Human Gene Therapy* 14(3):191-202 (2003) to examine the functional integrity and protection from degradation of mRNA/cationic complexes (lipoplexes) for more than 4 hours in human cerebrospinal fluid (hCSF) in vitro (as compared with rapid <5 min disappearance of non-lipid-complexed mRNA), and preliminary findings regarding expression of these lipoplexes in vivo (in vitro transcribed mRNA vectors encoding Hsp70 and luciferase were delivered to the lateral ventricle of brains of rat models). Expression was noted in coronal sections throughout the rat brain, confirming the potential for lipid-mediated mRNA delivery to the CNS. However, these publications demonstrated results only in the rat brain, and only following direct injection into the lateral ventricle of the rat brain. No evidence was reported indicating success in a non-human primate model or in higher order intact animals, or suggesting the possibility that intrathecal delivery to the CSF would be effective in humans.

A common problem associated with non-viral nucleic acid delivery techniques is that the amount of exogenous protein expression produced relative to the amount of exogenous nucleic acid administered remains too low for most diagnostic or therapeutic procedures. Low levels of protein expression are often a result of a low rate of transfection of the nucleic acid or the instability of the nucleic acid. As a result, despite numerous research efforts directed at finding efficient methods for nucleic acid delivery, most known techniques have failed to provide sufficient cell transfection to achieve the desired protein expression to be of clinical value. While prior art publications have shown rapid uptake, distribution, and expression of exogenous DNA and mRNA in the rat brain using GFP and luciferase reporter gene sequences, the current literature offers no non-invasive method for achieving rapid and extensive gene expression in the brains of human patients or primate models via cerebrospinal fluid administration free from the inherent risks and difficulties associated with the use of viral vectors. For example, although Schwartz et al., *Gene Therapy* 3:405-411 (1996) described modest expression of the reporter gene enzymes luciferase and β-galactosidase in rat brain after direct injection of up to 150 μg of DNA plasmid, they reported no additional efficacy using several standard cationic lipids, and their peak in enzyme assay signal was not reached until 48 hours post-administration. Primates have more robust and versatile immunological responses.

Heat shock proteins (HSP) are members of a highly conserved family of molecular chaperones that play important roles in normal cellular function and survival. They act as molecular chaperones expressed constitutively and rapidly induced in response to various types of stress, including heat shock, ischemia, oxidative stress, glucose deprivation, and exposure to toxins and heavy metals (Kiang et al., *Pharmacol. Ther.* 80:183-201 (1998)). The Hsp70 gene encodes a 44 kDa amino terminal ATPase domain, and a carboxyl terminal domain that contains the 18 kDa peptide or substrate binding domain followed by a 10 kDa stretch terminating in the highly conserved EEVD sequence (O'Brien et al., *J. Biol. Chem.* 271:15874-15878 (1996); Ohno et al., *FEBS Lett.* 576:381-386 (2004); Rajapandi et al., *Biochem.* 37:7244-7250 (1998); Wang et al., *J. Biol. Chem.* 268:26049-26051 (1993)).

Whole animals, isolated organs and cells subjected to heat shock are protected against a subsequent near lethal ischemic or hypoxic event. For example, Fink et al. transfected hippocampal neurons with the Hsp70 gene using a HSV vector to show improved neuron survival in a rat MCA occlusion model, and demonstrated what the authors described as "the first published report of protection following heat shock protein transfection in CNS neurons" (Fink et al., *J. Neurochemistry* 68:961-969 (1997)).

More recently, studies have shown that Hsp70 overexpression protects cells from death induced by various insults that cause either necrosis or apoptosis, including near lethal hypoxia and ischemia/reperfusion, by inhibiting multiple cell death pathways (Giffard et al., *J. Neurosurg. Anesthesiol.* 16:53-61 (2004); Steel et al., *J. Biol. Chem.* 279:51490-51499 (2004)). The induction of protective intracellular responses ("endogenous") by heat shock is not clinically useful, but the enforced overexpression with viral vectors, as a transgene, or pharmacological induction of Hsp70, all decrease injury after cerebral ischemia and protect both neurons and glia (Giffard et al., *J. Exp. Biol.* 207:3213-3220 (2004); Hoehn et al., *J. Cerebral Blood Flow Metab.* 21:1303-1309 (2001); Lu et al., *J. Neurochem.* 81:355-364 (2002); Rajdev et al., *Ann. Neurol.* 47:782-791 (2000)). Nevertheless, the ability of Hsp70 to provide neuroprotection has only been demonstrated in limited viral models on rodent species, but, to date, it has not been reported in non-human primates or in humans.

It has been previously reported that astrocytes expressing elevated levels of inducible Hsp70 are protected from oxygen-glucose deprivation (OGD), hydrogen peroxide ($H_2O_2$) exposure, and hyperthermic insult (Papadopoulos et al., *Neuroreport* 7:429-432 (1996); Xu et al., *Biochemistry* 35:5616-5623 (1996); Xu et al., *Neurosci Lett.* 224:9-12 (1997)). However, it was not clear whether the protective effect of Hsp70 was caused by direct interaction with misfolded protein or, whether it resulted from the anti-apoptotic and anti-necrotic effects of Hsp70. Sun et al., *J. Cerebral Blood Flow and Metabolism,* 26(7):937-950 (July 2006) (Epublished November 2005), using two mutants of Hsp70, confirmed the importance of protein folding to ischemic protection, and showed that the peptide binding domain of Hsp70 was sufficient for protecting cells from ischemia in vitro (primary astrocyte culture) and in vivo (reduced infarct size and focal ischemic injury as induced by transient middle cerebral artery occlusion, and improve neurological function). These results are consistent with prior reports showing that a deletion mutant, containing the peptide binding domain of Hsp70, but lacking the ATPase domain, is still capable of protecting cells from heat (Li et al., *J. Biol. Chem.* 275:25665-25671 (1992)), serum withdrawal (Ravagnan et al., supra, 2001) and heat-stress induced apoptosis (Volloch et al., *FEBS Lett.* 461:73-76 (1999)). Thus, the significant protective effect of the mutants suggest that peptides, such as Hsp70, specifically the carboxyl-terminal domain of Hsp70, could offer a useful therapeutic strategy for the treatment of stroke and neurodegenerative diseases if safely delivered to the target CNS.

In addition, there is strong evidence that Hsp70 can protect cells from toxicity due to misfolded, aggregated proteins associated with neurodegenerative diseases (Dong et al. *Molecular Therapy* 11:80-88 (2005); Muchowski et al., *Nat. Rev. Neurosci.* 6:11-22 (2005); Tidwell et al., *Cell Stress Chaperones* 9:88-98 (2004)). For example, overexpression of Hsp70 suppressed degeneration and improves motor function in a transgenic mouse model of SCA1 (Cummings et al., *Hum. Mol. Genet.* 10:1511-1518 (2001)). Similarly, the overexpression of Hsp70 reduces the toxicity of mutant α-synuclein in Parkinson's disease (Auluck et al., *Science* 295:865-868 (2002)).

It is evident from the prior art that HSP70 offers great potential as a neuroprotectant before injury, and as a therapeutic solution immediately after CNS or spinal cord injury, if it can be safely delivered to the site and cells where it is needed. However, the reported induction of protective intracellular responses by heat shock proteins is not clinically useful because delivery via a viral vector carries the inherent risks to the patient, and because rapid and widespread distribution that is required for use of the protective HSP gene sequences has not been provided. Sun et al. supra, 2005 provide valuable insight into possible, albeit unproven, mechanisms by which HSP70 may be effective, but no prior art publication has taught how to integrate all of the necessary knowledge, including formulation, synthesis, packaging, delivery, efficacy, safety and methodology to successfully administer therapeutic or preventative compounds to the human CNS. Thus, until the present invention, a need has remained in the art for non-viral, lipid mediated methods, that do not involve surgical intervention needed for direct injection to the brain, for a safe, short-term delivery of nucleic acids, particularly mRNA, encoding therapeutic proteins, e.g., HSP, to cells of the CNS, and for the rapid expression and widespread distribution of the therapeutic proteins for in vitro or in vivo applications, including clinical use. Such methods could promote, for example, nervous system cell repair and regeneration in vivo, and/or prevent or decrease the severity of ischemic damage due to, e.g., spinal and/or brain injury, including damage during surgery.

SUMMARY OF THE INVENTION

The present invention provides non-viral-based delivery methods, thereby meeting the foregoing need for a safe, non-viral method for the lipid-mediated, controlled delivery of nucleic acids encoding therapeutic proteins to non-proliferating cells of the CNS, specifically for their rapid expression and widespread distribution for in vitro or in vivo applications. Moreover, no brain surgery is involved in the present methods because the protected nucleic acids are non-invasively delivered via the CSF. Further, the invention offers the first comparative analysis of cationic lipid-mediated RNA versus DNA gene delivery in proliferation-inhibited cells and primary mixed neuronal cultures. The present invention demonstrates extensive PCR DNA copy number results in the CNS of the non-human primate, providing critical in vivo DNA and mRNA time course expression data in the intact animal for pre-clinical therapeutic dosing schedules, thus demonstrating in a primate model of human activity, the effectiveness of intrathecal delivery to the CSF of a neuroprotective gene sequence (HSP70), and the necessary cationic lipid compositions, including PMDI, to safely achieve such delivery. PMDI is disclosed by Nantz et al., U.S. Pat. No. 5,869,715.

This study is unique in that it directly tests the importance of mitosis in the efficiency of the lipid-mediated delivery of RNA and DNA vectors in proliferation-inhibited CHO cells, proliferation-inhibited NIH 3T3 fibroblasts, and in primary neuronal cultures, while explicitly testing the hypothesis that RNA vector delivery is more efficient than DNA vector delivery. The findings demonstrate that RNA is 2 to 5 times more efficient than DNA for inducing rapid, transient and controllable gene expression for CNS neuroprotection and therapy, when based on the percentage of cells transfected, as measured by flow cytometry.

Thus, it is an object of the invention to provide transient gene delivery to the CNS to induce rapid, transient and controllable gene expression for CNS neuroprotection and therapy in patients who are at risk of primary or secondary CNS injury as a result of neurosurgical resection, cardiac bypass procedures, circulation arrested surgical procedures, traumatic brain or spinal cord injury, or stroke.

An mRNA alone or in combination with DNA is well-suited for clinical peri-operative use. Thus, in an embodiment of the invention, peak expression is shown, by both in vivo imaging and by immunohistochemistry, as early as 1 hour, peaking at 5-6 hours, after injection/infusion of mRNA lipoplex to intracerebral ventricle, cisterna magna, or intra brain parenchyma in the brains of various model animals. Moreover, the expression dissipates within 12-24 hours after termination of the infusion. Thus, it is an object of the invention to provide GFP, luciferase and β-galactosidase reporter gene comparisons, permitting both mRNA and DNA vectors to be systematically evaluated for non-viral gene delivery for clinical use, and rapid and widespread gene expression was achieved as a result of controlled, transient delivery to the cerebrospinal fluid (CSF) of the unique non-viral, lipid-mediated formulations ("lipoplexes") of mRNA of the present invention.

The CSF circulation was examined to demonstrate widespread gene expression using the unique formulation of lipids, vectors, and incubation conditions of the present invention to produce embodiments that are protected in the extracellular and intracellular environments, transported in a widespread manner throughout the CNS by bulk transport mechanisms in the CSF, taken up by and across biological membranes, and presented to the intracellular trafficking machinery for efficient transcription and translation (DNA) or translation (mRNA). The resulting novel findings are in direct contrast to existing prior art, and are in particular applied to deliver highly inducible members of the Hsp70 family to express candidate therapeutic formulations in the CNS for purposes of neuroprotection.

Consequently, data shows that non-viral delivery of gene sequences of inducible Hsp70 is protective of the CNS, both in terms of infarct size and in animal behavior, in a model species, establishing that the present methods, formulations, and techniques can be used with any gene sequence to offer neuroprotection, either pre- or intra-operative (peri-operative), or immediately after stroke, traumatic brain injury ("TBI"), or spinal cord injury ("SCI").

It is an object of the invention to provide methods for delivering a polypeptide to a CNS cell by delivery of nucleic acid, particularly RNA, to provide transient expression of the encoded polypeptide. Of particular interest is delivery of nucleic acid (particularly RNA) to the CNS by administration to the cerebrospinal fluid or the parenchyma of the brain. In specific embodiments, the invention relates to transient expression and delivery of a neuroprotective protein, such as a heat shock protein (HSP) to provide protection against stress and injury. Thus, in one embodiment, the invention provides for pre-operative protection of CNS cells. When the invention provides RNA-based delivery methods, the invention avoids many of the undesirable features of DNA-based vectors, such as the problems of transcriptional control, as well as the possibility of permanent DNA incorporation into the host cell genome, and it advantageously permits controllable transient production of the polypeptide of interest, allowing for better dose control of the therapeutic polypeptide.

In one aspect, the invention features a method for transient delivery of a polypeptide to a CNS cell, the method comprising administering of a formulation to a CNS cell of a mammalian host, the formulation comprising a nucleic acid (e.g., DNA or RNA) and a cationic lipid comprising at least one cationic lipid, wherein the nucleic acid encodes a polypeptide for expression in the CNS cell, and wherein the formulation is administered in an amount sufficient to provide transient expression of the encoded polypeptide in the CNS cell, and transient delivery of the polypeptide to the CNS cell. In certain embodiments, the cationic lipid and nucleic acid can form a liposome. In specific embodiments, the nucleic acid: cationic lipid formulation is delivered by administration to the CSF.

In another aspect, the invention features a method for protecting a central nervous system cell from ischemic injury, the method comprising administering a formulation to a CNS cell of a mammalian host, the formulation comprising a nucleic acid (e.g., RNA) and at least one cationic lipid, wherein the nucleic acid encodes a neuroprotective protein for expression in the cell, and wherein the formulation is administered in an amount sufficient to effect the expression of the encoded polypeptide in the CNS cell at a level sufficient to at least partially protect the CNS cell from ischemic injury. As above, in specific embodiments, the neuroprotective protein is a heat shock protein. In certain embodiments, the cationic lipid and nucleic acid form a liposome. In specific embodiments, the nucleic acid:cationic lipid formulation is delivered by administration to the CSF. This aspect of the invention offers great advantages to the patient and to the effectiveness of the delivery method because the nucleic acid can now be delivered via the CSF, distinguishing the present invention from delivery by methods of direct injection into brain or lateral ventricle, which require a craniotomy, i.e., brain surgery and all of the risks and problems associated with such surgery.

In another aspect, the invention features a method for improving recovery time of CNS cells following injury or preventing or mitigating injury related to surgical intervention, the method comprising administering the above-described formulation to a CNS cell of a mammalian host prior to, during, or after surgery, thereby effecting expression of the encoded polypeptide in the CNS cell at a level sufficient to improve recovery time of the CNS cell from injury, including surgical injuries, or to prevent or mitigate surgical injury. As above, in specific embodiments, the neuroprotective protein is a heat shock protein. In certain embodiments, the cationic lipid and nucleic acid form a liposome. In specific embodiments, the nucleic acid:cationic lipid formulation is delivered by administration to the CSF.

It is a further object of the invention to provide methods and compositions to deliver a polypeptide of interest, particularly a neuroprotective polypeptide, to CNS cells, or to deliver a nucleic acid encoding such polypeptide of interest, and cause its expression in the CNS cells. In particular, it is another object of the invention to provide for transient production of a polypeptide of interest in CNS cells, or to cause it to be expressed from a nucleic acid encoding same, which is delivered to the CNS cells.

One advantage of the invention is that delivery of nucleic acid to the CSF provides for widespread, but transient, dissemination of the nucleic acid to uptake and expression by CNS cells. Kits may be further provided to facilitate transient delivery of nucleic acids by non-viral vectors to the CNS.

Additional objects, advantages and novel features of the invention will be set forth in part in the description, examples and figures which follow, and in part will become apparent to those skilled in the art on examination of the following, or may be learned by practice of the invention.

BRIEF DESCRIPTION OF THE DRAWINGS

FIGS. 1A and 1B are scatter plots of FACScan analysis of GFP expression following cationic lipid-mediated DNA (FIG. 1A) and RNA (FIG. 1B) transfection in proliferation-inhibited CHO cells, showing an approximate 4-fold increase in the % of cells transfected by GFP RNA, relative to GFP DNA. Maximum % of GFP-expressing cells represents 12 hours and 48 hours post-transfection time points for mRNA and DNA, respectively.

FIG. 5A, shown at a magnification of 10× (20×), demonstrates widespread expression in rat cortex and subcortex after DAB immunohistochemistry. FIG. 5B, also shown at 10×, demonstrates widespread subcortical expression. FIG. 5C depicts an area of FIG. 5B, see inset, at a magnification of 40×, in which cells that are phenotypically neurons are visible. FIG. 5D depicts a section adjacent to that shown in FIGS. 5B and 5C, stained simultaneously, using identical methods, in which the primary antibody has been omitted (negative control).

DETAILED DESCRIPTION OF CERTAIN EMBODIMENTS OF THE INVENTION

Figure 2:
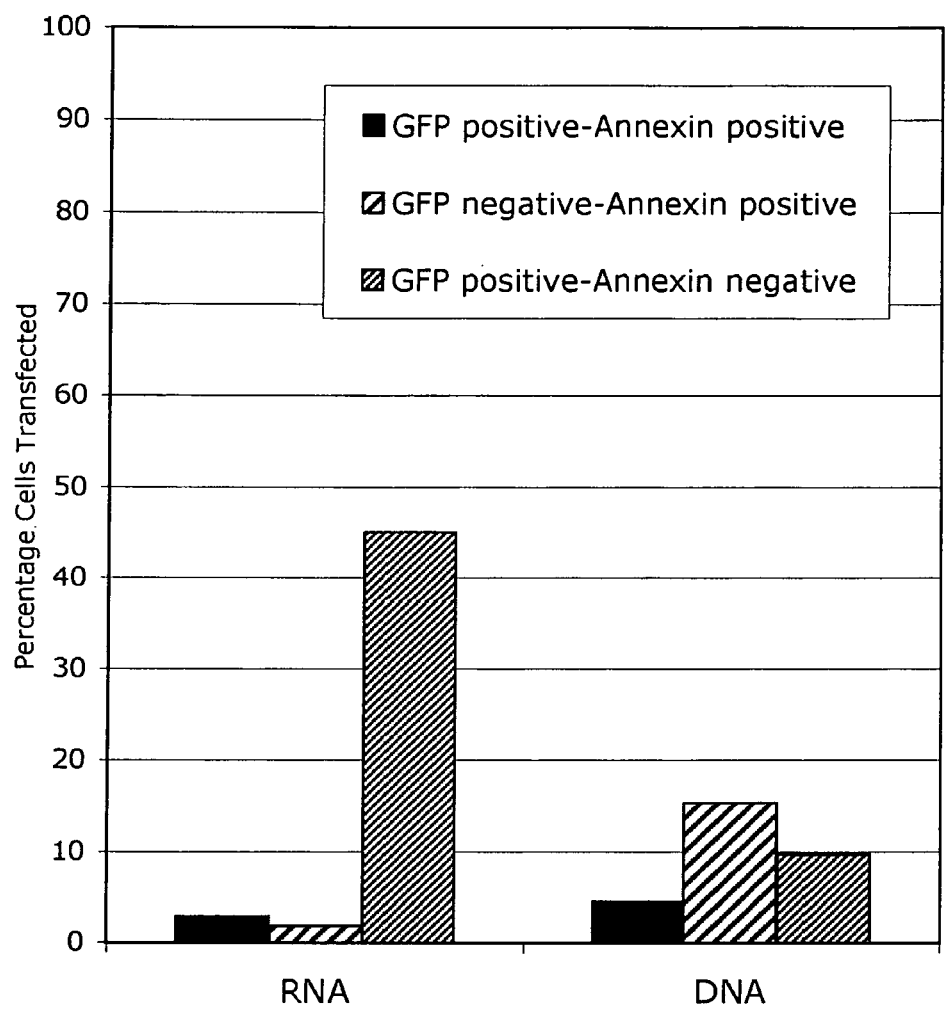
FIG. 2 is a graphical analysis of the FACScan analysis of cationic lipid-mediated RNA and DNA transfection in proliferation-inhibited CHO cells, showing the increase in the % of cells transfected by GFP RNA, relative to GFP DNA. Maximum % of GFP-expressing cells represents 12 hours and 48 hours post transfection time points for mRNA and DNA, respectively, as above.

The invention is based on the discovery that nucleic acid (RNA or DNA) complexed with a lipid-based carrier can be delivered to cells of the central nervous system ("CNS") or brain parenchyma to provide for controllable transient expression of the polypeptide encoded by the delivered nucleic acid. In particular, the cerebrospinal fluid ("CSF") can be used as a carrier medium to accomplish widespread distribution to cells of the central nervous system (CNS), including neurons and cells of the brain. This discovery can be exploited to accomplish delivery of any protein of interest for production in the CNS. In certain embodiments of particular interest, RNA encoding a neuroprotective protein, such as a heat shock protein (e.g., Hsp70) can be delivered to the CNS to confer protection against later ischemia, e.g., to provide for pre-operative protection of CNS cells. The embodied non-viral, lipid-mediated nucleic acid vector formulations are significantly safer than viral based systems, particularly for pre- or intra-operative use, or for administration during or immediately after stroke, TBI, or SCI.

As used herein, "lipoplex" (also used interchangeable with "lipid complex" or "lipid:vector complex") refers to a heterogeneous complex, which self-assembles when nucleic acids are mixed with cationic lipids (see Feigner et al., supra, 1995). Cationic lipids suitable for lipid/nucleic acid complexes ("lipoplexes") have been designed by Nantz (U.S. Pat. Nos. 5,869,715; 5,925,623; 5,824,812, and related publications, each of which is herein incorporated by reference, and have been tested for delivery of nucleic acids to neural cells by Hecker et al., supra, 2001; and Anderson et al., supra, 2003, also incorporated by reference. Transfection efficacy of the lipoplex has been found to be affected by structure and size, and varies with, e.g., temperature, concentration, charge ratio, buffer, time, and lipid composition. Degradation and/or aggregation of nucleic acids in the extracellular environment, cellular targeting and uptake of the lipoplex, and release of the nucleic acid sequence from the lipoplex have been recognized as major barriers to lipid-mediated transfection.

In the present invention, however, lipoplex formulations are optimized and shown to stabilize the nucleic acids against degrading enzymes from the extracellular environment. As shown, the delivery of mRNA sequences permits rapid expression of a sufficient amount of the encoded therapeutic protein to the targeted cells to achieve clinical protection or mediation of injury to a patient, particularly as a result of ischemia. The short duration of expression with mRNA transfection is an advantage in certain clinical situations, including pre-treatment of tissues at risk for ischemic damage or for immediate delivery after stroke or CNS trauma to minimize secondary injury. Moreover, GFP and luciferase reporter gene expression has been shown to be more rapidly detected following mRNA transfection, as compared with DNA transfection complexes (Malone et al., *Proc. Nat'l. Acad. Sci. USA* 86:6077-6081 (1989); Hecker et al., *Anesth. Anal.* 84:S360, 1997; Keogh et al., *Gene Ther.* 4:162-171 (1997)).

As used herein, terms are intended to have their ordinary meanings as recognized in the art, unless expressly described as having a different meaning herein. Reference to "a cell" includes a plurality of cells, reference to "a polynucleotide" includes reference to one or more polynucleotides and equivalents thereof known to those skilled in the art, and the like.

Nucleic Acids, Vectors and Therapeutic or Neuroprotective Protein Expression Products Gene delivery to and expression in non-mitotic cells is essential to the development of gene therapy strategies in the CNS. Although viral methods have been used for some indications, safety issues do not make the routine use of viral transfection optimal or appropriate for many clinical applications (Byk et al., supra, 2000). Cationic lipids are an alternative to viral based gene therapy. Currently, about a quarter of all clinical trials involve non-viral methods, including ~17% using naked/plasmid DNA and ~8.3% utilizing cationic lipid-mediated delivery (see, http://www.wiley.co.uk/genetherapy/2006).

Systemic infusion to blood plasma has proven to be a difficult medium for gene delivery, because transfection complexes aggregate extensively with polyanionic molecules (Plank et al., *Human Gene Therapy* 7:1437-1446 (1996); Tros de Ilarduya et al., *Biochim. Biophys. Acta* 1463:333-342 (2000)) and are rapidly cleared from the circulation. Thus, the alternative methods of the present invention are required for delivery of therapeutic or protective proteins, or the nucleic acids encoding protein expression products, in the neural cells of the CNS and brain. Specifically, the non-viral lipid-mediated gene transfer, by the methods of the present invention, to the CNS by cerebrospinal fluid (CSF) delivery avoids many of the difficulties associated with intravascular delivery.

The terms "polynucleotide" and "nucleic acid," used interchangeably herein, refer to polymeric forms of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. As used herein "RNA" or "RNA encoding a polypeptide" generally refers to, but is not necessarily limited to, messenger RNA ("mRNA") when associated with rapid, short-term expression.

The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits, such as phosphoramidites and thus can be an oligodeoxynucleoside phosphoramidate or a mixed phosphoramidate-phosphodiester oligomer (Peyrottes et al., *Nucl. Acids Res.* 24:1841-1848 (1996); Chaturvedi et al., *Nucl. Acids Res.* 24:2318-2323 (1996)). A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are, without intended limitation, caps, substitution by an analog of one or more of the naturally occurring nucleotides, and introduction of means for attaching the polynucleotide to proteins, metal ions, labeling components, additional polynucleotides (natural or synthetic) or a solid support.

As used herein, the term "neuroprotective gene" refers to a gene or coding region that encodes a protein, polypeptide or peptide that promotes or assists in promoting a protective effect, e.g., provides for protection against injury or damaging effects of, e.g., ischemia. Cells of the central nervous system (CNS) have a high metabolic rate, requiring continuous delivery of glucose and oxygen for optimal function. The cells have no capacity to store fuel reserves. Accordingly, CNS tissue is particularly vulnerable to damage (or death) when cut off from its supply line by an acute ischemic or hypoxic event (for example, as occurs during a stroke). The stress response proteins are known to be induced by such events, and are neuroprotective when present in the intracellular environment of nervous system tissue. Thus, a neuroprotective polypeptide is one that, when expressed, provides protection of the cell against injury, damage or insult, regardless of the cause.

As known to those of skill in the art, the original source of a recombinant nucleic acid to be used in a therapeutic regimen need not be of the same species as the animal to be treated. Moreover, they may be synthetically produced. Consequently, it is contemplated that nucleic acid (RNA or DNA) encoding any neuroprotective polypeptide may be employed to provide protection of CNS cells in a human subject or an animal, domestic or wild type, such as, e.g., mammals, including dogs, horses, cats, and the like. Particularly useful polypeptides are those from humans or may be used to treat humans.

Methods for preparing a nucleic acid encoding a neuroprotective polypeptide are provided by the teachings disclosed herein, and include publications referenced herein, and methods known to those of ordinary skill in the art. A neuroprotective gene can be obtained or isolated using molecular biological techniques, such as polymerase chain reaction (PCR) or screening a cDNA or genomic library, as well as using primers or probes with sequences based on the above nucleotide sequences. The practice of such cloning, isolation or screening techniques for isolating a nucleic acid is routine for those of skill in the art, as taught in various scientific articles, such as Sambrook et al., *Molecular Cloning: A Laboratory Manual*, Cold Spring Harbor Laboratory Press, Cold Spring Harbor, N.Y. (2001); Ausubel et al., *Current Protocols in Molecular Biology*, John Wiley & Sons, New York (1997); and Gerhardt et al., eds., *Methods for General and Molecular Bacteriology*, American Society for Microbiology, Washington, D.C. (1994), each of which is incorporated herein by reference. Techniques for introducing changes in nucleotide sequences that are designed to alter the functional properties of the encoded proteins or polypeptides are well known in the art. Such modifications include the deletion, insertion or substitution of bases, and thus, changes in the amino acid sequence. Changes may be made to increase the neuroprotective activity of a protein, to increase its biological stability or half-life, to change its glycosylation pattern, and the like. All such modifications to the nucleotide sequences are encompassed by this invention.

In cells of higher organisms (eukaryotes), the chromosomes (DNA) are located within the nucleus, but protein synthesis takes place in the cytoplasm, which is physically separated from the nucleus by the nuclear membrane. The process of reading from DNA to mRNA is termed transcription, whereas the process of building a polypeptide from the mRNA message is translation.

An "isolated nucleic acid" refers to a nucleic acid segment or fragment which has been separated from sequences which flank it in a naturally occurring state, e.g., an RNA or DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA, DNA or proteins, which naturally accompany it in the cell, and refers to compounds that are within samples that are substantially enriched for the compound of interest and/or in which the compound of interest is partially or substantially purified. The term, therefore, includes, e.g., recombinant DNA which is incorporated into a vector, into an autonomously replicating plasmid or virus, or into the genomic DNA of a prokaryote or eukaryote, or which exists as a separate molecule (e.g., as a cDNA, or a genomic, or cDNA fragment produced by PCR or restriction enzyme digestion) independent of other sequences. It also includes a recombinant DNA, which is part of a hybrid gene encoding additional polypeptide sequences. Neuroprotective genes and nucleic acid sequences that are particularly preferred for use in certain aspects of the present methods are genes encoding the heat shock proteins, as described above.

Generally, nucleic acid sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where such sequences do not interfere with manipulation or expression of the coding regions.

The term "recombinant" polynucleotide or nucleic acid refers to one which is not naturally occurring, or is made by the artificial combination of two otherwise separated segments of sequence. Recombinant nucleic acids sequences, as used herein, refers to nucleic acid sequences that are the product of various combinations of cloning, restriction, and ligation steps, resulting in a construct having a structural coding sequence distinguishable from homologous sequences found in natural systems. This artificial combination is often accomplished by either chemical synthetic means, or by the artificial manipulation of isolated segments of nucleic acids, e.g., by genetic engineering techniques. The manipulation is usually done to replace a codon with a redundant codon encoding the same or a conservative amino acid, while typically introducing or removing a sequence recognition site. Alternatively, the manipulation joins together nucleic acid segments of desired functions to generate a desired combination of functions.

It will, of course, be understood that one or more than one nucleic acid molecules encoding one or more neuroprotective polypeptides may be used in the methods and compositions of the invention. The nucleic acid delivery methods may thus entail the administration of one, two, three, or more, nucleic acid molecules encoding a neuroprotective polypeptide. The maximum number of neuroprotective proteins to be delivered is limited only by practical considerations, such as the effort involved in simultaneously preparing a large number of constructs or the possibility of eliciting an adverse cytotoxic effect.

Thus, an almost endless combination of different nucleic acids, genes or genetic constructs may be employed. Certain combinations may be designed to, or their use may otherwise result in, achieving synergistic effects on, for example, neuroprotective effects, CNS cell repair or growth, or other desired effect. Any and all such combinations are intended to fall within the scope of the present invention.

It will also be understood that, if desired, the nucleic acid molecule can be administered in combination with other agents, such as, e.g., other proteins or polypeptides or various pharmaceutically active agents. So long as a liposomal-genetic material complex forms part of the composition, there is virtually no limit to other components which may also be included, given that the additional agents do not cause a significant adverse effect upon contact with the target cells or tissues. The nucleic acids may, thus, be delivered along with various other agents, as required in the particular instance.

By "construct" or "vector" is meant a recombinant nucleic acid that has been generated for the purpose of the expression of a specific nucleotide sequence(s), or is to be used in the construction of other recombinant nucleotide sequences. Constructs of particular interest in the present invention are those that provide for production of a stable mRNA encoding a polypeptide of interest, which RNA can be formulated for administration according to the methods of the invention. As used herein, a "vector" is specifically a composition of matter comprising an isolated nucleic acid, which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" generally includes an autonomously replicating plasmid or a virus. Examples of viral vectors include, but are not limited to, adenoviral vectors, adeno-associated virus vectors, retroviral vectors, and the like.

However, in accordance with the present invention, the term "vector" is specifically construed to mean non-viral compounds which facilitate transfer of nucleic acid into cells, such as, e.g., polylysine compounds, liposomes, lipoplexes, and the like.

"Expression vector" refers to a vector comprising a recombinant polynucleotide comprising expression control sequences operatively linked to a nucleotide sequence to be expressed. An expression vector comprising sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide, and in the present invention further specifically include non viral lipid-based and lipoplex compositions. See also U.S. Pat. No. 5,168,050, incorporated herein by reference.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene. An "mRNA-coding region" of a gene consists of the nucleotide residues of the coding strand of the gene and the nucleotide residues of the non-coding strand of the gene which are homologous with or complementary to, respectively, an mRNA molecule, which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

For an mRNA molecule, the "coding region" consists of the nucleotide residues of the mRNA molecule which are matched with an anticodon region of a transfer RNA molecule during translation of the mRNA molecule, or which encode a stop codon. The coding region may thus include nucleotide residues corresponding to amino acid residues which are not present in the mature protein encoded by the mRNA molecule (e.g. amino acid residues in a protein export signal sequence).

"Linked" or "operably linked" refers to a juxtaposition, wherein the components so described are in a relationship permitting them to function in their intended manner. For instance, a promoter is "operably linked" to a coding sequence if the promoter affects transcription or expression of the coding sequence. By way of example, a promoter operably linked to the coding region of a gene is able to promote transcription of the coding region.

Associated with the coding region is the "transcriptional control region" (sometimes referred to as a "transcriptional regulatory region"), which encompasses all of the elements necessary for transcription, and may include elements necessary for regulation and cell-specific transcription. Thus, a transcriptional control region includes at least the promoter sequence, and may also include other regulatory sequences, such as enhancers, and transcription factor binding sites. A "transcriptional control region heterologous to a coding region" is one that is not normally associated with the coding region in nature.

"Regulatory sequences" refer to those sequences normally associated with (for example within 50 kb) of the coding region of a locus which affect the expression of the gene (including transcription of the gene, and translation, splicing, stability, or the like of the messenger RNA). Regulatory sequences include, inter alia, promoters, enhancers, splice sites and polyadenylation sites.

By "transfection" or "transformation" as used herein is meant a permanent or transient genetic change induced in a cell following incorporation of new nucleic acid (e.g., DNA or RNA that is exogenous to the cell). Genetic change can be accomplished either by incorporation of the new nucleic acid into the genome of the host cell, or by transient or stable maintenance of the new nucleic acid, e.g., as an episomal element. When the nucleic acid is RNA, expression involves translation of the encoded polypeptide by the host cell. A "host cell," as used herein, denotes microorganisms or eukaryotic cells or cell lines cultured as unicellular entities, which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The term "polypeptide" refers to a polymer of amino acids, but it does not refer to a specific length of the product. Thus, peptides, oligopeptides, and proteins are interchangeably included within the definition of "polypeptide." Further, it is recognized that, although a polypeptide is transcribed from an mRNA sequence, not all mRNA sequences encode active proteins, nor do all encoded polypeptides have therapeutic value for an intended purpose. As used herein, it is understood that this term is not intended to refer to, or exclude, post-translational modifications of the polypeptide, e.g., glycosylations, acetylations, phosphorylations, and the like. Included within this definition are, for example, polypeptides containing one or more analogs of an amino acid (including, e.g., unnatural amino acids, non-coded amino acids, etc.), polypeptides with substituted linkages, as well as other modifications known in the art, both naturally occurring and non-naturally occurring or synthetic.

As used herein, the term "substantially pure" or "substantially purified" refers to a compound (nucleic acid, polypeptide or protein) that is removed from its natural environment and separated from components which naturally accompany it. Typically, a compound is substantially pure when at least 10%, at least 20%, at least 50%, at least 60%, at least 75%, at least 90%, or at least 99% of the total material (by volume, by wet or dry weight, or by mole percent or mole fraction) of a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state. A "substantially pure nucleic acid" refers to a nucleic acid sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs or from other components which naturally accompany the nucleic acid, e.g., RNA or DNA or proteins which naturally accompany it in the cell.

Neuroprotective polypeptides are of particular interest to the present invention, specifically those that provide protection against or mitigation or accelerated recovery from brain or neural injury, especially injury resulting from hypoxia or ischemia as a result of injury or surgical intervention. Such polypeptides include, but are not necessarily limited to, heat shock proteins (HSP).

Heat Shock Proteins

Neuroprotective proteins of interest include, but are not necessarily limited to, members of the heat shock protein family (e.g., Hsp70, Hsp27, 90, 160, 180, 116, and the like), intracellular nitric oxide synthases (iNOS), superoxide dismutases (SOD), members of the Bel family, hemoxygenases, and the like. Any of the above or other related polypeptides, or portions of such polypeptides, may be used in the methods of the present invention. Where multiple polypeptides are delivered to a CNS cell, they may be combined on a single genetic construct under control of one or more promoters (in the case of delivery of DNA), or they may be prepared as separate constructs of the same or different types.

The invention encompasses the specific utility of myristoyl lauroyl Rosenthal inhibitor (MLRI or LMRI) congeners with HSP70 and HSP27 mRNA and DNA as unique and specific embodiments for delivery into the CNS of primates, including humans, through delivery to the CSF. Note that MLRI and LMRI are essentially interchangeable, differing only in the structure of the myristoyl lauroyl composition. In fact, the present invention does not depend on any specific lipid or vector, but it will work with any nucleic acid. Thus, as shown, the results can be achieved with the non-invasive, intrathecal route of administration using a variety of lipids, including MLRI, LMRI, Transfast, and PMDI and variations and improvements thereto, including the DMDK lipid disclosed herein. Thus, for simplicity, in describing the present non-invasive method for protecting and delivering a nucleic acid to cells of the CNS, the ligand method is used in general to form "congeners" defined in chemistry as one of many variants or configurations of a common chemical structure, as in MLRI or LMRI. For example, polychlorinated biphenyls (PCBs) occur in 209 different forms, or congeners. Each congener has two or chlorine atoms located at specific sites on the PCB molecule.

As a member of the Heat Shock Protein family, Hsp70 is an inducible, stress response protein, normally present in low levels in the "normal" cell and highly conserved across species. When cells, including those of the CNS, are under severe stress, such as hypoxia or ischemia, the gene for Hsp70 is rapidly and robustly induced and the cells produce large amounts of this protein. If these cells are subsequently subjected to another severe stress, they will survive the stress better than if they had not been "preconditioned" by the first stress. It is clear from prior transgenic and viral gene delivery experiments that high levels of Hsp70 in 'pre-stressed' cells, at least in part, protect cells that are subjected to a subsequent stress from injury. Once the stress on the cells is gone, however, levels of Hsp70 decrease rapidly. Therefore, Hsp70 is an endogenous protein that has potential therapeutic value for a transient period of time.

Accordingly, the vector:lipid complex embodied herein is an appropriate system for delivery of Hsp70 to cells of the CNS for transient, prophylactic neuroprotection, in lieu of an initial preconditioning stress event that leads to endogenous induction of the protein, and in vivo protection will be provided to humans or animals subjected to ischemic stress. As demonstrated herein using a reporter gene, luciferase, rapid and transient expression of a protein encoded by the introduced nucleic acid results from in vivo transfection, as required to provide delivery of Hsp70 to the CNS cells. Moreover, uptake of the vector:lipid complex and expression of the encoded protein is widespread throughout the CNS after CSF injection, and with little or no toxicity.

Embodiments of the disclosed delivery methods for delivering the complexed nucleic acids encoding selected therapeutic or protective polypeptides is effective for all aspects of neuroprotection, including, but not limited to, stroke and associated neurological damage; neurological complications of cardiac disease, including, but not limited to acute MI, TBI, SCI; delivery prior to, immediately subsequent to, or at the time of, any major or minor surgical intervention; delivery secondary to any major acute neurological disease, including traumatic brain injury and spinal cord injury; and all chronic neurological diseases, including multiple sclerosis (MS), amyolateral sclerosis (ALS), neurodegenerative disease, polyglutamine repeat diseases, unfolded protein neurological disease, and Alzheimer's.

In addition, all changes in the underlying structure of MLRI or LMRI, as well as in the newer cationic lipid, PMDI, or cationic lipid substitutes are encompassed by the invention, as well as all formulations of genetic material delivering or expressing HSPs to be utilized in congeners. Furthermore, all formulations of LMRI are also protected including any structural changes necessary to increase delivery, expression or neuroprotection of associated HSP-congener complexes. Results of flow cytometry after transfection demonstrate considerable differences in cytotoxicity and cellular uptake of lipids which vary in symmetry, head group, and charge ratio. Therefore, all symmetry, head group and charge ratio modifications of either the MLRI or LMRI congeners with HSP 70 and HSP27 comprise embodiments of the invention, and may be part of congener library. In particular, lipids composed of structures relayed in U.S. Pat. Nos. 5,869,715; 5,925,623 and 5,824,812 (Nantz et al.) are cationic lipids available for formation of congener molecules. Further, the invention provides methods for protection of all in vivo optimizations of reporter and therapeutic genes involved in the formulation or delivery of genetic material associated with HSPs. The optimized genetic material combined with MLRI or LMRI for CNS delivery in all primates, including humans, further serves as part of the congener library.

Although not wishing to be bound by a particular theory, the neuroprotection offered by Hsp70 to ischemic injury may be related to its ability to inhibit protein aggregation. While ATP hydrolysis is required to facilitate folding of nascent or denatured proteins (O'Brien et al., supra, 1996; Ohno et at, supra, 2004), without ATP, Hsp70 can bind denatured proteins as a molecular chaperone, causing them to maintain solubility. If nascent or denatured polypeptides cannot be folded successfully, they must be degraded by the ubiquitin-proteasome system. However, this process is likely impaired during ischemia due, in part, to ATP depletion, and potentially, in part, due to inhibition of the proteosome by protein aggregates (Bence et al. 2001). As a result, it is now recognized that protein aggregation and misfolding play an important role in a variety of diseases affecting the central nervous system, including acute injury, such as stroke, as well as in chronic neurodegeneration, such as that which occurs in Huntington's, Alzheimer's, and Parkinson's diseases. Protein aggregates commonly display ubiquitin immunoreactivity, suggesting that proteins targeted for degradation that fail to be degraded, may be the ones that form aggregates.

Gene Therapy Methods and Models

Unlike gene therapies proposed in the past, one major advantage of the present invention is the transitory nature of the production of the encoded polypeptide in the cells. With mRNA introduced according to the present invention, polypeptide production, and thus the desired effect, will generally last on the order of hours (e.g., about 1 hour to disappearance at about 48 hours, generally about 1 to disappearance after about 24 hours, more usually duration is about 1 to about 12 hours, or 1 to a peak at 4 or 5 hours). DNA introduced according to the invention can generally provide the desired effect for a period on the order of hours to days (e.g., about 1 day to about 7 days, usually about 1 day to about 4 days or 5 days). Relevant to the present invention is "transient expression" or "short-term expression," meaning that expression of a polypeptide (or other gene product) encoded by the introduced nucleic acid is not intended to remain active for the life of the subject. Accordingly, as indicated duration is generally less than one week, usually on the order of about 1 to 2 days, for DNA, but it may persist for less than 12 hours for mRNA. Generally, the germ line DNA is not affected.

Cells in cell culture, cell supernatants, cell lysates, serum, plasma, biological fluids, tissue samples and the like are encompassed herein by the term "biological sample." The term also refers to any of a variety of additional sample types obtained from an organism. The samples can be used, for example, in a therapeutic setting or in a diagnostic or monitoring assay. The term encompasses blood and other liquid samples of biological origin, particularly the CSF in the present invention, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components, and further includes clinical samples.

The cell types used herein were selected because they are easily handled, have well-established characteristics, and their laboratory culture conditions are well known, thereby reducing unknown variables in the in vivo experiments. To test the effectiveness of the methods of the present invention on non-proliferating cells, proliferation-inhibited CHO and NIH 3T3 cells, with either RNA or DNA vectors expressing GFP, were assessed following cationic lipid-mediated stabilization and delivery. Using flow cytometry analysis, transfection efficiency was assessed as a measure of the percentage of cells expressing GFP.

Transfection efficiency of RNA was greater than that of DNA in both proliferation-inhibited CHO cells (FIG. 1) and NIH 3T3 cells (FIG. 2), supporting the hypothesis that the use of RNA (immediately available for translation once delivered to the cytoplasm of the cell) avoids the necessity for translocating DNA to the nucleus and returning it to the cytoplasm before transcription can begin. Thus, the use of RNA leads to marked improvements in transfection efficiency over DNA transfection in non-dividing cells. Moreover, mRNA is a self limited gene transfer "drug" that eliminates even minimal risk of problematic DNA incorporation, seen in DNA-based gene therapy. Thus, the findings of Brisson et al., supra, 1999, are confirmed. Brisson et al. used 293 cells expressing T7 bacterial polymerase to show that T7 promoter driven DNA vectors, for which cytoplasmic transcription occurs, provided improved transfection efficiency relative to CMV promoter driven DNA vectors. As described above, the DNA vectors, of course, required nuclear translocation prior to transcription. See, Chapman et al., supra, 1991. Quantifying the importance of mitosis in DNA transfections, and demonstrating the efficiency of mRNA in the present invention, further confirmed that mRNA is a more efficient method for gene delivery to post-mitotic, non-proliferating cells.

In repeated experiments on primary mixed neuronal cultures, it was found that RNA vector expression levels approached 50%, whereas lipid-mediated gene transfer of DNA vectors into primary neurons showed a significantly lower efficiency, transfecting less than 25% of the primary neurons. Maximum expression following RNA vector delivery was observed at 5 to 7 hours post incubation, approximately 40 hours earlier than maximum expression levels using DNA vectors (see Example 4). However, the maximum mean level of intensity of GFP expression per cell, following RNA delivery was significantly less than that achieved by DNA delivery. Once a single strand of DNA passively enters the nucleus, multiple mRNA templates are transcribed resulting in higher efficient mean levels of expression per cell. As a result, by effecting expression of the delivered mRNA, the amount of expression product can be controlled, and CNS cells are not overwhelmed by the production of massive quantities of DNA expression products. Moreover, even though stabilized mRNA transcripts were used, the lipo-complexed RNA vectors are degraded once they are released from the lipid complex into the cytoplasm. Consequently, the expression is transient, permitting duration to be controlled. Additional administrations of the same or other mRNA sequences can be used to achieve longer, yet controllable, effects.

Thus, as demonstrated by the present data, mitosis is an important factor in the lipid mediated transfection efficiency of mRNA in the cells, as compared with DNA, particularly in proliferation inhibited cell lines and primary neuronal cultures. Advantageously, when the nucleic acid delivered by the method of the invention is RNA, the mRNA does not have to penetrate the nucleus to direct protein synthesis. Since RNA delivery may be more suited to applications in which rapid, short-term transient gene transfer to post-mitotic (non-proliferating) cells is required, RNA-delivery provides rapid expression, because the requirement for DNA nuclear translocation and transcription prior to translation of the expression products is avoided. In light of this finding, it is now possible to match the duration and level of therapeutic gene expression to specific clinical applications, wherein transient gene expression is necessary or preferred using RNA, or a combination of RNA and DNA gene delivery. Examples of such situations include, without limitation, prophylactic delivery of neuroprotective genes to the CNS for prevention of injury during surgical procedures with high risk for CNS ischemia, or delivery of RNA following CNS trauma to minimize the initial cellular loss.

Simultaneous or sequential DNA delivery may also be used to protect against subsequent cellular loss due to secondary events, including reperfusion injury. In such cases, the window of opportunity for effective treatment may be narrow; therefore the design of an efficient method for rapid, but short term, gene expression after delivery is essential. The cationic lipid formulations of the present invention afford RNA protection from degradation in human CSF for at least 1 or more hours, whereas non-complexed RNA is immediately degraded (Anderson et al., supra, 2003). Combining mRNA vectors with delivery to the CSF offers rapid expression in the non-proliferating cells of the CNS, while avoiding problems associated with vascular barriers and viral vector safety issues.

Determining transfection efficiency of by either in vitro or in vivo studies often requires transfecting the gene of interest with a luciferase or GFP reporter gene, followed by double labeling, or by co-transfecting both a gene of interest and a reporter gene, which is inefficient. Both options involve additional time, creation of additional vectors, inefficient co-transfection, and additional imaging. These hurdles can be overcome by the use of a cationic lipid that can be tagged with a commercial available probe, such as a fluorescent marker, such as Alexa Fluor 488, without sacrificing transfection efficiency.

Central Nervous System Cells and Tissues

In embodiments of the invention, advantageous methods are provided for effecting the expression of a polypeptide from a nucleic acid of interest delivered to a non-proliferating CNS cell. As used herein, the term "CNS cell" refers to any or all of those cells having the capacity to ultimately form, or contribute to the formation of, central nervous system tissue. This can include various cells in different stages of differentiation, such as, for example, developmentally different fetal and adult neural cells, as well as neurons, astroglia, astrocytes, microglia, oligodendrocytes, and the like, with adult neural cells being of particular interest.

CNS cells also include cells that have been isolated and manipulated in vitro. The particular type(s) of CNS cells in which nucleic acid, particularly RNA, encoding a polypeptide of interest for expression (i.e., translation and production of the encoded polypeptide) in the CNS cell using the methods and compositions of the invention are not necessarily critical, so long as the cells produce the polypeptide of interest to provide the desired effect, e.g., a protective or neuroprotective effect. CNS cells may also be isolated from animal or human tissues and maintained in an in vitro or ex vivo environment. Isolated cells may be transfected using the methods and compositions disclosed herein and, if desired, are returned to an appropriate site in an animal where the CNS cell provides the desired effect. In such cases, the nucleic-acid containing cells would themselves be a form of therapeutic agent. Such ex vivo protocols are well known to those of ordinary skill in the art.

In certain embodiments of the invention, the CNS cells and tissues will be those cells and tissues that may be damaged, or subject to damage, that one wants to prevent, including prophylactically, or to treat or mitigate (either prophylactically, at the time of, or following onset of the disease, condition, damage, etc.). Accordingly, in therapeutic embodiments, there is no difficulty associated with identifying suitable target cells to which the present therapeutic compositions should be applied. In such cases, one need only to obtain a nucleic acid molecule, preferably RNA, encoding a gene of interest, such as those disclosed herein, and contact the site of the injury or defect with a transfecting formulation comprising the nucleic acid. In accordance with the present invention, the appropriate cells will be transfected without the need for further targeting or cellular identification by the practitioner.

Certain embodiments of the invention involve, generally, methods for contacting CNS cells with a composition comprising a nucleic acid molecule, DNA or RNA, but preferably an mRNA molecule encoding a polypeptide of interest, so as to promote expression of the nucleic acid molecule in the CNS cells. Further, the methods of the invention can be used to deliver a polypeptide (or other gene product) of interest to any cell of a subject, delivery of a polypeptide of interest to a cell of the central nervous system (CNS) is of particular interest. While generally any polypeptide can be delivered to, or caused to be expressed in, such CNS cells (or other desired cell), delivery of polypeptides that provide for a protective effect, especially a neuroprotective effect in the case of a CNS cell, are of particular interest, although such references throughout the specification are meant to be only exemplary, not limiting. For example, the methods of the invention can also be used to provide for neuroprotection in the context of stroke, trauma, or various other neurodegenerative injuries or diseases described herein.

While the CNS cells may be contacted in vitro or in vivo, in vivo delivery is of particular interest. Production of a polypeptide of interest in a CNS cell is achieved, in the most direct manner, by simply obtaining a functional polypeptide-encoding nucleic acid molecule and applying it to the cells by methods provided herein. The term "treatment" is used herein to encompass any treatment of any disease or condition in a mammal, particularly a human, and includes: a) preventing a disease, condition, or symptom of a disease or condition from occurring in a subject, who may be predisposed to the disease, but has not yet been diagnosed as having it; b) inhibiting or reducing the severity of a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

Further, "treatment" in the present invention is extended to remediation of injury, particularly associated with hypoxia or the resulting ischemia. Repair of aneurysms, particularly in the thoracic aortic artery (TAA) and thoraco-abdominal aortic artery (TAAA), carries a high risk (5-40%) of spinal cord ischemia, depending on location, acuity of the repair and patient risk factors. Elective surgical repair of an unruptured aneurism carries a risk of 5-15% mortality, but left without repair, the rate of rupture is 50-95% and mortality is a 90% probability. Acute ischemia and possible reperfusion injuries (if the spinal cord is reperfused) appear to be the primary cause of spinal cord paralysis (Jacobs et al., *J. Vasc. Surg.* 35:30-37 (2002)). Ischemia occurs as a secondary effect to the loss of perfusion in the mid-thoracic region, resulting in watershed infarcts. This loss of spinal cord perfusion results from a loss of critical intercostals arteries that are occluded during the repair process, during aortic cross-clamping, and due to increased intracerebral pressure (ICP). Despite reductions in operating time and less invasive procedures, epidural cooling, augmented perfusion, pharmacologic measures and the like, acute anterior spinal cord ischemia paraplegia (intra-operative or post-operative) remains a significant factor, and failure to detect the spinal cord ischemia uniformly leads to permanent paraplegia. Accordingly, prevent or treat spinal cord ischemia and the ability to predict an increased risk of paralysis would be of great benefit in preventing this devastating complication.

"Hypoxia" is a pathological condition in which the body as a whole (generalized hypoxia) or region of the body (tissue hypoxia) is deprived of adequate oxygen supply. Low oxygen content in the blood is referred to as hypoxaemia. Hypoxia in which there is complete deprivation of oxygen supply is referred to as anoxia. The present invention relates specifically to the effect of hypoxia on the brain or neurons of the CNS. As compared with hypoxia, generally indicating a shortage of oxygen, "ischemia" is an absolute or relative shortage of oxygenated blood to an organ, generally due to factors including a lack of oxygen in the blood vessels or obstruction of the arterial blood supply with resultant damage or dysfunction of tissue. Thus, while ischemia usually happens because of a shortage of blood and oxygen to the heart muscle, e.g., during aortic or heart/lung surgery, or as a result of narrowing or blockage of one or more of the coronary arteries (which supply blood to the heart muscle), an inadequate blood flow can lead to a hypoxic state in the cells, and hence in the tissue As a result, while ischemia may be a temporary problem or intermittent problem, surgically induced ischemia may result in irreversible cell necrosis and death or neural tissue and cells of the CNS and brain if the deprivation extends beyond 10-12 hours.

By "protection," especially as used in the context of "protection from ischemia," is meant that an agent affords a defense to a cell or tissue against a deleterious influence. Hypoxia from ischemia can rarely be completely and absolutely prevented during aortic or heart/lung surgery, so protection need not be absolute prevention to be effective in accordance with the standards of the present invention. Thus, an agent provides "protection" when the severity of damage normally caused by a simultaneous or subsequent insult, e.g., biological (including, ischemia, hypoxia, stroke, trauma, neurodegenerative disease, and the like), mechanical (e.g., surgically-induced injury, severe stress including surgical stress or trauma), chemical, biological, or other insult, is at least partially mitigated or reversed, and may be substantially avoided.

"Neuroprotective" refers to use of the present invention to protect of neuronal cells of the CNS, and in some embodiments, may extend to prevention of damage from ischemic injury, preventing or decreasing the severity of neural or nervous system injuries, improving recovery time from CNS injuries, and promoting nervous system cell repair and regeneration. Neuroprotective also refers to pre-operative protection from ischemic CNS damage, as well as to attenuation of secondary injury following stroke, brain or spinal cord trauma, SCI or neurodegenerative disease.

Widespread Distribution of the Nucleic Acid Vector In Vivo

Delivery of exogenous genes by non-viral vectors does not lead to integration of the delivered sequence into the target tissue genome, thus gene expression is transient and controllable. Experiments were developed to quantify the time course of our non-viral, lipid-mediated gene delivery system by following the transient expression of the reporter gene firefly luciferase. This system acts as a model for the delivery of vectors carrying therapeutic genes for transient, pre-operative neuroprotection. The luciferase expression in cells of the CNS was followed by in vivo imaging after CSF delivery of the plasmid pND.Luc complexed with the cationic lipid MLRI. After vector delivery, rats were injected with the enzyme substrate, luciferin, at 24 hour intervals and light emission was quantified at peak enzyme activity after each luciferin injection.

The in vivo results confirmed the in vitro time course experiments in CHO, NIH 3T3 and primary neuronal cells. In each cell type, when transfected with the same pND.Luc: MLRI vector complex, peak luciferase activity was evident 72 hours after transfection.

To compare outcomes, the vector:lipid complex was injected into the CSF either via the lateral ventricle or the cisterna magna, as well as directly into rat brain parenchyma. Comparison of the light emission pattern after CSF versus parenchymal injection showed distinctly different results. pND.Luc:MLRI complex delivery to the brain parenchyma resulted in signal emission that remains closely localized to the site of delivery with little expansion of the photon signal across the midline of the brain, even at the peak of 72 hours after injection. In marked contrast, however, vector:lipid delivery via the CSF showed widespread signal emission, reflecting bulk transport of the vector:lipid complex throughout the rat brain region. At the peak of the time course, the signal appeared to be symmetric over the rat's skull. The distinctly different patterns of light emission seen after parenchymal versus CSF delivery of the vector further confirmed that the CSF injections (performed either blind into the cisterna magna, or by stereotactic coordinates) reached the target.

While the time course of gene expression in vivo from the same promoter/enhancer sequences (i.e. from the same vector construct) should be independent of the gene sequence expressed, the half-life of the expressed protein is specific. Thus, the time course of expression of a reporter gene is representative of the time course of expression of any therapeutic gene of interest. This is consistent with the rapid decrease in DNA copy numbers in the CNS of rhesus macaques following cisterna magna infusion of identical lipids, formulations, and DNA vectors (unpublished results).

Pharmaceutical/Therapeutic Applications

The formulations of the pharmaceutical compositions described herein encompass those prepared by any method known or hereafter developed in the art of pharmacology. In general, such preparatory methods include the step of bringing the active agent into association with the congener and a carrier or one or more other accessory ingredients, and then, if necessary or desirable, shaping or packaging the product into a desired single- or multi-dose unit. In preferred embodiments of the invention, the formulation is administered in an amount sufficient to effect the expression of the encoded polypeptide in a CNS cell at a level sufficient to at least partially protect or remediate the CNS cell from ischemic injury. By "amount sufficient" or an "effective amount" is meant that quantity of an active agent, drug or therapeutic or prophylactic composition to effect a measurable beneficial or desired biologic, physiologic or clinical result. For example with regard to HSP70, roughly equivalent intensity of expression has been shown after delivery, uptake, and expression of the DNA/lipid lipoplex in rat brain when compared to a peak of endogenous expression of HSP70 after heat shock. It is assumed that the robust endogenous expression after heat shock is a reasonable first approximation for what constitutes a robust cyto-protective response in vivo. Preferably in accordance with the present invention, the effectiveness of the delivered vector or the protein expressed from the delivered nucleic acid achieves success and therapeutic or prophylactic effectiveness of at least about 30% over that which would occur absent practice of the methods disclosed herein. More preferably, the beneficial effect is about 40%, or 50%, or 70%, or 85%, or 90%, or 95%, or 99%, up to 100% greater than absent treatment, without toxicity to the cells or the patient.

The terms "suppression," "inhibition" and "prevention" are used herein in accordance with accepted definitions as compared with the response that results absent treatment by the present invention. When administered prophylacticly, such blockage may be complete; or in the present invention, the treatment may advantageously reduce the effect as compared to the normal untreated state, typically referred to as suppression or inhibition.

Although the methods described herein are principally directed to pharmaceutical compositions which are suitable for ethical administration to humans, it will be understood by the skilled artisan that such compositions are generally suitable for administration to animals of all sorts. By "subject" or "individual" or "patient" is meant any subject for whom diagnosis or therapy is desired, particularly humans. Other subjects may include agricultural species, such as, cattle, horses, sheep, goats, pigs, or other mammals, including commercially-relevant mammals, and veterinary, domestic, experimental or wild-type species, such as, dogs, cats, guinea pigs, rabbits, rats, mice, and the like, as well as any species in which hypoxia or ischemia may result in damage to cell or tissues of the CNS. Thus, the invention may be extended to fish, birds, and other species having both circulatory and central nervous systems, and in which the present invention may be useful.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Single or multiple injections of any concentration of an HSP-expressing DNA or RNA vector, expressly encompassing HSP70 and HSP27, lipoplexed using a calculated and optimized charge ratio of any total volume can be injected into free CSF of any subject, including humans. Furthermore, this formulation and any adjustments for quantity and concentration may be prepared, packaged, sold, or utilized in formulations suitable for methods of delivery into blood or CSF, via oral, subcutaneous, rectal, vaginal, parenteral, topical, pulmonary, intranasal, buccal, ophthalmic, intrathecal, or another route of administration. Other contemplated formulations include projected nanoparticles, liposomal preparations, and resealed erythrocytes containing the active agent and congener.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active agent and congener. The amount of the active agent is generally equal to the dosage of the active ingredient which would be administered to a subject or a convenient fraction of such a dosage such as, for example, one-half or one-third of such a dosage. The relative amounts of the active agent, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active agent.

In addition to the active agent and congener, a pharmaceutical composition of the invention may further comprise one or more additional pharmaceutically active agents or adjuvants. Controlled- or sustained-release formulations of a pharmaceutical composition of the invention may be made using conventional technologies.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. This injection can also be given through the spinal canal, or any other closed or open communication with the subject's CNS. In particular, parenteral administration is contemplated to include, but is not limited to, intraventricular (into the brain's ventricles), subcutaneous, intraperitoneal, intramuscular, intrasternal injection, and kidney dialytic infusion techniques. All methods of blood/brain barrier enhancement can be utilized in the present invention, including, but not limited to, open surgical exposure, pharmacological expansion and all related therapies.

Formulations of a pharmaceutical composition suitable for parenteral administration comprise the active agent combined with the congener in a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile, injectable, aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils, such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents;

preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example, in *Remington's Pharmaceutical Sciences* (1985, Genaro, ed., Mack Publishing Co., Easton, Pa.), which is incorporated herein by reference.

Typically dosages of the antibody of the invention which may be administered to an animal, preferably a human, range in amount from 1 µg to about 100 g per kilogram of body weight of the animal. The precise dosage administered will vary depending upon any number of factors, including but not limited to, the type of animal and type of disease state being treated, the age of the animal and the route of administration.

The congener can be given at any time either prior to or subsequent to the ischemic insult within an unlimited time parameter. When administered to an animal, the pharmaceutical composition of the invention may be administered as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. In addition, the blood level of the active agent administered in the pharmaceutical composition may be monitored in the subject's blood or CSF as another factor in determining the dose frequency.

The invention further provides kits useful in the practice of the methods of the invention, for instance, to treat or prevent ischemic injury or damage to cells of the CNS, without the risk of introducing viral vectors. The kits comprise a container comprising a non-viral, cationic lipid or lipid mediated vector of the invention and an instructional material for the use thereof. As used herein, an "instructional material" includes a publication, a recording, a diagram, or any other medium of expression which can be used to communicate the usefulness of the kit for treating or preventing ischemic injury or damage to cells of the CNS, without introducing viral vectors. The instructional material of the kit of the invention may, for example, be affixed to a container containing the non-viral, cationic lipid or lipid mediated vector, or be shipped together with a container containing the medium. Alternatively, the instructional material may be shipped separately from the container with the intention that the instructional material and the non-viral, cationic lipid or lipid mediated vector be used cooperatively by the recipient. The kits can also contain any other component useful in the practice of the inventive methods including, but not limited to, a container for a biological sample, and positive and negative control samples.

The stability of the lipids has been confirmed as evaporated 1:1 mM lipid:DOPE, which is stored at −80 under an inert gas, such as Argon, then reconstitution with double distilled water, nuclease free ($ddH_2O$). Such lipids are stable for months.

The present invention is further described in the following examples. These examples are provided for purposes of illustration only, and are not intended to be limiting unless otherwise specified. The various scenarios are relevant for many practical situations, and are intended to be merely exemplary to those skilled in the art, but are not to be construed as limiting the scope of the appended claims. Thus, the following examples should be construed to encompass any and all variations which become evident in light of the teaching provided herein.

Examples

Example 1

Lipid-Mediated Delivery of RNA in Non-Dividing Cells is More Efficient than DNA

Materials and Methods

Cell Maintenance:

Both proliferation-inhibited Chinese Hamster Ovary (CHO) cells (ATCC, Rockville, Md.) and NIH 3T3 fibroblast cells (ATCC, Rockville, Md.) were cultured in 75 $cm^2$ cell culture flasks with media containing 10% bovine calf serum at 37° C. in a 5% $CO_2$ environment, in HAMS F12 media (Life Technologies, Gaithersburg, Md.) or DMEM media (Life Technologies) respectively. Both CHO and NIH3T3 cells were split 24-48 hours prior to transfection and plated at 60% confluence, e.g., plated at 50,000 cells per well using 24 well plates (Falcon, Franklin Lakes, N.J.)

Primary Neuronal Cells:

Primary neuronal cells were dissected from the cortex of day 17 Sprague-Dawley fetal rat brains as previously described by McKinney et al., Stroke 27:934-940 (1996). Briefly, fetal rat brains were removed and placed in ice cold sterile PBS where the cortex was dissected and cleared of meninges. Cortical sections were transferred to a 60 mm Petri dish containing 4 ml phosphate buffered saline (PBS) and minced into pieces of approximately 1 cubic millimeter (mm) in size, then transferred into a 15 ml sterile tube, supplemented with 4 ml neural basal medium containing: 0.5 mM L-glutamine, 1× B27, and 50 ng/ml neural growth factor, supplemented with 0.25% trypsin-EDTA and 20 µl DNase I, and shaken for 30 minutes at 37° C. The resultant suspension was mechanically forced through a Pasteur pipette tube to eliminate residual clumps of brain tissue, and then filtered through 40 µM nylon net to obtain single cell suspensions. Cells were spun down and resuspended in neural basal medium as above. $1 \times 10^6$ cells per ml were seeded onto poly-L-lysine, pre-coated 24 well tissue culture dishes. Cells were cultured in a 5% $CO_2$ incubator at 37° C., and maintained in culture for two weeks prior to transfection to develop the correspondent mature phenotype of human cortical neurons. Every 3-4 days, one half of the medium was replaced with medium containing fresh neural growth factor. Cultures of cortical neuron prepared in this fashion contained less than 10% glial cells (unpublished results).

Proliferation Inhibition:

To inhibit cell proliferation, CHO cells were treated with 15 µM roscovitine (Sigma, St. Louis, Mo.) for 1 hour with lipid transfection formulations containing 1 µg of GFP RNA or DNA vector, while NIH 3T3 cells were treated with 21 µM roscovitine diluted in serum free media for 1 hour with lipid transfection formulations containing 1 µg of GFP or luciferase RNA or DNA vector, 24 hours prior to transfection. Concentrations were determined after a series of experiments to examine cell viability.

Nucleic Acid Delivery Vectors:

eGFP DNA vector (pND.eGFP) and luciferase DNA vector (pND.Lux) (from G. Rhodes, University of California, Davis) contained the human cytomegalovirus ("CMV") immediate early promoter (HCMV 1E1) and CMV 1E1 intron, and a multiple cloning site (MCS). The eGFP and luciferase coding sequences were inserted into the MCS, followed by the RNA terminator/polyadenylation site derived from bovine growth hormone ("BGH") (Chapman et al., *Nucl. Acids Res.* 19:3979-3986 (1991), in a pUC19 replicon. These elements are contained in a pUC19 replicon cDNA encoding the luciferase gene from the firefly *Photinus pyralis* (pGL21$^+$; Promega, Madison, Wis.), cloned into expression vector pND. The HSP70 DNA vector was constructed by subcloning HSP70 cDNA (from Morimoto, Northwestern University) into the blank pND vector, forming the DNA vector, pNDHsp70.

eGFP and Luciferase mRNA Transcripts:

RNA vectors were constructed from either a β-globin luciferase plasmid (from J. Wolf, University of Wisconsin), or from the pT7OmegaGFPA50 plasmid (from R. Malone, University of California, Davis), containing the Omega 5' untranslated region ("UTR") and 3' poly-adenylated tail from Tobacco Mosaic Virus ("TMV") (Gallie et al., *Genes Develop.* 4:1149-1157 (1990); Balasubramaniam et al., *Gene Therapy* 3: 163-172 (1996)). Full length enhanced Green Fluorescent Protein (eGFP, a variant of jellyfish *Aequorea victoria* GFP) cDNA (pEGFP, Clontech, Palo Alto, Calif.) may in the alternative be subcloned into pND vector to provide the DNA vector, PND.eGFP).

5' and 3' untranslated regions (UTRs) have been shown to improve intracellular mRNA stability and lead to translational enhancements in eukaryotic, as well as prokaryotic cells (Wells et al., *Genes & Develop.* 12:3236-3251 (1998); Gallie et al, supra, 1990). Each of the resultant mRNA transcript contained a T7 promoter-driven, coding sequence stabilized by a 5' untranslated transcriptional enhancer and a 3' polyadenylated tail. Vectors for mRNA transcripts encoding GFP and luciferase were linearized with restriction enzyme Dra I, after elimination of RNases by proteinase K treatment and phenol/chloroform extraction. After precipitation in ethanol, the linearized DNA templates were transcribed in vitro using the T7 mMessage mMachine transcription kit (Ambion, Austin, Tex.).

Cationic Lipid Transfection Formulation:

After individual optimization and simultaneous comparison of several commercially available cationic lipids, described below, TransFast™ Transfection Reagent (Promega, Madison, Wis.) was chosen for its efficiency and low cytotoxicity. Liposome reagents specifically designed for transfection applications often incorporate synthetic cationic lipids, such as the neutral lipid L-dioleoylphosphatidyl-ethanolamine ("DOPE"), or with cholesterol. DOPE has been demonstrated to enhance the gene transfer ability of certain cationic lipids (Feigner et al., *J. Biol. Chem.* 269:2550-2561 (1994)). The; US Pa™ Transfection Reagent is comprised of the synthetic cationic lipid (+)-N,N{bis(2-hydroxyehyl)-N-methyl-N-{2,3-di(tetradecanolyloxy)propyl}ammonium iodide and the neutral lipid, DOPE (Promega, Wis.). Similar cationic lipids were described previously by Balasubramaniam et al., supra, 1996; Bennett et al. *Bioscience Reports* 15:47-53 (1995); Bennett et al., *J. Liposome Research* 6:545-565 (1996); U.S. Pat. No. 5,869,715 (Nantz et al.) and U.S. Pat. No. 6,372,722 (Bennett et al.), and Feigner et al., supra, 1994 and Scarfo et al. in press, 2006). Following manufacturers instructions, the lipid was rehydrated in water and stored overnight.

In an alternative formulation the cationic lipid comprises MLRI (myristoyl lauroyl Rosenthal inhibitor), in 500-600 µl total volume. MLRI is a dissymmetric myristoyl (14:0) and lauroyl (12:0) substituted compound, formed from the tetra alkylammonium glycerol-based prototypic cationic lipid DORI (N-(1-(2,3 dioleoxyloxy)propyl)-N-(1-(2-hydroxy) ethyl)-N,N-dimethyl ammonium iodide). MLRI was mixed 50:50 with DOPE in chloroform.

To test optimization procedures, monomer (MHL) and polymer (PCL) formulations were separately hydrated (10 mM Tris-HCl buffer containing NaCl (150 mM) at 1 mg/ml (1.5 mM cationic construct). The hydrated suspensions were vigorously mixed and then sonicated for 5 minutes at 50° C. to produce turbid liposome suspensions. The experimental lipids were labeled. Lipids provided in solid state were reconstituted in 150 mM NaCl solution using ddHOH at a concentration of 2 mM. Solutions were then neutralized to pH7 with 30 mM HCl and sonicated for 20 minutes at 50° C. Finally the lipid solutions were filtered over a 0.2 µm filter (Millipore, Billerica, Mass.) and maintained free of bacterial contamination. Soluble lipids (25 mM in 150 mM aqueous solution) were diluted with 150 mM NaCl to a concentration of 10 mM, pH was adjusted and filtered. Lipids were stored at 4° C.

The lipids were optimized by varying charge ratio and time of incubation. The "charge ratio" is represented as the ratio of charge, lipid to nucleic acid. For the test samples the lipids were transfected at charge ratios of 2:1, 4:1, 6:1, 8:1, 10:1, 12:1 and 14:1, and incubation times ranged from 10 to 30 minutes in 10 minute increments. After 10 minutes at room temperature, the polymer solution was added to the DNA solution and incubated at room temperature for time to permit charging. At the end of the incubation periods, the media was aspirated from the plated CHO cells, the cells were washed with Dulbecco's Phosphate Buffered Solution (DPBS) (Gibco, Carlsbad, Calif.), and transfection formulations were applied to the cells. CHO cells were incubated for 3 hours at 37° C. and 5% $CO_2$. Then the lipid/DNA mixture was aspirated from the cells and replaced with Kaign's modified media (Gibco) containing 10% fetal calf serum (Gibco).

The lipids were transfected with 1 µg pNDLuc or pNDGFP encoding DNA mixed with 100 µl Opti-MEM (Gibco). Twenty-four hours after transfection, the transfected cells were lysed in 200 and subjected to a luciferase assay using an enhanced luciferase assay kit (BD Bioscience, San Jose, Calif.), measured using a Moonlight 2010 device (Analytical Luminescence Laboratory). Twenty-four hours post-transfection, the cells were trypsinized and analyzed by flow cytometry as described below, and the data collected. The optimal charge ratio and incubation time for LMRI lipids based on transfection of pNDLuc-encoding DNA and analysis using an enhanced luciferase assay was 2:1 (lipid:DNA) and 60 minutes respectively at 37° C.

Cell Transfections:

Transfection formulations of GFP-encoding RNA and DNA vectors were optimized previously using flow cytometry to obtain the maximum percentage of GFP expressing cells by varying charge ratio, formulation time, concentration, and temperature. Cells were simultaneously transfected with 1 µg of either DNA or mRNA to avoid day to day and cell passage number variability. Although 1 µg each of DNA and RNA are not equal numbers of nucleic acid copies, lipid nucleic acid complexes were formulated based on an equal lipid to nucleic acid charge ratio. The lipid/nucleic acid complex was formed by the addition of nucleic acid to serum free media. After vortexing, lipid was added to produce a 1:1, probably 2:1 ratio, which is consistent with the charge ratio above. The final solution, in 200 was again vortexed, and incubated for 1 hour at room temperature (RT) prior to aspiration of growth media from the cells and application of transfection formulation to the cells. After 1 hour of incubation the cells were supplemented with 1 ml of growth media.

In the alternative formulation using MRLI, 50 µg/kg of GFP-expressing DNA vector was prepared in a 3:1 charge ratio with the cationic lipid, Cell Toxicity Analysis:

CHO cells were trypsinized and washed twice in Dulbecco's phosphate buffered saline with $Ca^{2+}$ (DPBS), re-suspended, and incubated for 30 minutes in annexin V conjugated with biotin (CalTag, Burlingame, Calif.) in DPBS. After a DPBS wash, the cells were resuspended for 30 minutes in streptavidin conjugated with a Tri-Color fluorophore (CalTag, Burlingame, Calif.) in DPBS. The cells were analyzed using a dual channel FACScan (Becton Dickinson, San Jose, Calif.) with a single 488 nm argon laser. GFP fluorescence was measured with a 530 nm band pass filter and Tri-Color fluorescence was measured with a 675 band pass filter. Because a low Annexin V signal was observed (reflecting low apoptosis) in CHO cells, the Annexin step was omitted for the following experiments.

Flow Cytometry Analysis:

CHO, NIH 3T3 and primary neuronal cells were trypsinized and washed twice in Dulbecco's phosphate buffered saline with $Ca^{2+}$ (DPBS) and resuspended in DPBS. GFP fluorescence was measured using a dual channel FACScan (Becton Dickinson, San Jose, Calif.) equipped with a single 488 nm argon laser and a 530 nm band pass filter. Data was analyzed with CellQuest software (Becton Dickinson), 10,000 events collected per sample. Cells were analyzed at 4, 8, 12, 24, and 48 hours to determine the maximum percentage of cells expressing GFP. Mean intensity of GFP expression was measured at the maxima for each of the experimental conditions. All experiments were conducted at least twice.

Time Course of Luciferase Expression in Primary Neurons after mRNA and DNA Transfections:

At specified time points after transfection of primary cortical neurons, cells were lysed in 200 µl of lysis buffer. 20 µl of lysate was analyzed by luciferase assay using an enhanced luciferase assay kit (BD Bioscience). Quantitative luminescence was measured using a Monolight 2010 (Analytical Luminescence Laboratory, Mountain View, Calif.).

In Vivo Luciferase-Expressing mRNA Vector Delivery to Lateral Ventricle:

As an example of the widespread distribution, uptake and expression after non-viral, cationic lipid-mediated gene delivery of mRNA vectors, an optimized formulation of luciferase-encoding mRNA transcript was infused into the lateral ventricle of rat brain. Direct injections were performed using standard techniques as previously reported by Hecker et al., supra, 2001 and Anderson et al., supra, 2003. Under an approved animal care protocol, adequately anesthetized animal subjects (250-300 g Sprague-Dawley rats) were mounted in a stereotaxic small animal surgery frame (Stoelting, Wood Dale, Ill.). Using sterile techniques, previously optimized formulations were delivered using coordinates of 0.9-1.0 mm posterior and 1.5 mm lateral of midline relative to bregma, at a depth of approximately 3-3.5 mm. After aspiration of CSF to verify intraventricular cannula placement, the transfection formulation was infused over 40 minutes using a syringe infusion pump (model 101, Stoelting). Animals were closely monitored for signs of discomfort, toxicity, or neurologic injury, and none were observed.

Tissue Preparation for Reporter Protein Localization:

Seven to eight hours after mRNA vector delivery, the animal subjects were deeply anesthetized and perfused through the ascending aorta with saline, followed by 4% paraformaldehyde in 0.1 M, pH 7.4 sodium phosphate-buffered saline. The brain was removed and dissected, post-fixed in paraformaldehyde fixative overnight at 4° C., and then placed in PBS containing 20% glycerol at 4° C. After blocking, brains were cryosectioned in the coronal plane following standard techniques, beginning approximately 6-7 mm anterior relative to bregma. Ten series of 30-mm serial sections were collected for each brain.

Diaminobenzidine Immunohistochemistry:

The peroxidase substrate, 3,3' diaminobenzidine (DAB), and secondary fluorescent immunohistochemistry protocols were optimized for expression using multiple DNA and mRNA vectors (Hecker et al., supra, 2001; Anderson et al., supra, 2003). These optimizations were conducted with neither primary nor secondary controls on the slides or in 24-well plates to ensure identical, simultaneous processing. Free-floating sections in 24-well plates were stained using the ExtrAvidin® peroxidase system (Sigma, St. Louis, Mo.). For comparison, experiments were also processed using sections mounted on poly-L-lysine-coated microscope slides (Columbia Diagnostics, Inc., Springfield, Va.) and air-dried for a minimum of 2 hours. $H_2O_2$ was used to eliminate staining caused by endogenous peroxidase activity.

For reporter enzyme localization and immunohistochemistry analyses, tissue sections were appropriately fixed in 4% paraformaldehyde (described above) following transfection of the animal subjects, and pretreated with 0.1% $H_2O_2$ for 15 minutes before washing in modified PBS. Sections were incubated in blocking buffer (0.3% Triton X-100, 3% bovine serum albumin (BSA), 10% normal goat serum (NGS), in modified PBS) for 2 hours at room temperature. Primary antibodies were appropriately diluted in blocking buffer and incubated at 4° C. overnight. Sections were washed and incubated with the biotin-conjugated secondary antibody, which targets the primary antibody host species, for 1 hour at room temperature. Sections were again washed and incubated with the tertiary horseradish peroxidase-conjugated probe for 1 hour at room temperature, washed again, and incubated in 50 mM Tris-HCl, pH 7.6 for 5 minutes at room temperature. For detection of target proteins sections were incubated with 0.5 mg/ml 3,3'-DAB with 0.03% $H_2O_2$ as the peroxidase substrate.

After the optimization described above, the following antibodies and dilutions were used. Primary antibodies: mouse monoclonal neuron specific nuclear protein anti-NeuN (MAB377, 1:50; Chemicon, Temecula, Calif.); rabbit polyclonal antiluciferase antibody (CR2029R, 1:50; Cortex Biochem, San Leandro, Calif.). The NeuN antibody was used for comparisons with the number of neurons that can be identified in each section (data not shown). Photographic documentation of results was by a Nikon 600 microscope with camera mount. Film negatives or slides were scanned into Photoshop 5.0 using a Photoshop plug-in and Polaroid SprintScan slide scanner at a resolution of 2700 dpi. Photographs were printed using Photoshop 5.0 (Adobe, Seattle, Wash.) on a Fuji Pictrography 3000 (Fuji Photo Film, Elmsford, N.Y.) at 320 dpi. Later experiments were documented on a Nikon Eclipse TS100 Inverted microscope (Japan) with a high resolution digital camera (Diagnostic Instruments).

Results

GFP RNA and DNA Vector Delivery in Proliferation-Inhibited CHOs:

Previously optimized GFP-encoding mRNA and DNA vectors were delivered to proliferation-inhibited CHO cells, and were analyzed at 4, 8, 12, 24, and 48 hours by FASCcan flow cytometry (Becton Dickinson) using Cell Quest software. Approximately 67% of the cells were reproducibly measured in the G0-G1-phase, 33% in the S-phase, and less than 1% in the G2M phase. Results are presented at the time point for the maximum percentage of cells expressing GFP, as these time points were different for mRNA versus DNA. As shown in FIG. 1, the maximum percentage of GFP-expressing cells represents 12 hours and 48 hours post-transfection time points for mRNA and DNA, respectively. In simultaneous transfections (to avoid passage number differences) GFP RNA vectors transfected over 45% of the proliferation-inhibited cells; but only approximately 11% of the cells were transfected with the GFP DNA vector. Thus, there was an approximately 4× increase in the percentage of cells transfected by GFP RNA, relative to GFP DNA. The mean level of expression per cell, as measured by Cell Quest analysis of GFP intensity, was greater than 5× higher in DNA-transfected cells, relative to RNA-transfected cells. Accordingly, despite the higher copy number of RNA transcripts that were delivered.

RNA and DNA Vector Delivery of GFP to Proliferation-Inhibited NIH 3T3 Cells:

When previously-optimized GFP-encoding mRNA and DNA vectors were delivered to proliferation-inhibited NIH 3T3 cells, and analyzed by flow cytometry at 4, 8, 12, 24, and 48 hours after delivery, the results are again presented at the time point at which the maximum percentage of cells expressed GFP. As shown in FIG. 2, the maximum percentage of GFP-expressing cells represents 12 hours and 48 hours post-transfection time points for mRNA and DNA, respectively. In simultaneous transfections, GFP RNA vectors transfected over 50% of proliferation-inhibited cells, but only approximately 17% of NIH3T3 cells were transfected with a GFP DNA vector. Thus, there was an approximately 3× increase in the percentage of cells transfected by GFP RNA, relative to GFP DNA. The mean level of expression per cell, as measured by Cell Quest analysis of GFP intensity, was greater than 4× higher in DNA-transfected cells, relative to RNA-transfected cells.

Figure 3A:
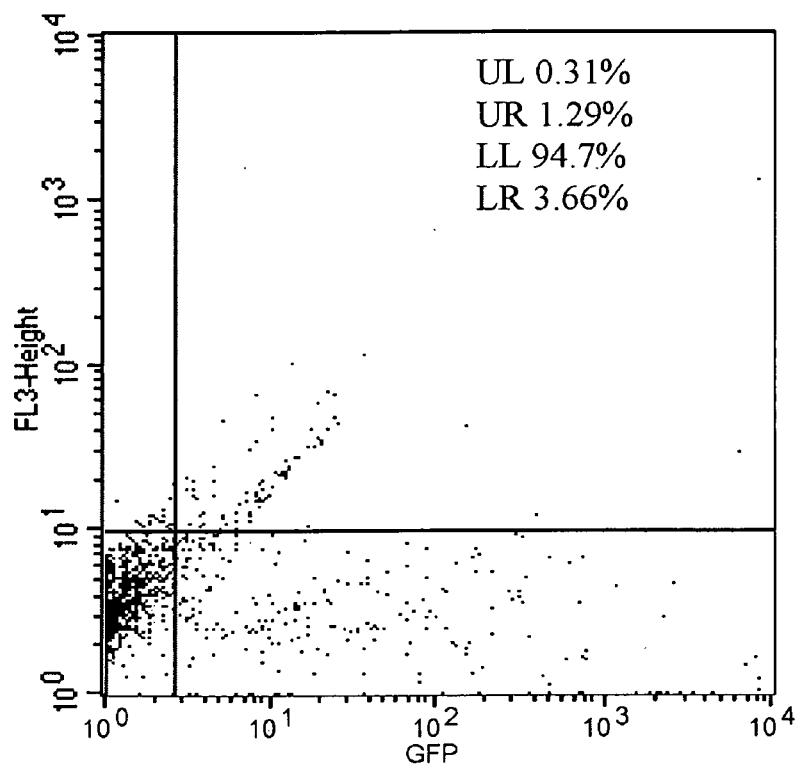
FIGS. 3A and 3B are scatter plots of FACScan analysis of GFP expression following cationic lipid-mediated DNA (FIG. 3A) and RNA (FIG. 3B) transfection in proliferation-inhibited 3T3 cells, showing an approximately 2-fold increase in the % of cells transfected by GFP RNA, relative to GFP DNA. Maximum % of GFP-expressing cells represents 12 hours and 48 hours post transfection time points for mRNA and DNA, respectively, as above. The scatter plot of FACScan analysis of GFP expression following RNA and DNA gene transfer is shown at the upper left.
Figure 3B:
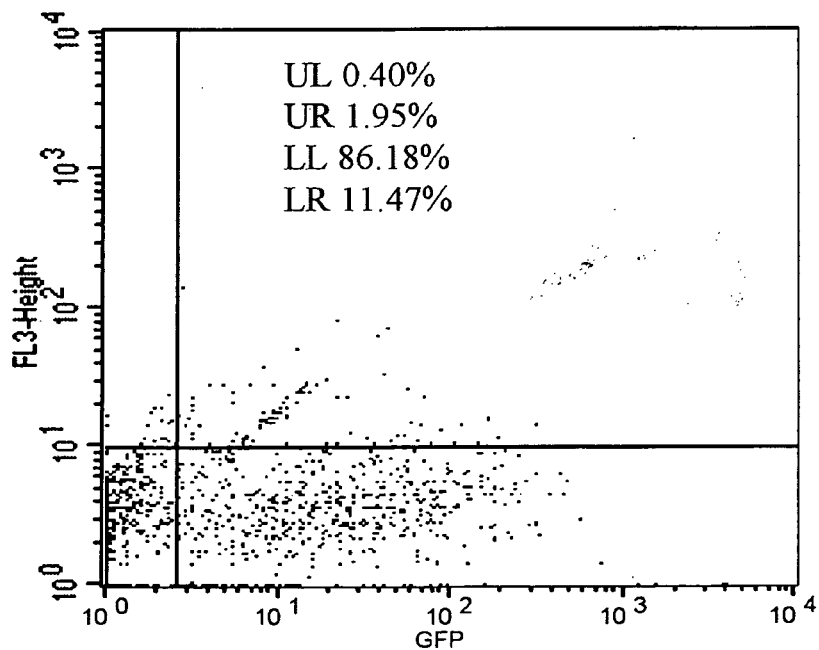
Figure 4:
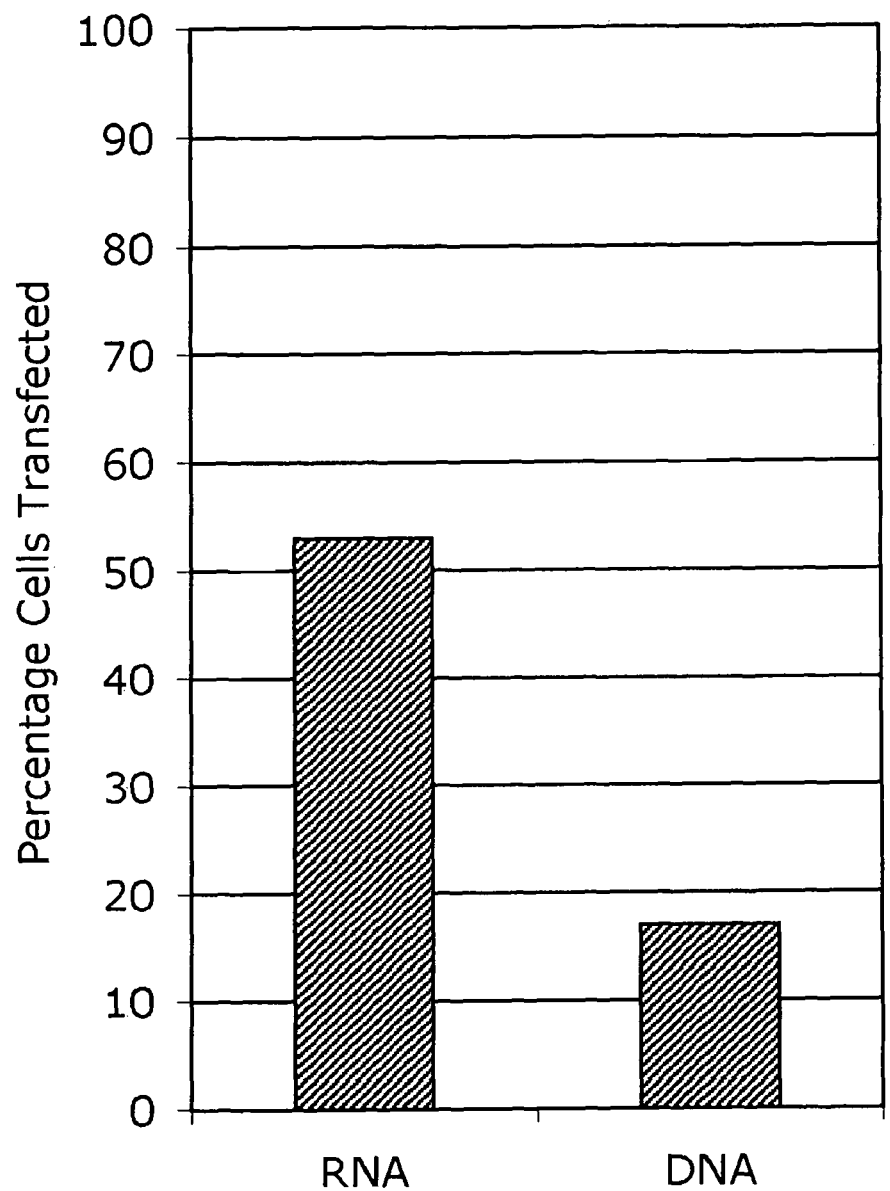
FIG. 4 is a graphical analysis of the FACScan analysis of cationic lipid-mediated RNA and DNA transfection in proliferation-inhibited NIH 3T3 cells, showing the increase in the % of cells transfected by GFP RNA, relative to GFP DNA. Maximum % of GFP-expressing cells represents 12 hours and 48 hours post transfection time points for mRNA and DNA, respectively, as above.

RNA and DNA Vector Delivery of GFP in Primary Mixed Neuronal Cells:

Previously optimized formulations of GFP-encoding RNA and DNA vectors (primary cultures of neurons and glial cells were incubated for 1 hour with lipid transfection formulations containing 1 μg of GFP RNA or DNA vector), were delivered to primary neurons in culture, and were analyzed by flow cytometry at 4, 8, 12, 24, and 48 hours following delivery. The results are again presented at the time point of maximum percentage of cells expressing GFP. As shown in FIG. 3, GFP RNA vectors transfected approximately 50% of primary neurons, as compared to approximately 24% of the neurons transfected with the GFP DNA vector in simultaneous transfections. Thus, there was an approximately 2× increase in the percentage of cells transfected by GFP RNA, relative to GFP DNA. The mean level of expression per cell, as measured by Cell Quest analysis of GFP intensity, was approximately 6× higher in DNA-transfected cells, relative to RNA-transfected cells.

Time Course of Luciferase Gene Expression after Delivery of DNA and RNA to Primary Neuronal Cells:

Next, luciferase-encoding DNA and mRNA vectors, that had previously been optimized for cationic lipid-mediated formulation, were delivered to primary cortical neurons and analyzed every hour for the first twelve hours, and then subsequently at 24, 36, 72, 80, and 96 hours following delivery. The delivery of mRNA to primary cortical neuronal cells resulted in a rapid onset of luciferase expression within 1 hour after transfection. Expression was transient, peaking at 5-6 hours post-transfection, and returning to base-line by 12 hours after transfection. By comparison, DNA delivery resulted in a much later onset of gene expression, not beginning until approximately three hours after transfection. DNA gene expression peaked at 36-48 hours after transfection, and the peak luciferase expression after DNA delivery was generally at least one order of magnitude higher than after RNA delivery, consistent with results with GFP vectors.

Figure 5A:
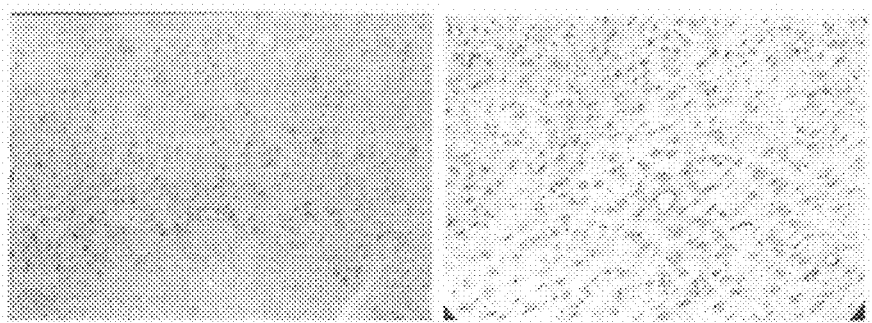
FIGS. 5A-5D demonstrate the widespread in vivo distribution, uptake and expression that were achieved after non-viral, cationic lipid-mediated gene delivery of luciferase-expressing mRNA vectors to the lateral ventricle of rat brain.
Figure 5B:
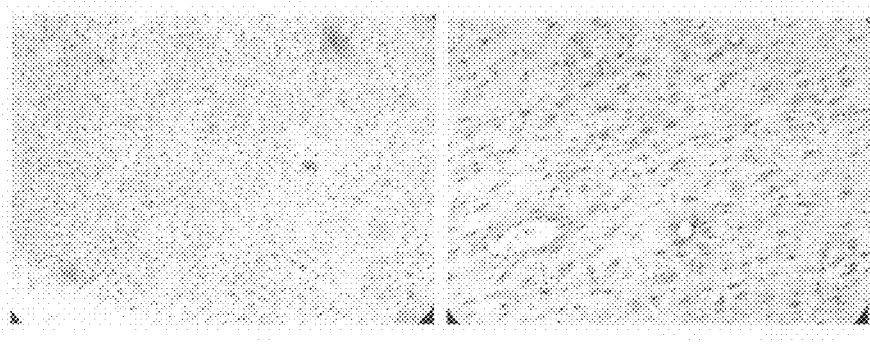
Figure 5C:
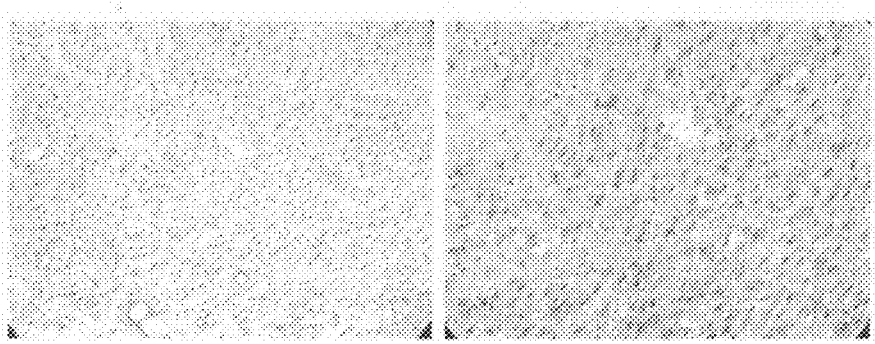
Figure 5D:
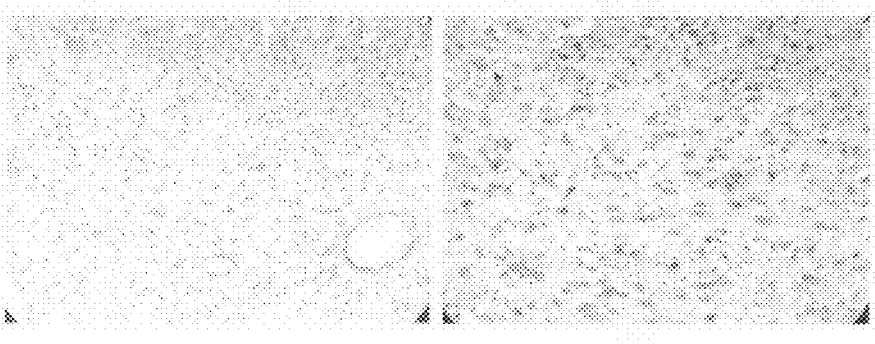

In Vivo Expression after Luciferase-Expressing mRNA Vector Delivery to Lateral Ventricle:

As an example of the widespread distribution, uptake and expression that were achieved after non-viral, cationic lipid-mediated gene delivery of mRNA vectors in an IACUC approved protocol, an optimized formulation of luciferase-encoding mRNA transcript were infused into the lateral ventricle of rat brain. FIGS. 5A and 5B demonstrate widespread expression from the two different experiments. FIG. 5A demonstrates widespread expression in rat cortex and subcortex after DAB immunohistochemistry. FIG. 5B demonstrates widespread subcortical expression. FIG. 5C depicts an area of FIG. 5B, see inset, at a magnification of 40×, in which cells that are phenotypically neurons are visible. FIG. 5D is from a section adjacent to that shown in FIGS. 5B and 5C stained simultaneously, using identical methods, in which the primary antibody has been omitted (negative control).

Example 2

Method for Conjugating Aminooxy-Ligands to Pre-Formed Lipoplexes

In the example that follows, a different cationic lipid, DMDK, was formulated and shown to effectively protect plasmid DNA from degradation from DNAses or from human cerebral spinal fluid. Following preparation of a lipoplex comprising plasmid DNA encoding luciferase or GFP using the methods described above, the preparation was incubated with commercially available DNAses, or with human CSF in vitro, and then the DNA was extracted from the lipoplex. To confirm that the DNA remained intact and of an appropriate length, the samples were run on an agarose gel, or they were used in transfections to demonstrate that the protein remain functional and could still be transcribed and translated.

Preparation of DMDK

Amino Acetal:

To a solution of a selected amine (1-(N-benzyl-N-methylamino)-2-propanone; 13.5 g, 76.1 mmol) in a 1:1 mixture of triethylorthoformate in ethanol (120 mL) was added p-toluenesulfonic acid (23.0 g, 121 mmol). The reaction mixture was heated to reflux. After 8 hours, the reaction mixture was cooled to room temperature, diluted with ethyl alcohol (EtOH) (300 ml) and washed successively with saturated aq. $Na_2CO_3$ (5×), water, brine, and then dried ($Na_2SO_4$). The solvent was removed by rotary evaporation and the residue was purified by column chromatography ($SiO_2$, hexane:ethyl acetate (EtOAc), 7:1) to afford the diethyl acetal (12.5 g, 65%) as a colorless oil; TLC (hexane:EtOAc, 7:1) $R_f$=0.26; $^1H$ NMR δ 7.20-7.36 (m, 5H), 3.58 (s, 3H), 3.49 (q, J=4.0 Hz, 4H), 2.54 (s, 2H), 2.27 (s, 3H), 1.41 (s, 3H), 1.15 (t, J=4.0 Hz, 6H); $^{13}C$ NMR δ 139.8, 128.9, 128.0, 126.7, 102.0, 63.4, 61.7, 55.5, 43.5, 21.7, 15.4; Anal. calculated for $Cl_5H_{25}NO_2$: C, 71.67; H, 10.02; N, 5.57. Found: C, 71.57; H, 9.94; N, 5.45. NMR was read using a Varion instrument at a strength of 300 MHz.

To a solution of the diethyl acetal (18.1 g, 72.0 mmol) in ethanol (60 ml) at room temperature was added 10% Pd/C (0.72 g). The suspension was placed under an atmosphere of hydrogen, and the reaction was stirred at ambient pressure. After 60 hours, the reaction mixture was filtered through a pad of celite and the ethanol removed by distillation. The amino acetal was obtained (7.96 g, 68%) by distillation of the residue under reduced pressure (bp 32-34° C., 2.5 mm Hg); $^1$H NMR δ 3.42-3.56 (m, 4H), 2.67 (s, 2H), 2.46 (s, 3H), 1.39 (s, 3H), 1.18 (t, J=7.2 Hz, 6H); $^{13}$C NMR δ 100.5, 57.3, 55.5, 36.8, 21.5, 15.3; Anal. calculated for $C_8H_{19}NO_2$: C, 59.59; H, 11.88; N, 8.69. Found: C, 59.24; H, 11.95; N, 8.53.

Diol:

To a solution of the amino acetyl (above) (7.64 g, 47.4 mmol) and $LiClO_4$ (5.04 g, 47.4 mmol) in ethanol (65 ml) was added 1,3-butenediepoxide (1.49 ml, 18.9 mmol). The reaction mixture was heated to 55° C. After 13 hours, the reaction solution was cooled and diluted with EtOAc (180 ml). The mixture was washed successively with saturated aq. $NaHCO_3$ (3×), water (2×), brine, and then dried ($Na_2SO_4$). The solvent were removed by rotary evaporation and the residue was purified by column chromatography ($SiO_2$, hexane:EtOAc, 2:1, saturated with $NH_4OH$, Rf 0.5) to afford the diol (6.03 g, 78%) as a colorless oil; IR 3460 cm$^{-1}$; $^1$H NMR δ 3.65 (m, 11-1), 3.48 (dq, J=9.4 Hz, J=2.5 Hz, 4H) 2.53-2.75 (m, 4H), 2.40 (s, 3H), 1.38 (s, 3H), 1.16 (t, J=9.4 Hz, 6H); $^{13}$C NMR δ 101.6, 69.0, 63.2, 62.3, 55.8, 44.5, 21.6, 15.5; Anal. calculated for $C_{20}H_{44}N_2O_6$: C, 58.79; H, 10.85; N, 6.86. Found: C, 58.99; H, 10.65; N, 6.85.

Dimyristyl Diether:

To a suspension of NaH (0.07 g, 2.94 mmol) and hexamethyl-phosphoramide (HMPA) (0.51 mL, 2.94 mmol) in dimethylformamide (DMF) (1 ml) at 0° C. was added dropwise via cannula a solution of diol 3 (0.20 g, 0.49 mmol) in DMF (1 ml). The reaction mixture was allowed to warm to room temperature over 1 hour, and then cooled to 0° C. before addition of a solution of myristyl iodide (0.80 g, 2.45 mmol) in DMF (2 ml). The reaction solution was maintained between 0° C. and 10° C. for 2.5 days, whereupon it was quenched by addition of saturated aq. $NaHCO_3$ (1 ml). The reaction mixture diluted with diethyl ether ($Et_2O$) (20 ml) and was then washed successively with saturated aq. $NaHCO_3$ (2×), water, brine, and then dried ($Na_2SO_4$). The solvent was removed by rotary evaporation and the residue purified by column chromatography ($SiO_2$) using Hex:EtOAc (12:1) saturated with $NH_4OH$ to afford the diether (0.24 g, 57%) as a light yellow oil; TLC (Hex:EtOAc, 4:1) Rf 0.72; IR 2920, 2852, cm$^{-1}$; $^1$H NMR δ 3.55-3.60 (m, 2H), 3.43-3.51 (m, 12H), 2.64 (dd, J=13.4, 5.3 Hz, 2H), 2.52 (s, 4H) 2.47 (dd, J=13.3, 5.8 Hz, 2H), 2.32 (s, 6H), 1.54 (m, 4H) 1.38 (s, 6H), 1.25 (s, 40H), 1.16 (t, J=7.0 Hz, 12H), 0.88 (t, J=6.8, 6H); $^{13}$C NMR δ 102.3, 77.8, 71.2, 63.1, 59.8, 55.7, 44.1, 32.1, 30.5, 29.6-29.9 (4 signals), 26.5, 22.9, 21.9, 15.7, 14.3; HRMS (CI/NBA) m/z calculated for $C_{49}H_{10}N_2O_6$ $[M+H]^+$ 801.7654. Found 801.7691.

Dimyristyl Diketone (DMDK):

To a solution of the dimyristyl diether (above) (0.25 g, 0.32 mmol) in acetone (3.5 ml) was added p-toluenesulfonic acid (0.13 g, 0.67 mmol) at room temperature. After 5 hours, the reaction mixture was diluted with $Et_2O$ (20 ml) and washed successively with saturated aq. $NaHCO_3$ (3×), water, brine, and then dried ($Na_2SO_4$). The solvents were removed by rotary evaporation and the residue was dissolved in methyl iodide (4 ml). The reaction was stirred 16 hours, whereupon the excess methyl iodide was evaporated in a fume hood using a steady stream of argon. The residue was dissolved in $CHCl_3$ and eluted through a column of DOWEX 1X8-400 ion-exchange resign (2.5 g) (Dow Chemical Co, Midland, Mich.). Before use, the Dowex resin was pre-cleaned with a volume (~10 ml) of water (2×), and a volume (10 ml) of methanol (MeOH) (2×). The collected eluent was concentrated, transferred to a centrifuge tube and then further concentrated to ~1 ml under a stream of nitrogen. The product was precipitated by the addition of $Et_2O$ (8 ml), collected by centrifugation, washed with another aliquot of $Et_2O$ (8 ml), and then collected and dried under vacuum to obtain DMDK (0.20 g, 83%) as a tan solid; $^1$H NMR δ 5.54 (d, J=17.7 Hz, 2H), 5.24 (d, J=17.7 Hz, 2H), 4.66 (m, 4H), 3.89 (m, 4H), 3.69 (m, 2H), 3.53 (s, 6H), 3.48 (s, 6H), 2.35 (s, 6H), 1.54 (m, 4H), 1.25 (s, 40H), 0.88 (t, J=6.5 Hz, 6H); $^{13}$C NMR δ 199.6, 72.6, 71.2, 68.7, 65.5, 52.9, 51.9, 31.8, 30.2, 29.3-29.6 (4 signals), 28.8, 28.7, 26.2, 22.6, 14.0; HRMS (Cl/NBA) m/z calculated for $C_{43}H_{84}N_2O_6^{2+}$ $[M]^{2+}$ 341.3288. Found 341.3291.

Formulation of DMDK:

DMDK (10 mg) was formulated with DOPE in a 1:1 ratio and dissolved in chloroform (3 ml). The chloroform was evaporated under helium leaving behind a thin film. The vial containing lipid/DOPE film was placed under vacuum for 3 hours, and then reconstituted with 5 ml of 150 mM NaCl to a final concentration of 3 mM. The aqueous solution was vortexed for 1 minute, and sonicated for 5 minutes at 50° C., repeated twice. The resulting cationic lipid can easily be labeled with a commercially available probe, such as Alexa Fluor 488, without sacrificing transfection efficiency. Moreover, in addition to fluorescent imaging applications, this same ligand can be used to rapidly and simply conjugate radioisotopes, imaging contrast agents, targeting moieties, or chemotherapeutics.

Nucleic Acid Vectors:

Luciferase and eGFP DNA vectors (pND.Luc and pND.eGFP, as above) contain the human CMV immediate early promoter (HCMV IE1) and CMV IE1 intron, and a multiple cloning site (MCS). The luciferase and eGFP coding sequences were inserted into the multiple cloning site followed by the RNA terminator/polyadenylation site derived from bovine growth hormone (BGH) (as described in the previous Example), in a pUCI9 replicon.

Transfection Protocol:

100 μl of Opti-MEM (Gibco Cell Culture Systems/Invitrogen, Carlsbad, Calif.) reduced serum medium was placed in a 2 ml microcentrifuge tube with 1 μl of 1 μg/μl DNA (pND-Luc). A second 2 ml microcentrifuge tube contained 100 μl Opti-MEM and 10.9 μl DMDK:DOPE formulation. Both tubes were allowed to stand at room temperature (RT) for ten minutes, and then the lipid was added to the tube containing the DNA.

After completing the incubation, the lipid/DNA formulations were applied to cell culture and allowed to incubate at 37° C. After 3 hours, the lipid/DNA formulations were aspirated off and replaced with FI2K medium (Gibco/Invitrogen) containing 10% fetal bovine serum and 1% L-Glutamine. 24 well plates containing Chinese hamster ovary (CHO) cells were plated at a density of 50,000 per well approximately 24 hours prior to use. Cell cultures were maintained in a 37° C. incubator and at 5% $CO_2$.

DNase Treatment:

Naked DNA and DMDK/DNA complexes were incubated at 37° C. for thirty minutes with 1 μl of RQ1 RNase-Free DNase and 10× Reaction Buffer (Promega, Madison, Wis.). One unit of RQ1 RNase-Free DNase (1 unit/μl) is defined as the amount required to completely degrade 1 μg of lambda DNA in 10 minutes at 37° C. in 50 μl of a buffered solution. After 30 minutes of incubation, aliquots were removed and used for transfection or phenol/chloroform extraction.

Incubation and transfection were also carried out in human CSF, obtained under an approved IRB protocol at the University of Pennsylvania, wherein CSF was collected under sterile conditions at the Hospital of the University of Pennsylvania during the normal course of pre-operative spinal anesthetic administration.

Phenol/Chloroform Extraction:

An equal volume of phenol/chlororform/isoamyl alcohol was added to the DNA solution. This solution was vortexed for 10 seconds, briefly centrifuged, and the aqueous layer removed and placed in a new tube. 1/10 volume of 3M sodium acetate was added and then vortexed. Next, 2.5 volumes of ice-cold 100% EtOH was added, vortexed and placed in a −70° C. freezer for 15 minutes. The solution was then microcentrifuged for 5 minutes at maximum speed, and the supernatant was removed. 1 ml of 70% EtOH (room temperature) was added, and centrifuged for 5 minutes at maximum speed. The supernatant was removed and the pellet dried. The dry pellet was then dissolved in 30 µl of distilled, deionized water (ddHOH) (Ausubel et al., *Current Protocols in Molecular Biology*, Supplement 59:2.1.2 (2004).

Gel Electrophoresis:

1% agarose gels were prepared using 1×TAE Buffer (Invitrogen, Carlsbad, Calif.) and UltraPure Agarose (Invitrogen). Gels were run in 1×TAE buffer at 90 volts for 1 hour, and imaged using a Kodak Digital Science EDAS 120 camera (Diagnostic Instruments, Sterling Heights, Mich.) and Kodak Digital Science ID software (Kodak).

Formulation of Alexa Fluor 488 Hydroxylamine:

1 mg Alexa Fluor 488 hydroxylamine (Invitrogen) was reconstituted in a total volume of 1 ml to form a 1 µg/µl solution. DMDK was optimized for incubation time and charge ratio. Optimization was carried out by varying the charge ratio from 6:1 to 14:1, and varying the incubation time in 15 minute intervals, up to 45 minutes, at room temperature. These experiments resulted in a 14:1 charge ratio and 30 minutes of incubation at room temperature (RT).

100 µl of Opti-MEM (Gibco/Invitrogen) reduced serum medium was placed in a 2 ml microcentrifuge tube with 0.5 µg of DNA (pND.Luc). A second 2 ml microcentrifuge tube was also prepared containing 100 µl of Opti-MEM and the appropriate amount of DMDK. Both tubes were allowed to stand at RT for 10 minutes, and then the lipid was added to the tube containing the DNA.

After 30 minutes incubation at RT the pH of the lipid/DNA cocktails was decreased to approximately pH 5 using 250 mM HCl. pH was determined using pHydrion Papers 4-9 (Micro Essential Laboratory, Brooklyn, N.Y.) pH paper. 1 µg of Alexa Fluor 488 Hydroxylamine was added the lipid/DNA cocktail and allowed to incubate at RT for 2 hours in a dark environment. After incubation with Alexa Fluor 488 hydroxylamine the pH of the cocktail was returned to pH 7 using 250 mM NaOH. Following incubation with Alexa Fluor 488 hydroxylamine and correction of pH, the lipid/DNA cocktail was applied to the cell culture and allowed to incubate at 37° C. After 3 hours lipid/DNA cocktails were aspirated off and replaced with F12K medium (Gibco/Invitrogen) containing 10% fetal bovine serum and 1% L-Glutamine. The cell culture was prepared 24 hours in advance of use, comprising Chinese hamster ovary (CHO) cells in 24 well plates at a density of 50,000 per well (determined by a Bright-Line Hemacytometer (Hausser Scientific, Horsham, Pa.). Cell culture was maintained in a 37° C. incubator, at 5% $CO_2$. Controls included transfection of CHO cells with DMDK and DNA per protocol above, and Alexa Fluor 488 hydroxylamine alone incubated per protocol above.

Results

DMDK Synthesis:

N-benzyl-N-methylamino ketone 1 (Scheme 1) was prepared according to a literature protocol and reacted immediately following its distillation with triethylorthoformate in ethanol to give the corresponding diethyl acetal composition. Subsequent hydrogenolysis of the benzyl group produced the amino acetal. Following the diepoxide cleavage procedure, established for synthesis of the commercial transfection lipid Tfx™ (Promega), (±)-1,3-butanediepoxide (Aldrich) was reacted with the amino acetal composition in the presence of lithium perchlorate to obtain the bis-adduct. The catatonic lipid component of the Tfx™ Reagents is covered by U.S. Pat. No. 5,527,928 (herein incorporated by reference) and assigned to The Reagents of the University of California. Each Tfx™ Reagent is formulated to stabilize and give high efficiency transfection in a variety of cell lines including: HeLa, HepG2, 293, K562, COS-7, CV-1, NIH/3T3, BHK, CHO, PC12, Sf9, smooth muscle, MCF-7 breast cancer, Retinoblastoma, and Primary, including neuronal cells and HUVEC.

The dialkylation of the diol of the amino acetal composition was sluggish. However, prolonged reaction of the diol with NaH and myristyl iodide in a DMF:HMPA mixture produced a modest yield of the dimyristyl diether. Acetal hydrolysis, amine quaternization and iodide-to-chloride counter-ion exchange smoothly produced the dimyristyl diketo lipid (DMDK) as shown.

Scheme 1

Scheme 1: Synthesis of keto lipid DMDK.

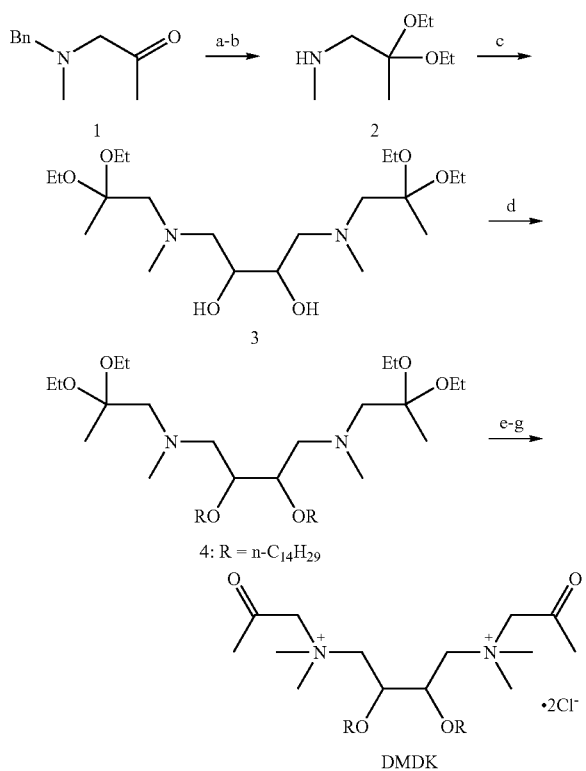

Conditions:
a) EtOH, $(EtO)_3CH$, TsOH, reflux, 8 hours, 65% (Ts refers to toluenesulfonic acid $(CH_3C_6H_4SO_2)$;
b) $H_2$, Pd/C, EtOH, 60 h, 68%;
c) 1,3-butanediepoxide, $LiClO_4$, EtOH, 55° C., 13 hours, 78%;
d) i. NaH, HMPA, DMF, 0° C. to RT, 1 hour;
ii. $CH3(CH2)13I$, DMF, 0° C. to RT, 2.5 days, 57%;
e) TsOH, acetone, rt, 5 h;
f) methyl iodide (MeI); room temperature, 16 h;

g) Dowex 1X8-400 (chloride exchange resin), 83% (3 steps).

Figure 6:
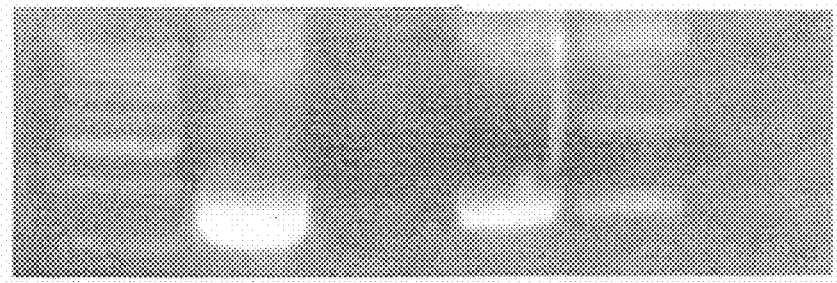
FIG. 6 is an agarose electrophoresis gel showing stability of vector DNA/DMDK lipoplex after incubation with DNAse and after incubation in human CSF in vitro. Lane 1=DNA ladder. Lane 2=pND.Luc alone. Lane 3=DNA alone treated with DNAse. Lane 4=DNA isolated from DMDK lipoplex. Lane 5=pND.Luc/DMDK lipoplex after incubation with DNase, followed by phenol/chloroform extraction. Lanes 6 and 7=the organic and aqueous layers, respectively, of phenol/chloroform extraction of pND.Luc/DMDK lipoplex after incubation in human CSF.

DNA Protection Assay:

The gel electrophoresis separation shown in FIG. 6 comprises:
Lane 1=a DNA ladder;
Lane 2=the plasmid DNA vector pND.Luc;
Lane 3=naked DNA (pND.Luc), treated with RQ1 RNase-Free DNase;
Lane 4=positive control: pND.Luc after phenol/chloroform extract to separate it from DMDK; Lane 5=pND-.Luc after incubation with DMDK, treatment with DNase and phenol/chloroform extract;
Lane 6=the organic layer of the phenol/chloroform extract of pND.Luc after incubation with DMDK in CSF;
Lane 7=the aqueous layer of the phenol/chloroform extract of pND.Luc after incubation with DMDK in CSF.

The agarose gel data demonstrated the expected integrity of the extracted DNA, with the exception of Lane 5. Lane 5 contains pNDLuc that had been first incubated with DMDK, then incubated with RQ1 RNase-Free DNase, and extracted with phenol/chloroform. Lane 5 contains three bands, instead of the two seen in the positive control, Lane 4. The ccc plasmid topology of DNA is the most compact structure, and therefore, is expected to be the most active form. The ccc-supercoiled form represents intact and undamaged DNA. However, if one strand is broken (nicked), the oc-form results. Linear forms are generated if both strands are cleaved at approximately the same position (Schleef et al., *J. Gene Med.* 6:S45-S53, (2004)). The inferior band in Lanes 4 and 5 represents the ccc-supercoiled monomer form of the DNA, whereas the superior band represents the oc-form. The middle band, seen only in Lane 5, may represent a ccc-supercoiled dimer form of DNA. Lane 6, containing a single band representing DNA incubated with DMDK in CSF, is clearly not as intense as the control or pND.Luc/DMDK DNA subjected to DNase. In addition the data from the enhanced luciferase assay also suggests that DNase in hCSF degraded some of the DNA.

Luciferase Assay:

Transfected cells (transfected with DMDK, and pND.Luc) were assayed using the standard protocol from the Enhanced Luciferase Assay (Becton Dickinson PharMingen, San Jose, Calif.), see description above under heading "*Time Course of Luciferase Expression in Primary Neurons after mRNA and DNA Transfections.*" Transduction/luciferase activity was measured in Relative Light Units (RLUs), e.g., by a commercial luminometer as above or by a scintillation counter, with the appropriate counting mode selected, e.g., a Beckman Coulter LS6500 scintillation system in the single-photon mode, or with a fluorometer, without the presence of filters that would absorb light emission.

Cells transfected with DMDK/pND.Luc emitted 22,030, 216 relative light units (RLU) measured in RLUs. Cells transfected with DMDK/pND.Luc, and then further incubated with RQ1 RNase-Free DNase (Promega), emitted 27,023, 812 RLUs. Cells transfected with DMDK/pND.Luc incubated in CSF emitted 12,367,732 RLUs.

Figure 7:
FIG. 7 depicts a fluorescent image of CHO cells transfected by Alexa Fluor 488-labeled lipoplexes.
Figure 8:
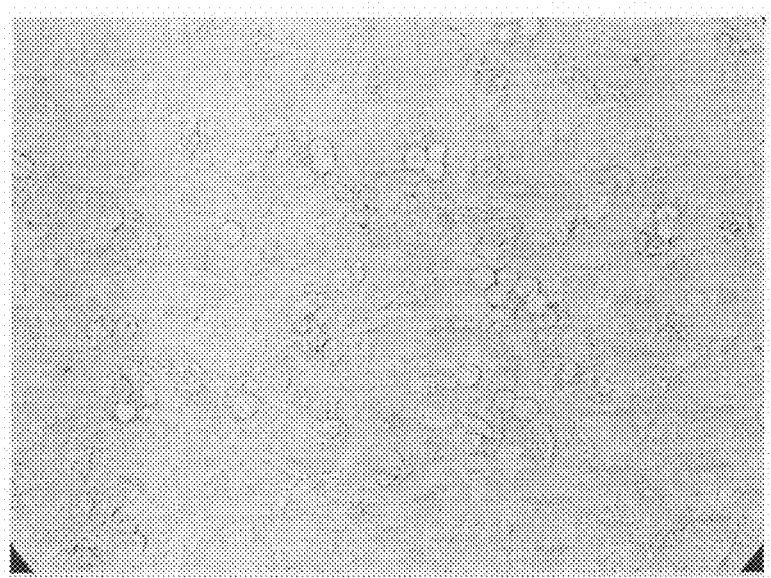
FIG. 8 depicts a Brightfield, identical to FIG. 2, of CHO cells transfected with DMDK, pND.Luc and labeled with Alexa Fluor 488 hydroxylamine.
Figure 9:
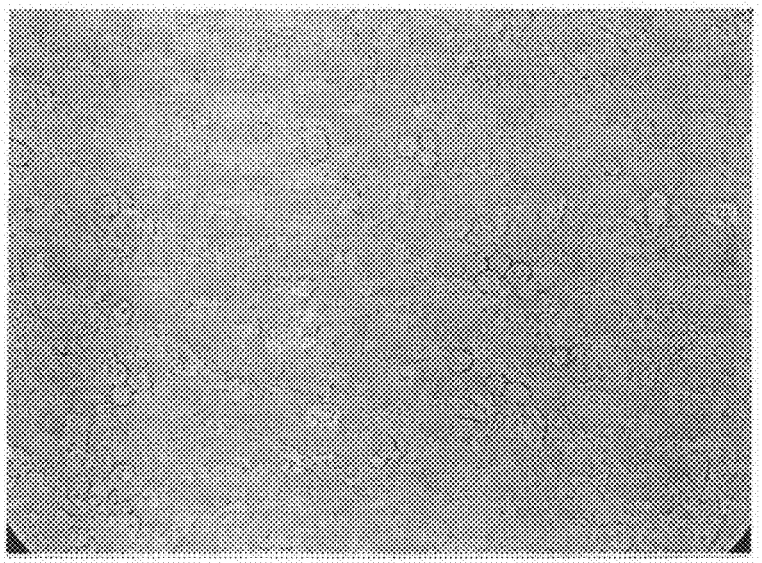
FIG. 9 shows a merger of the images seen in FIGS. 7 and 8.
Figure 10:
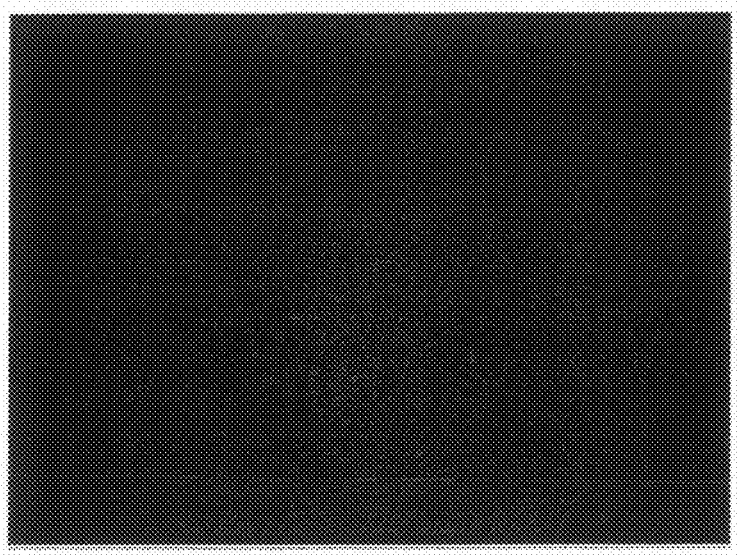
FIG. 10 depicts the negative control; CHO cells transfected with Alexa Fluor 488 hydroxylamine only. Alexa 488 fluorophore was not taken up by CHO cells in the absence of DNA/DMDK lipoplex.
Figure 11:
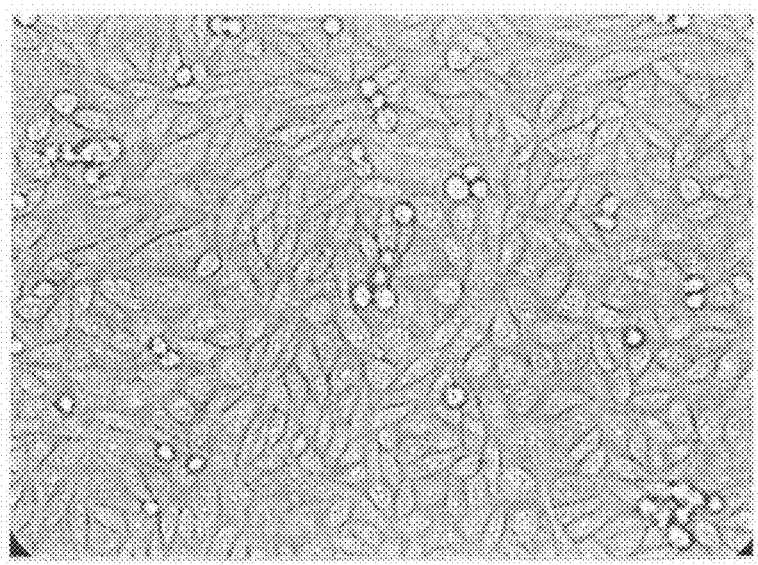
FIG. 11 depicts a Brightfield image, identical to FIG. 10, of CHO cells incubated with Alexa Fluor 488 hydroxylamine only, showing cell density for comparison.

Transfection and Imaging of CHO cells:

CHO cells were imaged 24 hours post transfection at 40× magnification, under FITC (FIG. 7) and Brightfield (FIG. 8) microscopy, using SPOT Advanced (Diagnostic Imaging), labeled with Alexa Fluor 488 hydroxylamine with exposure time manually set to 750 msec. FIG. 9 offers a merger of the images of FIGS. 7 and 8. The Enhanced Luciferase Assay was also carried out on the positive control, CHO cells transfected with DMDK and pND.Luc only, and compared to the same formulation labeled with an Alexa 488 fluorophore (FIG. 7). An average luminescence of 29,984,445 RLUs was measured, with a standard deviation of 327,712 (average of three wells of cells; graph not shown). CHO cells transfected with DMDK/pND.Luc labeled with Alexa Fluor 488 hydroxylamine emitted an average luminescence of 30,227,672 RLUs, with a standard deviation of 7829.5 (average of three wells of cells). FIG. 10 shows the negative control, wherein the cells were transfected with the Alexa 488 fluorophore alone, and FIG. 11 represents the identical Brightfield image of CHO cells transfected with Alexa Fluor 488 hydroxylamine only. Experiments were repeated, at least, in triplicate.

Example 3

Confirm Stabilization and Protective Effect of Congener Lipoplexed to Nucleic Acid Although experiments in human CSF (hCSF) (Anderson et al., supra, 2003) confirmed the effectiveness of cationic, lipid-based vectors (lipoplexes) for extending the protection to mRNAs against degradation by CNS RNases using the formulation of the present invention, data was not available to characterize and quantitate the extensive distribution, uptake, and cellular expression in the CNS of a human or primate subject of reporter genes, such as GFP. No data had been reported on the effect of the nucleic acid/lipid-based vector formulation on cells, such as neurons and Hsp70, the most highly inducible and neuroprotective of the heat shock proteins.

Tests were first designed to evaluate the efficacy of neuroprotection strategies, evaluate cellular toxicity and quantify the expression of Hsp70 and other gene sequences in the CNS and various other tissues over a time course following delivery of the DNA:lipid vector. These tests evaluated the effects following injections/infusions of exogenous gene sequences into the lateral cerebral ventricle, cisterna magna, and intra brain parenchyma in primate (monkey) brains to achieve widespread distribution and expression in the CNS of these species as measured by immunohistochemistry, fluorescent imaging (data not shown) and by DNA copy number (results shown in Table 1).

Following the methods outlined above for Example 1, 50 µg/kg of eGFP-expressing DNA vector in a 3:1 charge ratio with cationic lipid (MLRI) in 500-600 µl total volume was injected into free CSF in the cistern of an anesthetized primate. After recovery from the anesthetic, normal behavior was observed for various times in 15 primates over time at time points from 24 hours up to 6 months (pre, 24 hour; 48 hours; 72 hours; 1 week, 2 weeks, 4 weeks . . . 6 month), with 2 animals evaluated at almost every time point, except the 6 month point, following CNS delivery of eGFP DNA complexed with the non-viral, cationic lipoplex vectors. Blood was collected every two weeks until the animal was sacrificed and perfused under deep anesthesia, and CSF was collected at necropsy. About 50 tissues were biopsied and analyzed for delivered DNA:vector copies (Table 1; PPT data).

The Table and PPT data that shows copy numbers of DNA measures DNA copies per 50,000 cells by PCR, and is a direct measure of how many DNA copies reached and entered the cells of the various tissues that were biopsied and analyzed. DNA copy numbers are of extreme importance to since it demonstrates the effectiveness of each delivered vector and gene sequence.

Only relevant time points showing a change were tabulated for Table 1. Copy number was measured in all 50 tissues, but some of the results were combined when recorded in Table 1 when the effects were minimal, e.g., right and left diaphragm were combined into a single result, or right and left kidney, or multiple parts of the gut. As a result, not all results are shown.

Table 1 shows copy numbers of GFP DNA delivered to brain, spinal cord and ~50 other tissues in primate, after necropsy at indicated time points (all samples run for epsilon globin to confirm DNA presence). Safety and immune response data is not shown.

Samples were thawed immediately before assay, and either 50 µl of standard or sample was added to each well. Beadlyte Beads were sonicated for 15 seconds and diluted to 1× in Beadlyte™ Cytokine Assay Buffer. 25 µl of this bead mix was then added to each well. The plate was covered, vortexed at low speed for 30 seconds, and incubated overnight on a plate shaker at 2-8° C. The Beadlyte™ Biotin Reporters were diluted to 1× in Beadlyte™ Cytokine Assay Buffer. 25 µl of

| eGFP/ 50,000 cells | 24 hrs | 24 hrs | 48 hrs | 48 hrs | 72 hrs | 72 hrs | 1 week | 2 weeks |
|---|---|---|---|---|---|---|---|---|
| animal # | 34911 | 32551 | 34914 | 35085 | 35090 | 35201 | 35030 | 35035 |
| Date | Jul. 12, 2004 | Aug. 6, 2002 | Jul. 12, 2004 | Feb. 10, 2005 | Feb. 11, 2005 | Feb. 17, 2005 | Apr. 7, 2004 | Apr. 7, 2004 |
| Cerebrum | 1,693,449 | 1,178,036 | 97,123 | 5,526 | 261 | 44 | 4,208 | 120 |
| Cerebellum | 1,606,513 | 181,237 | 27,238 | 9,569 | 740 | 268 | 1,355 | 300 |
| Spinal cord | 76,157,575 | 1,499,552 | 10,009,461 | 1,702,030 | 464 | 3,248 | 33,822 | 110,000 |
| Spleen | 0 | 1 | 54 | 3 | 0 | 0 | 0 | 0 |
| Liver | 494 | 25 | 38 | 5 | 1 | 0 | 0 | 0 |
| Heart RV | 1,170 | 593 | 3,677 | 0 | 0 | 0 | 0 | 0 |
| Heart LV | 384 | 0 | 350 | 0 | 0 | 0 | 14,942 | 0 |
| Pericardium | 789 | 46 | 381 | 16 | 185 | 0 | 0 | 0 |
| Aorta | 669 | 0 | 914 | 35 | 22 | 0 | 0 | 100 |
| Trachea | 0 | 0 | 39 | 0 | 0 | 605 | 0 | 0 |
| Esophagus | 125 | 86 | 11 | 2 | 0 | 14 | 0 | 0 |
| Kidney | 28 | 0 | 15 | 3 | 1 | 0 | 0 | 0 |
| Lymph node | 6 | 0 | 5 | 0 | 13 | 0 | 0 | 0 |
| Lung caudal | 61 | 0 | 524 | 0 | 285 | 4 | 0 | 13 |
| Diaphragm | 167 | 0 | 21 | 0 | 31 | 26 | 0 | 105 |
| Colon | 0 | 0 | 3 | 0 | 0 | 0 | 0 | 0 |
| Gonad | 0 | 0 | 28 | 0 | 0 | 0 | 0 | 0 |
| Omentum | 54 | 0 | 10 | 4 | 810 | 18 | 0 | 0 |
| Skin | 35 | 0 | 0 | 106 | 772 | 337 | 0 | 0 |
| Pancreas | 1 | 0 | 0 | 0 | 0 | 0 | 0 | 0 |
| Adrenal | 7 | 0 | 7 | 3 | 6 | 0 | 0 | 0 |
| Peritoneum | 20 | 0 | 3 | 0 | 18 | 5 | 0 | 0 |
| Bladder | 7 | 0 | 9 | 0 | 9 | 0 | 0 | 0 |
| Stomach | 2 | 0 | 0 | 0 | 2 | 1 | 0 | 0 |
| Duodenum | 0 | 0 | 4 | 0 | 0 | 0 | 0 | 0 |
| Jejunum | 0 | 0 | 8 | 0 | 2 | 0 | 0 | 0 |
| Muscle | 110 | 0 | 0 | 0 | 9 | 4 | 0 | 0 |
| Bone marrow Blood | 6 | 0 | 17 | 0 | 0 | 0 | 0 | 0 |

49 tissue locations biopsied and assayed

Copy numbers below several hundred probably are an artifact of the PCR method to measure the copy numbers. There are some copy numbers in tissues outside of the CNS, particularly at the early time points (24 and 48 hours) as would be expected. The significance of the copy numbers in heart, for example, is unknown. The significance of the data, however, is that the copy numbers rapidly diminish (i.e., showing good transient expression), the numbers in the CNS are extremely high, even relative to lenti viral delivery by Tarantal et al. at UC Davis. Moreover, there is very little escape outside of the CNS, which is critical to effective use of the nucleic acid delivered to the brain, and significantly, there is no escape into germ line tissues (this is a concern in the delivery of any DNA, as incorporation into germ line tissues, gonads, would mean that the gene changes could be passed to offspring, rather than expression in only the individual animal to which it was administered).

To determine the cytotoxic effect, if any, of the lipoplex vectors on the CSF in primates, multiple immune and inflammatory markers from blood and CSF were evaluated as follows. The cytokines were measured by an assay that required a label onto each specific immune factor. Cytokine assays were carried out by Beadlyte® Multiplex Testing Service (Upstate USA; Charlottesville, Va., USA) Standards were prepared by resuspending the Human 26-plex Multi-Cytokine Standard (Cat. No. 47-030) with 1 ml of Beadlyte™ Cytokine Assay Buffer. A 12 pt serial dilution (1:2) was made.

this solution was then added to each well. The plate was covered mixed by vortex at low speed, and then incubated 1.5 hours in the dark at room temperature. Beadlyte™ Streptavidin-Phycoerythrin was then diluted 1:25 in Beadlyte™ Cytokine Assay Buffer, and 25 ml of diluted Beadlyte™ Streptavidin-Phycoerythrin was added to each well as a second marker for immune response. The plate was covered and mixed by vortex at low speed, and then incubated 30 minutes in the dark at room temperature. The plate was aspirated and resuspended in 125 ml of Beadlyte™ Cytokine Assay Buffer and results were read on Luminex® 100™ Instrument set-up to read the selected beads for the desired analytes. 50 bead events were selected and the sample volume was at 80 µl.

For the multiplex cytokine assay, the measured cytokines included: interleukin-1β (IL-1β, IL-2, IL-6, IL-8, IL-12 (p40), monocyte chemoattractant protein-1 (MCP-1), macroph inflammatory protein-1α (MIP-1α), regulated upon activation, normal T cell expressed and secreted (RANTES), tumor necrosis factor-α (TNF-α), interferon-γ (IFN-γ), and granulocyte-macrophage colony stimulating factor (GM-CSF).

For the analysis, the concentrations of analytes in these assays were quantitated using standard curves. A regression analysis was performed to derive an equation that was then used to predict the concentration of the unknown samples. Statistical differences in measured values were analyzed using either a two sample t-Test assuming unequal variances, or a multi-sample ANOVA. P values less than 0.05 were considered statistically significant.

A diverse cytokine profile of CSF of Rhesus Macaques was found following injection. The 11 investigated plasma cytokines were sorted into four functional groups: the 'cytotoxic cellular cytokines' (IL-1β, IL-2, IL-12p40, IFN-γ and TNF-α); the 'humoral cytokines' (IL-6); the 'growth factors' (GM-CSF), and the 'chemokines' (IL-8, MIP-1a, MCP-1, and RANTES). In each group, the CSF cytokine levels were compared among varying time points measured from the initial injection. Individual cytokine levels were also compared with white blood cell (WBC) levels to determine if an elevation of WBC (>10.8×10$^3$; an index of WBC count greater than normal) affects individual cytokine levels.

In the 'cytotoxic cellular cytokines' group, IL-1β (P=0.017) was significantly elevated, as were the WBC levels, while IL-12p40 (p=0.057) demonstrated a trend of elevation with elevated WBC levels. There was no significant difference between any cytotoxic cytokine levels with respect to time of injection.

For the cytokine that drives the humoral immune response, the level of IL-6 was not affected by elevated WBC levels. When comparing CSF IL-6 levels at varying time points (pre, 1 day, 2 day, 3 day, 4 day, 5 day, 8 day, and 11 day) there was no significant difference between the time points (p=0.418). However, if the later time points day 3 to day 11 are combined prior to ANOVA analysis, there was a significant difference between time points (p=0.045).

The comparison of the CSF levels of 'growth factors' revealed no significant difference of GM-CSF levels at varying time points, nor was GM-CSF levels affected by elevated WBC levels. For CSF 'chemokine' levels, only MIP-1α (p=0.023) was significantly elevated and IL-8 (p=0.0728) showed a trend of elevation, with elevated WBC levels. There was no significant difference in any CSF 'chemokines' levels when individual time points from injection were compared.

Thus, there did not appear to be any specific immune response to injection of the DNA:lipid vector, but there was non-specific immune response that correlated with white blood cell levels, often a marker for stress or infection. There was no significant difference seen at any of the time points, including the time 0, which is when the animals were first injected. The correlations appear to be solely with WBC, which is not related to the non-viral lipoplex delivery and expression.

Accordingly, the data demonstrate that transfection with the cationic lipid complexes rapidly achieved widespread delivery of exogenous, cationic lipid-protected, intact DNAs, without the immunogenic risks incurred by the use of viral vectors.

Example 4

Whole Animal Imaging After Transient Non-Viral, Gene Delivery to the Rat Central Nervous System Based upon the inventors' previously developed gene delivery system using non-viral vector:cationic lipid complexes (lipoplexes), the following experiments were conducted to measure and demonstrate the time course of transient luciferase expression in the intact, whole animal after delivery of the non-viral vector:cationic lipid complex (containing DNA and mRNA, respectively) to the CSF of rats. First the luciferase gene delivery was optimized in vitro using novel cationic lipids and lipid:DNA or lipid:mRNA formulation methods, and then gene expression in vivo was followed in terms of luciferase activity and by extrapolation using noninvasive optical bioluminescence imaging. Standard immunohistochemistry techniques were used to confirm widespread expression of the reporter gene in the CNS of injected rats.

Materials and Methods followed essentially those of Example 1, unless described specifically.

Nucleic Acid Vectors.

The pND.LUC expression vector was used for luciferase DNA experiments, carrying the cDNA sequence for firefly luciferase from the firefly *Photinus pyralis* (pGL2I+, Promega, Madison, Wis.) as described elsewhere herein and in (Hecker et al., supra, 2001), as are all vectors, lipids, and assays. β-globin luciferase and Gallie TMV-Omega vectors were used for luciferase mRNA experiments, described elsewhere and herein.

Lipids and Formulation of Lipid:

Nucleic Acid Complexes. After comparisons, the cationic lipid that performed best in vitro was used for further transfections in vitro and in vivo. This lipid was developed by Nantz et al., supra 1995, 1996. Briefly, the lipid was prepared by adding chloroform to dry MLRI (dissymmetric myristoyl (14:0) and lauroyl (12:1) Rosenthal Inhibitor substituted compound formed from the tetraalkylammonium glycerol-based DORI) and mixed with dioleoylphosphatidyl-ethanolamine (50:50 DOPE) in chloroform. cDNA:lipid complexes or mRNA:lipid complexes were formed by combining the described lipid preparation with plasmid DNA or with transcribed mRNA, respectively, to create a 3:1 lipid:nucleic acid charge ratio.

For in vitro experiments, plasmid DNA or mRNA and MLRI were added to Opti-Mem solution (see Example 1). Mixtures for in vivo experiments contained only DNA or mRNA solution and lipid, in order to minimize injected volume. Mixtures were incubated at 37° C. for 45-60 minutes prior to transfection in vitro and for 30 minutes prior to delivery in vivo. In vivo delivery to the rat CSF required approximately 15 minutes after the needle localization into the lateral ventricle or cisterna magna, resulting in a total effective incubation time of 45-60 minutes.

In Vitro Transfection.

CHO-K1 cells were plated as in Example 1 and then returned to the 37° C. incubator.

Assay of In Vitro Luciferase Activity.

Prior to in vivo delivery of the pND.Luc lipid or mRNA: lipid complex, every preparation of our vector was tested for biologically activity by successful transfection of cell cultures. Luciferase activity in transfected cells was assayed using the Enhanced Luciferase Assay Kit as described in Example 1. Previous in vitro work by the inventor's laboratory showed that the peak after DNA transfection occurs at 48 to 72 hours, and at 5-7 hours after mRNA transfection.

In Vivo Delivery and Transfection.

In vitro transfections were first performed to confirm and optimize luciferase activity. Under Approved Protocols, rats were anesthetized with isoflurane in an induction chamber (Stoelting, Co, Woodale, Ill.), then given an intraperitoneal injection of a mixture of ketamine (75 mg/kg), xylazine (10 mg/kg) and acepromazine (0.75 mg/kg). Rats were then mounted in a stereotactic frame (Stoelting, Co). Anesthesia was maintained in spontaneously breathing animal subjects (anesthetized male Sprague Dawley rats, Charles River Laboratories, Mass.) with inhaled isoflurane through a nose cone (manufacturer) with 1.0 l/min supplemental $O_2$. A 24-gauge spinal needle was connected to a 250 μl Hamilton syringe mounted in a syringe pump via PE-20 tubing. The pND.Luc: MLRI or mRNA luciferase:lipid complexes were then delivered to either the lateral ventricle or cisterna magna of the animal. Two sites of injection were used to access the CSF of rats in order to identify differences in luciferase expression and distribution patterns that may be site specific.

After sterile prep, the skull was exposed and a burr hole was made over the injection coordinates for lateral ventricle delivery. The spinal needle was advanced to coordinates 0.9-1.0 mm posterior, 1.5 mm lateral of midline relative to Bregma, and a depth of 3.5-4.0 mm. 50 mg/kg of DNA or mRNA vector encoding firefly luciferase was complexed with MLRI as described above and the formulated lipid:nucleic acid complex was slowly infused over 10-15 minutes into the lateral ventricle.

For cisterna magna delivery, a skin incision was made over the Atlanto-occipital joint and the muscle overlying the joint was moved by blunt dissection to expose the ligaments over the cranial suture. The spinal needle connected to the Hamilton syringe was advanced into the ligament overlying the suture until CSF was obtained. The lipid:nucleic acid complex was infused over 10-15 minutes.

After completion of the infusion to either lateral ventricle or cisterna magna, the needle used for delivery was kept in place for 10 minutes prior to withdrawal. The surgical site was sutured; the animal was removed from the stereotactic frame and allowed to recover. Animals were closely monitored for signs of discomfort, toxicity, or neurologic injury.

In Vivo Imaging.

The experimental results depend on an indirect measure of the presence of active luciferase in vivo. Emitted light is one product of the ATP-requiring luciferase cleavage of the substrate luciferin, as a result, the time course of the luciferase activity in vivo was followed by the detection of emitted light. Cleavage of luciferin and the resultant light emission occurs rapidly, peaking minutes after the intravenous (IV) injection of luciferin. Due to the kinetics of this reaction in vivo, it was important to measure light emission at the same time after each luciferin injection, in order to quantify the time course of gene expression. Therefore, the peak and duration of luciferase activity after each IV injection of luciferin was determined in rats by rapid data acquisition at 1-2 min intervals. Every 24 hours after injection of the vector, the rats were injected intravenously with luciferin, and enzyme activity was followed by IVIS imaging every 2-5 minutes until light emission was no longer detected over background. Using the IVIS imaging software, regions of interest (ROIs) were created over areas of intense light emission and the photons emitted at each time point were quantified.

Because there was some variability in the time of peak luciferase activity, multiple IVIS images were taken after every IV luciferin injection in subsequent experiments. Animals were imaged every 2-3 minutes until a clear peak of light emission was detected. ROI data was collected at the peak of light emission for each 24 hour time point measurement of luciferase expression, or every 1-2 hours after mRNA delivery. The Xenogen IVIS 100 (Xenogen Corp, Alameda, Calif.) was used to image the animals after vector delivery. An anesthetized animal was placed in the light tight imaging box, and the animal was imaged to obtain a background level of light emission. Next, the enzyme substrate, luciferin, was injected intravenously at a concentration of 150 mg/kg and luciferase activity followed over time by light emission detection. In additional experiments, luciferin dose was also varied, to arrive at a balance between luciferase signal, luciferin expense, and luciferin buffer salt load to the animals. A cooled CCD camera of the IVIS 100 system was used to detect photons emitted during the enzymatic breakdown of the substrate luciferin by luciferase. The peak expression and duration of luciferase activity was measured.

A light image of the anesthetized, spontaneously breathing animal in the imaging system was taken first. Light emission (photons) was then detected over a 1 minute period using medium binning. Anatomical localization was obtained by the superposition of the luminescent image over the light image. Each image (i.e., time point) is, thus, a composite of a photograph of the animal and the acquired luminescent image. Regions of interest were created to include the location of the most intense signal in the CNS both before and after delivery of the substrate, and background counts were subtracted from signal counts.

Tissue Preparation for the Reporter Enzyme Localization and Immunohistochemistry Luciferase Immunochemistry in Rat Brain.

After in vivo imaging on the day of sacrifice to confirm the peak in luciferase expression, the animals were first deeply anesthetized. After catheterization of the left ventricle, animals were then perfused with chilled PBS, and then with pre-cooled freshly made 4% PBS buffered paraformaldehyde at 35 ml/1 minute for 30 minutes, for a total of 1,000 ml. The inferior vena cava at the inferior level of liver was transected to allow complete washout of blood. Following perfusion, the whole brain was removed by way of craniotomy. The brain was further fixed in 4% PBS buffered paraformaldehyde at 4° C. overnight. If the brain was not immediately cryostat sectioned the following day, a beaker containing 300 ml 2-methyl butane (isopentane) was prepared in the hood. The beaker was immersed in dry ice and 100% ethanol in a bucket for 20 minutes, the rat brain was rapidly frozen in the chilled 2-methylbutane, wrapped up in foil, and kept at −80° C. until further processing.

The day before cryostat sectioning the brain was moved from −80 to a −30° C. freezer overnight. The brain was mounted on the Microm HM450 (Microm International, Richard-Allen Scientific, Kalamazoo, Mich.) platform and embedded in OCT surrounded with powdered dry ice. After minor blocking, the entire brain was cut into 30 micron sections. Brain sections were stored 1 section/well in a series of ten 24-well culture plates with 1 ml/well of 0.1 M phosphate buffer with 20% glycerol. The brain sections were stored until further processing at −80° C. as serial plates in which each plate contained every tenth section throughout the entire brain.

To determine immunohistochemistry, the rat brain sections were rapidly thawed from −80° C., and transferred to 24-well plates. Sections were gently shaken in 1×PBS for 5 minutes at room temperature to wash off the glycerol. Rinsing was repeated 3× in PBS, then 3% $H_2O_2$ was added for a 15 minute incubation at room temperature with gentle shaking to eliminate endogenous peroxidase, followed by a further 3 rinses in PBS. The sections were subsequently incubated for 1 hour with gentle shaking in 1×PBS-buffered blocking buffer containing 10% normal goat serum (Vector Laboratories), and 0.5% Triton 100 X-100 (Sigma). A polyclonal goat anti-luciferase antibody (Promega) diluted to 20 μg/ml (1:50 dilution) in blocking buffer was used to replace the blocking buffer, and the plate was incubated at 4° C. overnight. A negative control was incubated in the absence of the primary antibody. Peroxidase conjugated horse anti-goat secondary antibody (Vector Laboratories) was diluted 5 ug/ml (1:200 dilution) in 1×PBS. At the end of incubation with primary antibody, sections were rinsed 5 times in 1×PBS, and then incubated for 1 hour at room temperature with secondary antibody. After washing, bound secondary antibodies were detected by incubating for 3 minutes with 3,3'-dianminobenzidiine (DAB) from the DAB substrate kit for peroxidase (Vector Laboratories). See detailed description in Example 1.

DAB produces a brown color indicating positive binding of the peroxidase conjugated secondary antibody. Finally, the brain sections were mounted on glass slides, dried overnight at room temperature, and lightly counterstained with hematoxylin.

Time Course of Luciferase Activity after cDNA:

lipid Delivery to the CSF. Prior to in vivo delivery of the pND.Luc:lipid complex, each preparation of the vector was tested as above, and determined to be biologically active by successful transfection of cultured cells. After confirmation of biological activity, the vector:lipid complex was injected into the CSF of rats either via the lateral ventricle or the cisterna magna. Luciferase activity in the cells was followed over time by in vitro assay of enzyme activity, as described above and in Example 1, and counts were plotted over time after substrate delivery. A few animals were imaged at hourly time points after vector delivery. The hourly images taken after in vivo cDNA:lipid vector delivery showed that luciferase activity can be detected over rat brains within as soon as 2 hours after cDNA:lipid vector delivery (data not shown) in repeated experiments with multiple animals. Peak luciferase activity occurs 2-5 minutes after IV luciferin injection and is detectable over background for approximately 40-50 minutes.

Figure 12A:
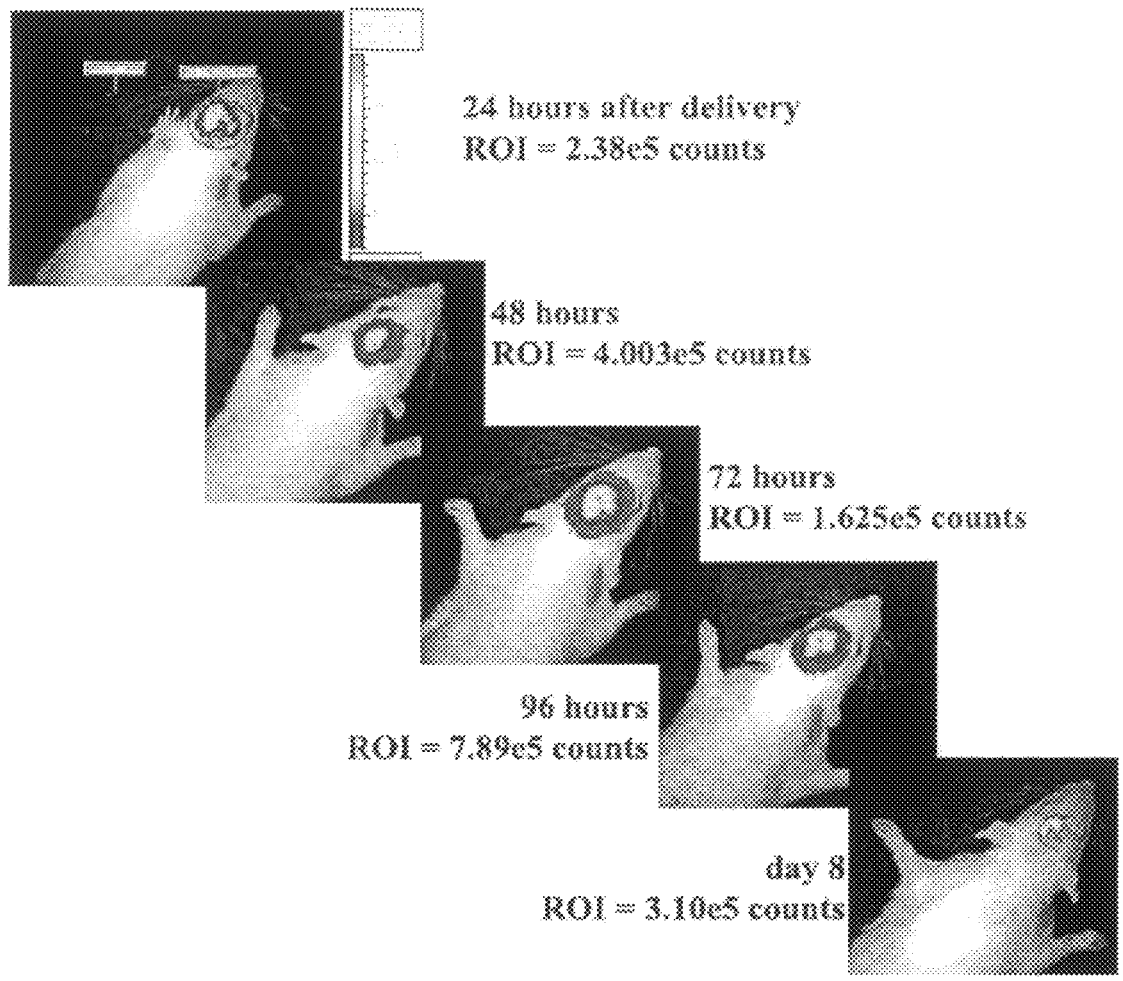
FIGS. 12A and 12B provide a series of bioluminescent images showing luciferase activity over a time course of luciferase activity and expression (FIGS. 12A and 12B).
Figure 12B:
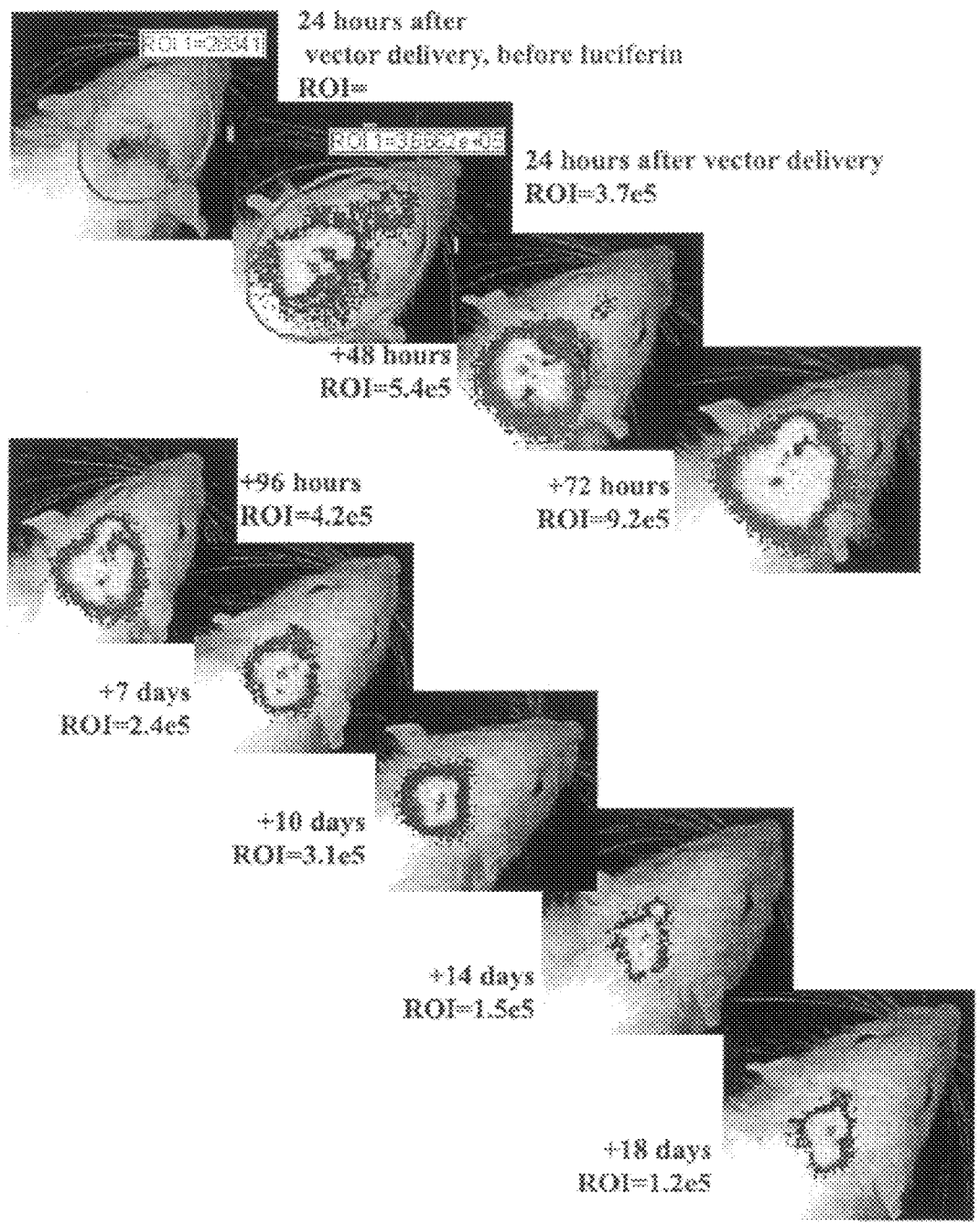

Bioluminescent imaging was continued at 24 hour intervals to follow the time course of luciferase activity and expression (FIGS. 12A and 12B). When representative data was compared from time course experiments after left lateral ventricle and cisterna magna injections, respectively, the light signal clearly crosses the midline of the skull, although luciferase activity was greater on the left than the right side of the animal's head. By 72 hours, light emission seemed to be symmetric over the CNS, demonstrating that the vector is transported through the ventricular system of the brain to allow for widespread distribution and uptake. As the time course continued and the signal diminished, luciferase activity remains longest in the region closest to the injection site.

Widespread distribution of luciferase activity was also seen after cisterna magna injection of the cDNA:lipid complex. Once again, more luciferase activity is seen near the site of injection at early and late time points. Comparison of the 72 hour images in FIGS. 12A and 12B show that after cisterna magna injection, enzyme expression is detected over the entire rat brain. In contrast, no light signal (and thus no enzyme activity) is seen over the cisterna magna and rat cerebellum 72 hours after a lateral ventricle delivery of the vector:lipid complex, which may reflect CSF flow and mixing.

Figure 13:
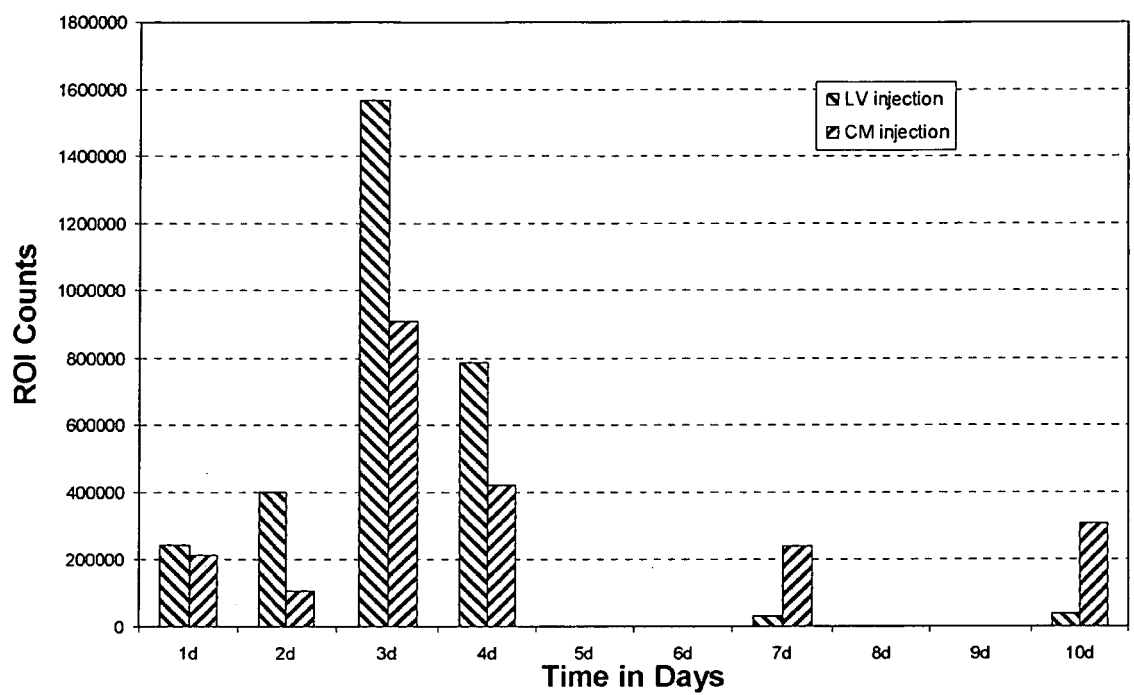
FIG. 13 shows a comparison of representative data from time course experiments delivery of lipoplexed luciferase cDNA to the CSF.

ROIs were drawn around the captured light signal in each image, and photon counts were recorded. FIG. 12A-12B further show the ROI photon counts plotted over time from 3 injected rats. The quantity of light emitted, and therefore the level of luciferase activity, was variable. However, the overall time course of enzyme activity, and thus gene expression, was consistent among animals, with a consistent peak of DNA expression at 72 hours. In general, luciferase activity then decreased rapidly, although a low level of activity remained detectable for several days after injection. See FIG. 12B. Typically, luciferase activity became undetectable by bioluminescence imaging 10-20 days after injection. FIG. 13 shows a graphic summary showing a luciferase activity time course after cDNA delivery to the CSF.

Time Course after Parenchymal Vector Complex Delivery.

For comparison with the effect of the CSF injections, the luciferase carrying vector:lipid complex was injected directly into parenchyma of the rat brain. Subcortical injections were made adjacent to the left lateral ventricle of the animals. Light emission after 24 hours remained directly over the site of injection. At 72 hours, however, some photon signal was seen across the rat head's midline, but the signal is not as widespread as that seen after CSF delivery. The distinctly different patterns of light emission seen after parenchymal versus CSF delivery of the vector further confirms that the CSF injections (performed either blind or by stereotactic coordinates) reached their target and provide widespread, transient expression.

ROIs were created over the emitted light for each time point and the photons in each ROI quantified. Light emission, and thus luciferase activity demonstrating exogenous DNA expression, continued to increase over the 72 hours that this animal was followed, consistent with the previous time course results. Similar results with a peak at 5-7 hours and lower intensity were seen in animals injected with the mRNA luciferase vectors (data not shown).

Luciferase Immunofluorescence.

Figure 14:
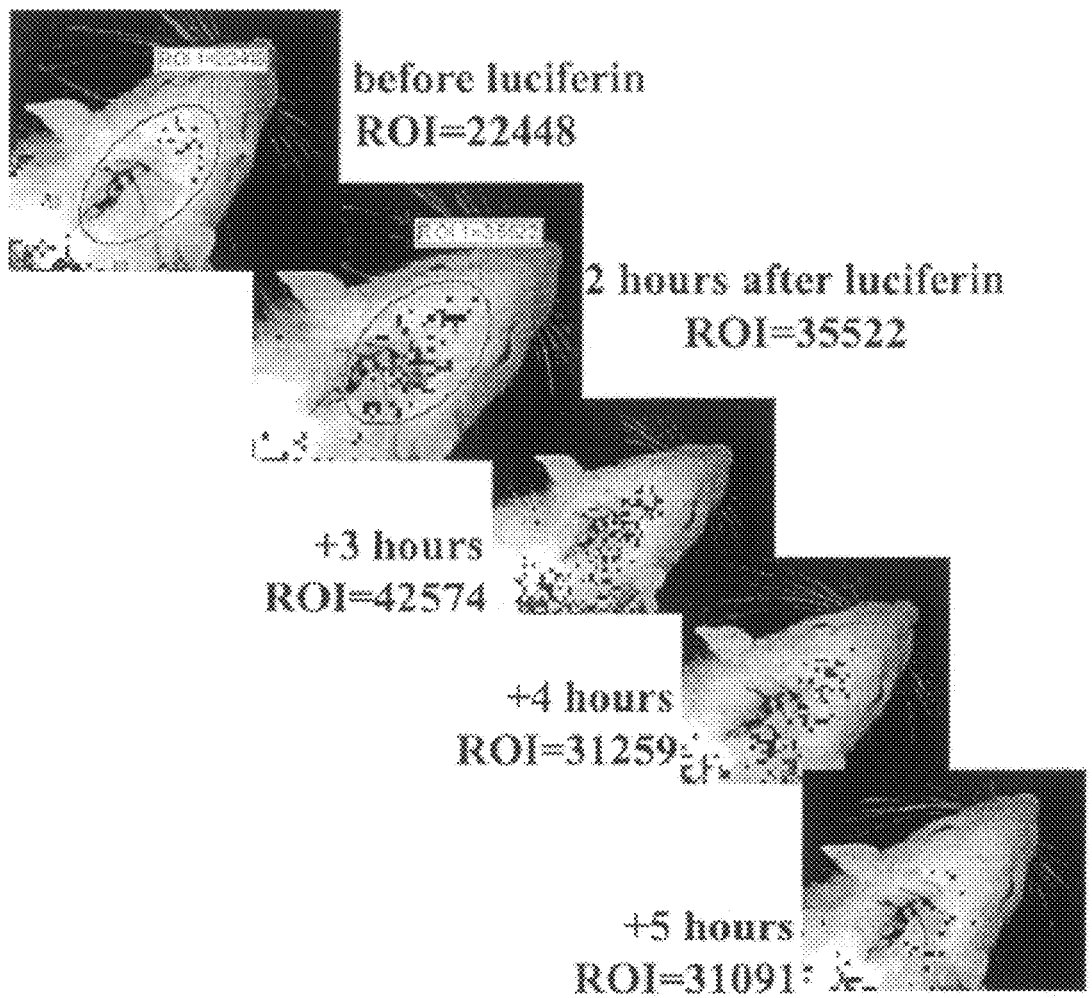
FIG. 14 provides a series of bioluminescent images showing a time course of expression following delivery of a lipoplex protected physiologically capped (ARCA-capped) mRNA to the cisterna magna injection. Luciferase expression was detected by rabbit polyclonal antibody against luciferase.
Figure 15:
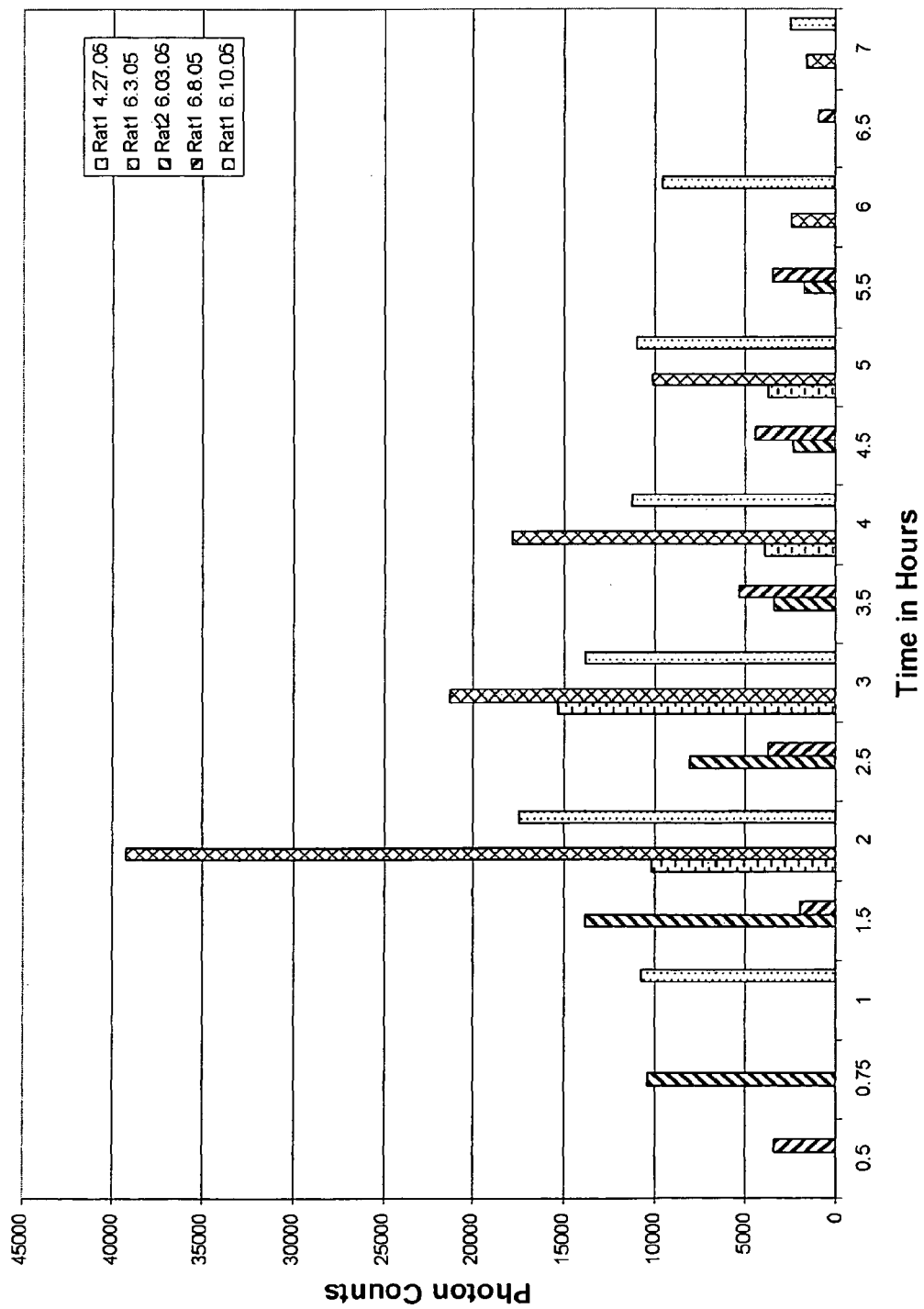
FIG. 15 shows a summary graph of the time course of FIG. 14, after mRNA delivery to the cisterna magna.

To confirm the finding at the cellular level that the distribution of luciferase in the brains of rats transfected with the vector complex via CSF injection was, in fact, widespread as detected by photon emission, particularly when compared to the distribution seen after parenchymal injection of the vector complex, the brains from a rat 72 hours after cisterna magna injection of the ARCA-capped mRNA vector complex (the time of peak luciferase expression by in vivo imaging) and a control rat (not injected) were sectioned and prepared as described above. Luciferase expression in these sections was detected using a rabbit polyclonal antibody against luciferase as shown in FIG. 14. As previously determined in FIG. 12, sections of transfected rat brain showed widespread cellular staining for luciferase, while sections of tissue from the non-injected rat did not. FIG. 15 shows a summary graph of the time course after mRNA delivery to the cisterna magna.

Thus, the in vivo results are consistent with and confirm the in vitro time course experiments in CHO, NIH 3T3 and primary neuronal cells. This widespread distribution of the expressed protein is important for future work with vectors carrying therapeutic genes. Although the number of copies of a given gene delivered to cells and the intracellular concentration of expressed protein from that gene that is needed to provide a therapeutic effect will vary with each clinical target, the demonstrated widespread uptake and expression of the vector by the present method is critical to successful therapy.

The disclosures of each patent, patent application and publication cited or described in this document are hereby incorporated herein by reference, in their entirety. However, the disclosed dates of publication may be different from the actual publication dates, which may need to be independently confirmed. No reference identified herein is to be construed as an admission that the present invention is not entitled to antedate such publication by virtue of prior invention.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method for non-viral delivery of a nucleic acid into the neuronal and non-neuronal cells of the central nervous system (CNS) of a subject to protect neuronal and non-neuronal cells from ischemic or traumatic injury, wherein the nucleic acid encodes a mono- or poly-peptide when operably-linked to a promoter, the method comprising:

complexing the nucleic acid encoding a mono- or polypeptide when operably-linked to a promoter with a cationic, lipid congener to form a lipid-based nucleic acid lipoplex or vector to protect and stabilize the nucleic acid; and intrathecally administering the lipoplex to the cerebrospinal fluid (CSF) of the subject to deliver the protected, stable and active nucleic acid to the neuronal and non-neuronal cells of the CNS of the subject, wherein the subject is a primate or a human; and wherein the copy number of the nucleic acid in the neuronal and non-neuronal cells of the CNS is at least 5-fold higher than in cells outside the CNS.

2. The method of claim 1, wherein the nucleic acid comprises DNA, cDNA, RNA, mRNA, siRNA or variants thereof, including RNAi and antisense molecules.

3. The method of claim 1, further comprising protecting the neuronal and non-neuronal cells of the CNS from ischemic or traumatic injury and preserving cell function.

4. The method of claim 1, further comprising protecting CNS neuronal cell function.

5. The method of claim 1, wherein the cationic, lipid congener comprises multiple variants and head groups suitable for neuronal and glial uptake in the CNS.

6. The method of claim 1, wherein the method further comprises preventing or decreasing the severity of neural or nervous system injury, neural damage associated with stroke, TBI, or SCI, or secondary injury following stroke, brain or spinal cord trauma, or neurodegenerative disease, including Alzheimer's disease, Parkinson's disease, Amyotrophic lateral sclerosis, and multiple sclerosis, or medical procedures with a risk of ischemia, hypoxia, hypotension or hyperthermia, including neurosurgical (brain) resections, aortic aneurysm procedures, cardiac bypass procedures, and carotid endarterectomy; improving recovery time from CNS injury; promoting nervous system cell repair and regeneration; pre-operative, peri-operative or post-operative protection from ischemic CNS damage.

7. The method of claim 1, comprising administering to the CSF prophylacticly.

8. A non-viral method for effecting the rapid, transient expression of nucleic acids in the neuronal and non-neuronal cells of the central nervous system (CNS) of a subject to protect neuronal and non-neuronal cells from ischemic or traumatic injury, wherein the nucleic acid encodes a mono- or polypeptide when it is operably-linked to a promoter, the method comprising: complexing the nucleic acid with a cationic, lipid congener to form a lipid-based nucleic acid lipoplex or vector to protect and stabilize the nucleic acid; intrathecally administering the lipoplex to the cerebrospinal fluid (CSF) of the subject to deliver the protected, stable nucleic acid to the neuronal and non-neuronal cells of the CNS of the subject; and effecting rapid, transient expression of the encoded polypeptide in those cells without cyto or neuro-toxicity, wherein the subject is a primate or a human and wherein the copy number of the nucleic acid in the neuronal and non-neuronal cells of the CNS is at least 5-fold higher than in cells outside the CNS.

9. The method of claim 8, wherein the nucleic acid comprises DNA, cDNA, RNA, mRNA, siRNA or variants thereof, including RNAi and antisense molecules.

10. The method of claim 8, further comprising protecting the neuronal and non-neuronal cells of the CNS from ischemic or traumatic injury and preserving cell function.

11. The method of claim 8, further comprising protecting CNS neuronal cell function.

12. The method of claim 8, wherein the cationic, lipid congener comprises multiple variants and head groups suitable for neuronal and glial uptake in the CNS.

13. The method of claim 8, wherein the expressed polypeptide is therapeutic when administered to the neuronal and non-neuronal cells of the CNS of the subject in vivo, in vitro, or ex vivo.

14. The method of claim 8, wherein the polypeptide is effective for preventing or decreasing the severity of neural or nervous system injury, neural damage associated with stroke, traumatic brain injury (TBI), spinal cord injury (SCI), or secondary injury following stroke, brain or spinal cord trauma, neurodegenerative disease, including Alzheimer's disease, Parkinson's disease, Amyotrophic lateral sclerosis, and multiple sclerosis, or medical procedures with a risk of ischemia, hypoxia, hypotension or hyperthermia, including neurosurgical (brain) resections, aortic aneurysm procedures, cardiac bypass procedures, and carotid endarterectomy; improving recovery time from CNS injury; promoting nervous system cell repair and regeneration; pre-operative, peri-operative or post-operative protection from ischemic CNS damage.

15. The method of claim 8, comprising administering to the CSF prophylacticly.

16. The method of claim 8, wherein the expressed polypeptide comprises a heat shock protein (HSP).

17. The method of claim 16, wherein the expressed polypeptide comprises HSP70 or HSP27.

18. A method for protecting neuronal and non-neuronal cells of the CNS from ischemic or traumatic injury and preserving cell function, the method comprising intrathecally administering to the cells a nucleic acid, wherein the nucleic acid is protected by forming a complex of the nucleic acid with a cationic, lipid congener to form a non-viral, cationic lipid-based delivery vector, wherein the nucleic acid encodes a mono- or poly peptide when it is operably-linked to a promoter, wherein the nucleic acid is protected and stabilized, and wherein the protected, stable nucleic acid remains capable of expressing the encoded polypeptide in the presence of endogenous nucleases, and wherein the copy number of the nucleic acid in the neuronal and non-neuronal cells of the CNS is at least 5-fold higher than in cells outside the CNS.

* * * * *